United States Patent
Jagger

(10) Patent No.: US 10,786,412 B2
(45) Date of Patent: *Sep. 29, 2020

(54) COMPUTER CONTROLLED LASER THERAPY TREATMENT TABLE

(71) Applicant: Mark Jagger, Mississauga (CA)

(72) Inventor: Mark Jagger, Mississauga (CA)

(*) Notice: Subject to any disclaimer, the term of this patent is extended or adjusted under 35 U.S.C. 154(b) by 415 days.

This patent is subject to a terminal disclaimer.

(21) Appl. No.: 15/270,932

(22) Filed: Sep. 20, 2016

(65) Prior Publication Data

US 2017/0065477 A1 Mar. 9, 2017

Related U.S. Application Data

(63) Continuation-in-part of application No. 13/421,433, filed on Mar. 15, 2012, now Pat. No. 9,446,260.
(Continued)

(51) Int. Cl.
*A61H 1/02* (2006.01)
*A61N 5/06* (2006.01)
(Continued)

(52) U.S. Cl.
CPC ......... *A61H 1/0222* (2013.01); *A61G 13/009* (2013.01); *A61H 1/0296* (2013.01);
(Continued)

(58) Field of Classification Search
CPC .. A61H 1/0222; A61H 1/0292; A61H 1/0296; A61G 13/08; A61G 13/009;
(Continued)

(56) References Cited

U.S. PATENT DOCUMENTS

| 776,335 A | 11/1904 | Langworthy |
| 902,946 A | 11/1908 | Nise |

(Continued)

FOREIGN PATENT DOCUMENTS

| WO | WO-02076552 A1 * 10/2002 | ......... A61H 23/0245 |
| WO | WO 02076552 A1 | 10/2002 |

OTHER PUBLICATIONS

DJO Tables and Traction 2010. Encore Medical LP, 2009. (Year: 2009).*

(Continued)

*Primary Examiner* — William J Levicky
*Assistant Examiner* — Nathan A Baldwin
(74) *Attorney, Agent, or Firm* — Thomas A. O'Rourke; Bodner & O'Rourke, LLP

(57) ABSTRACT

A multi-function, adjustable chiropractic table comprises a body section fixed to a table frame. A cervical section is movably attached to the table frame and securable at a desired angle. The cervical section comprises a padded head support, forehead strap, and neck bolsters. The head support is slidably mounted in a tray and translatable therein using a scissors mechanism, for linear axial traction. Pivotally mounting the tray to the cervical section permits lateral traction. A four-bar linkage, including a base frame, permits raising/lowering of the table using an actuator activated by a foot triggered wave switch comprising proximity sensors. The body section comprises a chest, lumbar, and leg sections. The chest section is replaceable with a treatment nodule comprising hot and cold compresses, or a laser enhanced spinal decompression therapy apparatus comprising a laser driven by two linear actuators to emit light according to one or more treatment protocols.

16 Claims, 55 Drawing Sheets

Related U.S. Application Data which is a continuation-in-part of application No. 13/236,465, filed on Sep. 19, 2011, now abandoned.

(60) Provisional application No. 61/465,200, filed on Mar. 15, 2011.

(51) Int. Cl.

| | | |
|---|---|---|
| *A61G 13/00* | (2006.01) | |
| *G16H 20/30* | (2018.01) | |
| *G16H 20/40* | (2018.01) | |
| *A61N 5/067* | (2006.01) | |
| *A61B 18/20* | (2006.01) | |
| *A61G 13/12* | (2006.01) | |
| *A61G 13/08* | (2006.01) | |
| *A61F 7/02* | (2006.01) | |

(52) U.S. Cl.
CPC ......... *A61N 5/0613* (2013.01); *A61N 5/0625* (2013.01); *G16H 20/30* (2018.01); *G16H 20/40* (2018.01); *A61B 2018/20351* (2017.05); *A61B 2018/20361* (2017.05); *A61F 7/02* (2013.01); *A61G 13/08* (2013.01); *A61G 13/121* (2013.01); *A61G 2203/34* (2013.01); *A61G 2203/36* (2013.01); *A61G 2203/40* (2013.01); *A61H 2201/0192* (2013.01); *A61H 2201/0207* (2013.01); *A61H 2201/0214* (2013.01); *A61H 2201/0228* (2013.01); *A61H 2201/0257* (2013.01); *A61H 2201/10* (2013.01); *A61H 2201/1607* (2013.01); *A61H 2201/1611* (2013.01); *A61H 2201/1638* (2013.01); *A61H 2201/1664* (2013.01); *A61H 2201/1676* (2013.01); *A61H 2201/5012* (2013.01); *A61H 2201/5015* (2013.01); *A61H 2201/5043* (2013.01); *A61H 2201/5046* (2013.01); *A61H 2201/5064* (2013.01); *A61H 2201/5071* (2013.01); *A61H 2201/5082* (2013.01); *A61H 2201/5092* (2013.01); *A61H 2201/5097* (2013.01); *A61N 2005/067* (2013.01); *A61N 2005/0626* (2013.01); *A61N 2005/0632* (2013.01); *A61N 2005/0644* (2013.01)

(58) Field of Classification Search
CPC ............... A61G 13/121; A61G 13/122; A61G 13/1225; A61N 5/0619; A61N 5/0625; A61N 5/0642; A61N 5/0643; A61N 5/0644

See application file for complete search history.

(56) References Cited

U.S. PATENT DOCUMENTS

| | | |
|---|---|---|
| 1,142,422 A | 6/1915 | Hawley |
| 1,205,649 A | 11/1916 | Miller |
| 1,239,522 A | 9/1917 | Rock |
| 1,374,115 A | 4/1921 | Roemer |
| 2,593,675 A | 4/1952 | Hastings |
| 2,630,800 A | 3/1953 | Voss |
| 2,674,996 A | 4/1954 | Stowel |
| 2,690,175 A | 9/1954 | Daughtry |
| 2,693,796 A | 11/1954 | Warner |
| 2,798,481 A | 7/1957 | Matthews |
| 2,808,049 A | 10/1957 | Graham |
| 2,865,367 A | 12/1958 | Sorenson |
| 3,302,641 A | 2/1967 | Berne |
| 3,570,479 A | 3/1971 | Horn |
| 4,002,165 A | 1/1977 | Lind |
| 4,387,888 A | 6/1983 | Marinakis |
| 4,589,126 A | 5/1986 | Augustsson et al. |
| 4,796,609 A | 1/1989 | Rix |
| 4,951,654 A | 8/1990 | Gambale |
| 5,014,688 A | 5/1991 | Fast |
| 5,207,216 A | 5/1993 | Sweeny |
| 5,454,436 A | 1/1995 | Smith |
| 5,782,870 A | 7/1998 | McAfee |
| 5,794,286 A | 8/1998 | Scott et al. |
| 6,077,293 A | 6/2000 | King |
| 6,152,950 A | 11/2000 | Shealy |
| 6,197,020 B1 | 3/2001 | O'Donnell |
| 6,638,299 B2 | 10/2003 | Cox |
| 6,821,288 B2 | 11/2004 | Schaeffer |
| 7,118,563 B2 | 10/2006 | Weckwerth |
| 7,189,214 B1 | 3/2007 | Saunders |
| 7,374,569 B2 | 5/2008 | Whatcott |
| 7,472,441 B1 | 1/2009 | Steffensmeier |
| 7,836,893 B2 | 11/2010 | Holiday |
| 8,033,284 B2 | 10/2011 | Porter et al. |
| 8,273,046 B2 | 9/2012 | Walther |
| 2004/0010299 A1 | 1/2004 | Tolkoff |
| 2004/0260367 A1 | 12/2004 | De Taboada |
| 2006/0100676 A1 | 5/2006 | Walmsley |
| 2006/0173514 A1 | 8/2006 | Biel |
| 2006/0206046 A1 | 9/2006 | Saunders |
| 2006/0287627 A1 | 12/2006 | Johnson |
| 2007/0106192 A1 | 5/2007 | Johnson |
| 2007/0162093 A1* | 7/2007 | Porter ................ A61N 5/0613 607/89 |
| 2007/0208289 A1 | 9/2007 | Walther |
| 2007/0208396 A1 | 9/2007 | Whatcott |
| 2008/0039751 A1* | 2/2008 | Yang ..................... A61H 39/04 601/101 |
| 2009/0069872 A1* | 3/2009 | Fortuna ............... A61N 5/0613 607/89 |
| 2009/0254154 A1* | 10/2009 | De Taboada ......... A61N 5/0613 607/88 |
| 2009/0299236 A1* | 12/2009 | Pryor ................ A61H 15/0092 601/18 |
| 2010/0324426 A1 | 12/2010 | Tucek |
| 2011/0270310 A1* | 11/2011 | Dyer ..................... A61F 5/055 606/242 |

OTHER PUBLICATIONS

Kaslow, Jeremy. "Lasers—Class IV Therapeutic.". https://web.archive.org/web/20100104151414/http://drkaslow.com/html/lasers—class_iv_therapeutic.html. Jan. 4, 2010. (Year: 2010).*

Kaslow, Jeremy, "Lasers-Class IV Therapeutic." https://web.archive.org/web/20100104151414/http://drkeslow.com/html/lasers_-_class_iv_therapeutic.html. Jan. 4, 2010. Web. Sep. 14, 2015.

* cited by examiner

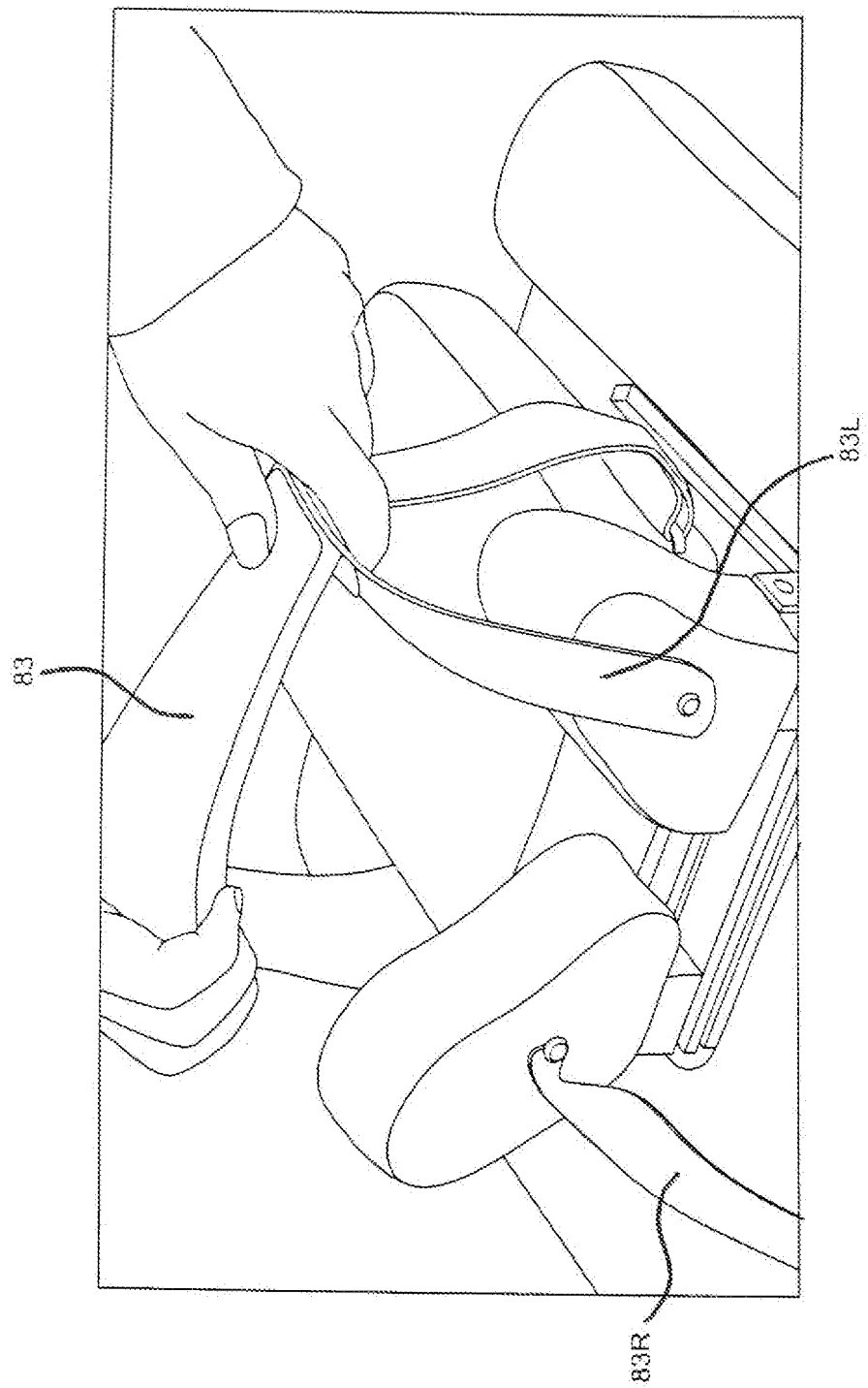

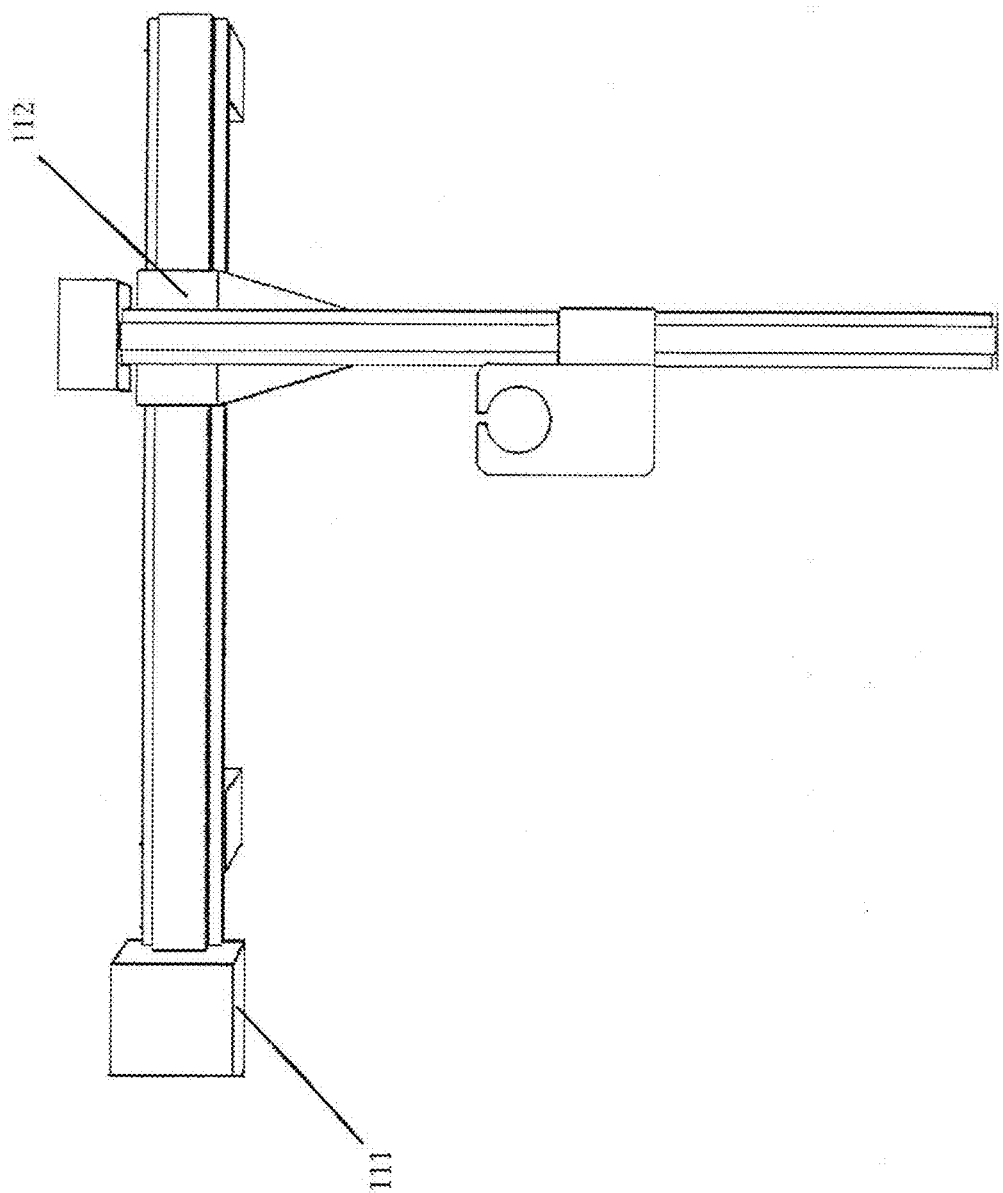

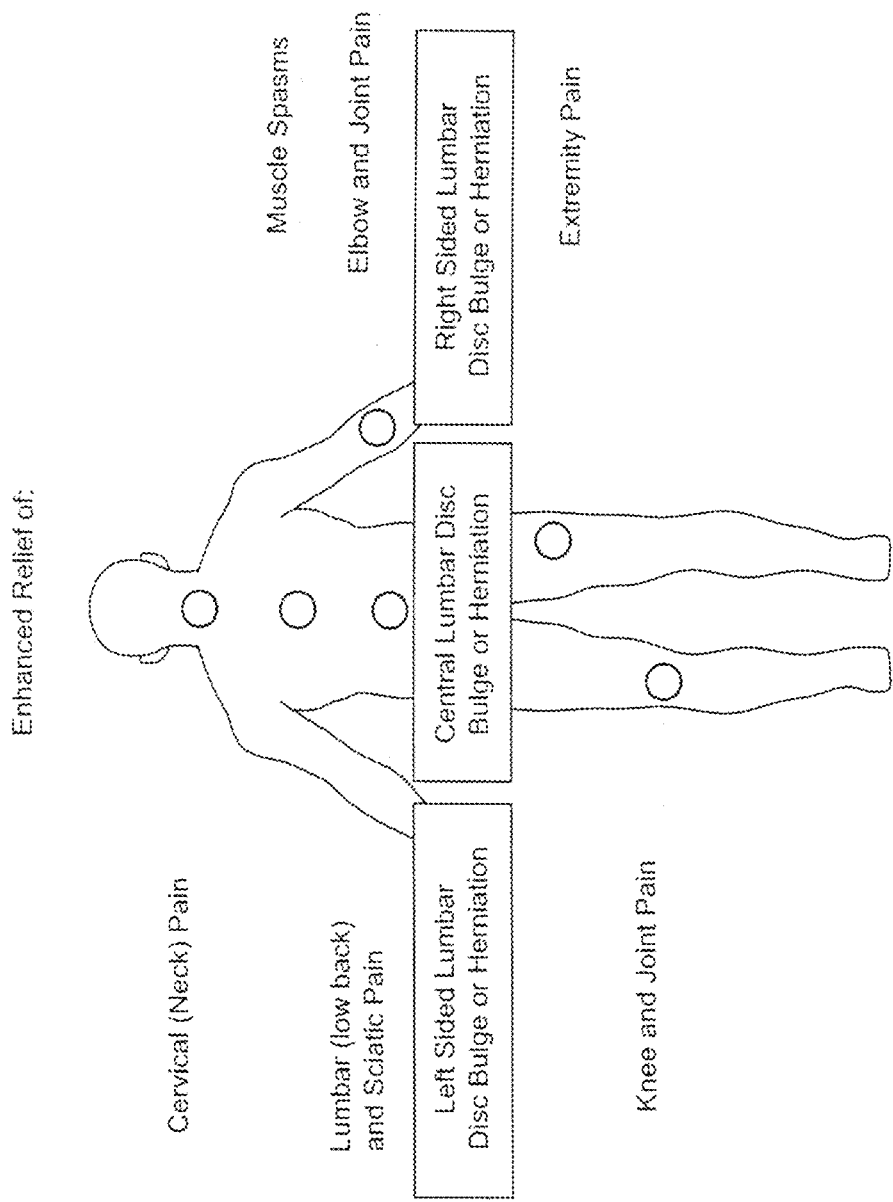

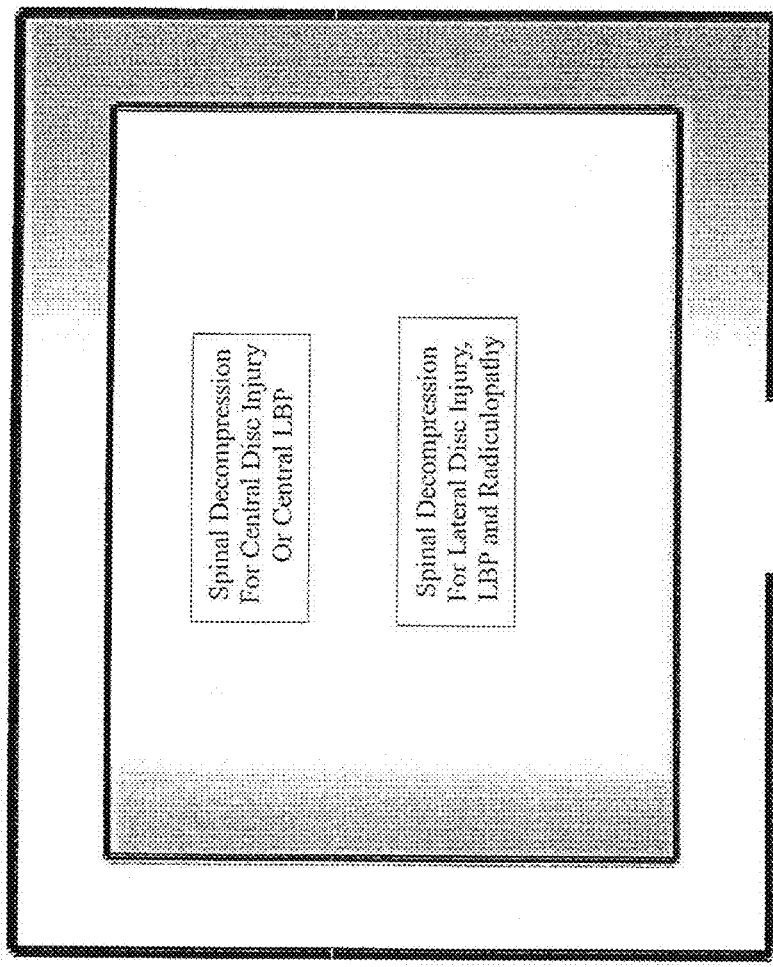
FIG. 15D
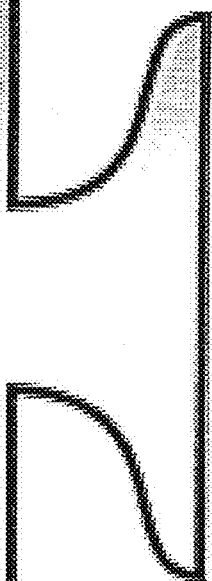
FIG. 15E
Left Sided Lumbar Disk Bulge or Herniation
FIG. 15F
Right Sided Lumbar Disk Bulge or Herniation

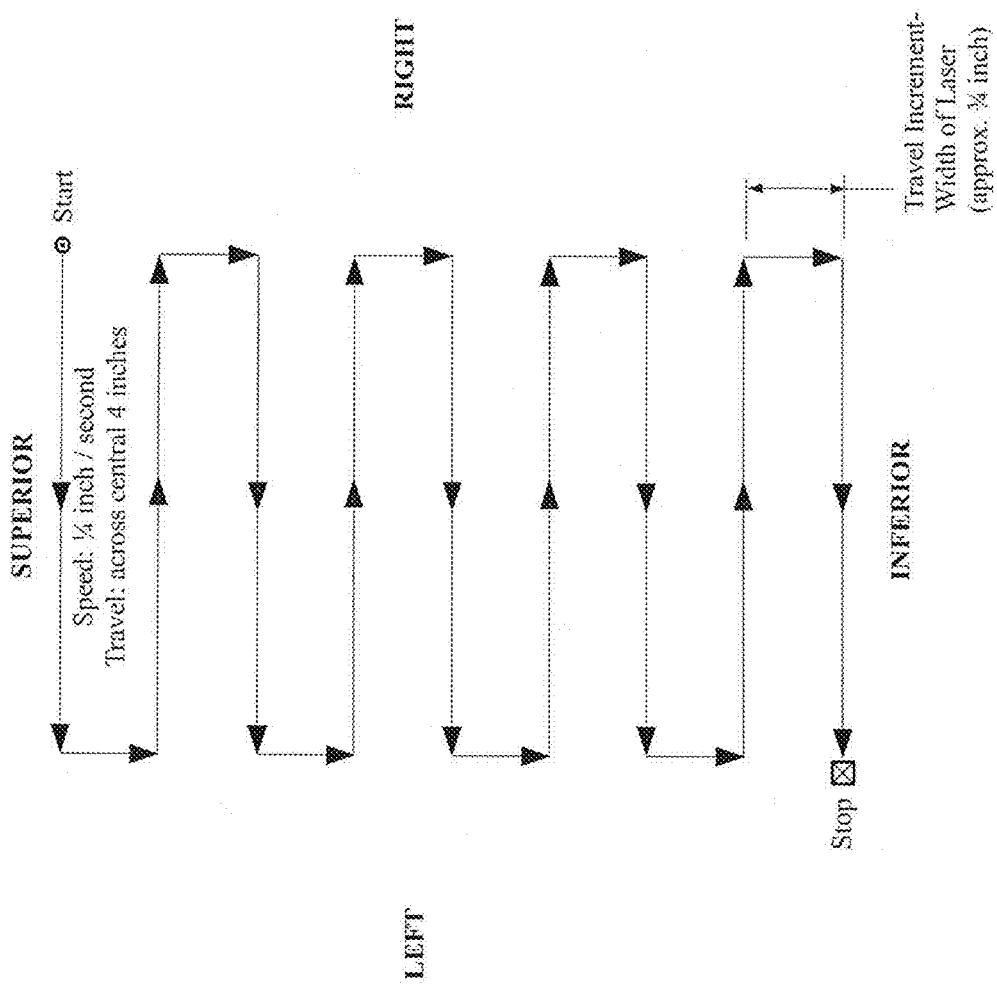

MOTION #3:
"Right Lateral Disk Involvement/Radiculopathy"
2 Components- Component "3A" below; Component "3B" in Figure 16D (General Treatment Protocol)

(General Treatment Protocol)

(Central Disk Bulge & Herniation Treatment Protocol: L4-S1)

1st Laser Light Pattern (Central Disk Bulge & Herniation Treatment Protocol: L4-S1)

2nd Laser Light Pattern (Central Disk Bulge & Herniation Treatment Protocol: L4-S1)

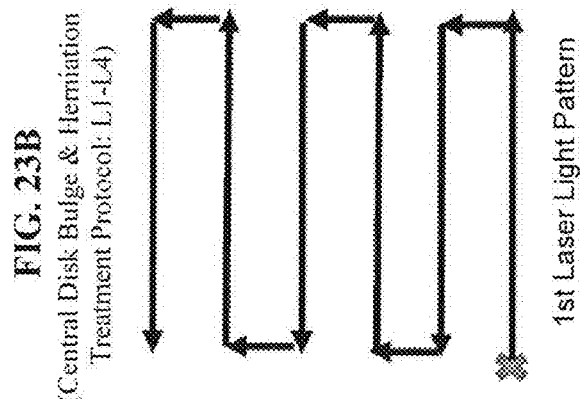
FIG. 23B (Central Disk Bulge & Herniation Treatment Protocol: L1-L4)
1st Laser Light Pattern
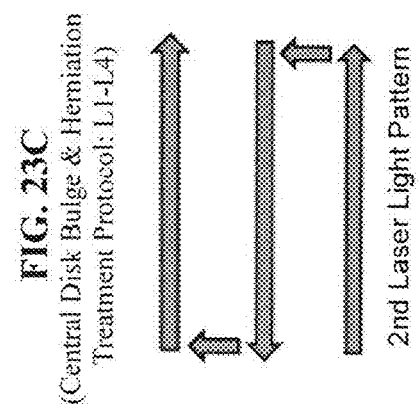
FIG. 23C (Central Disk Bulge & Herniation Treatment Protocol: L1-L4)
2nd Laser Light Pattern
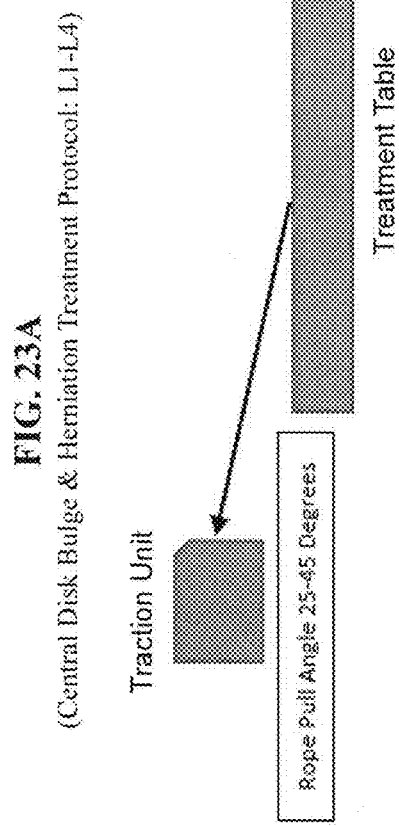
FIG. 23A (Central Disk Bulge & Herniation Treatment Protocol: L1-L4)

(Right Lateral Disk Bulge & Herniation
Treatment Protocol: L4-L5 & L5-S1)

1st Laser Light Pattern (Right Lateral Disk Bulge & Herniation
Treatment Protocol: L4-L5 & L5-S1)

2nd Laser Light Pattern (Right Lateral Disk Bulge/Herniation Treatment Protocol:
L4-L5 & L5-S1)

Treatment Table

Traction Unit

Rope Pull Angle 5-25 Degrees

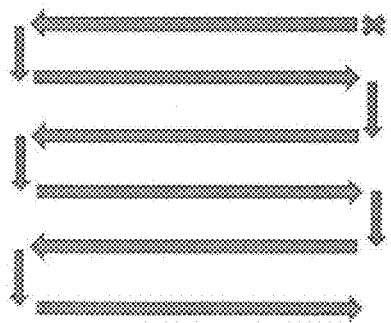
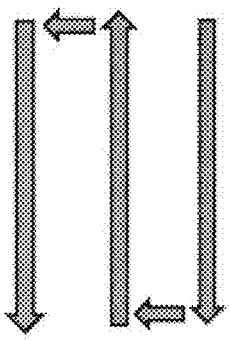
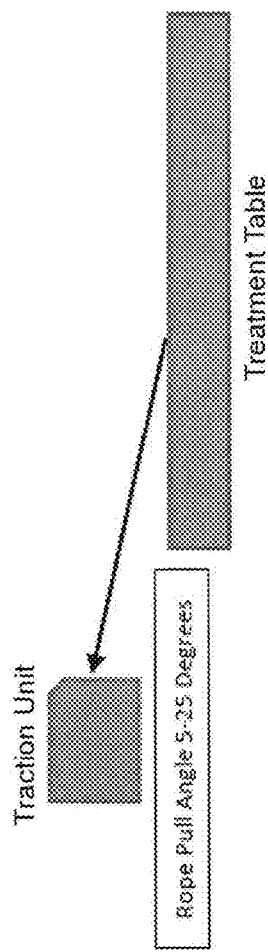

(Right Lateral Disk Bulge & Herniation Treatment Protocol: L1-L4)

1st Laser Light Pattern (Right Lateral Disk Bulge & Herniation Treatment Protocol: L1-L4)

2nd Laser Light Pattern (Right Lateral Disk Bulge/Herniation Treatment Protocol: L1-L4)

(Left Lateral Disk Bulge & Herniation Treatment Protocol: L1-L4)
1st Laser Light Pattern (Left Lateral Disk Bulge & Herniation Treatment Protocol: L1-L4)
2nd Laser Light Pattern (Left Lateral Disk Bulge/Herniation Treatment Protocol: L1-L4)

(Laser Acupuncture Treatment Protocol)

(Cervical Traction Treatment Protocol)

(Cervical Traction Treatment Protocol)

Pull Angle- Zero Degrees
Headrest
Neck Bolsters (Cervical Traction Treatment Protocol-
Right Lateral Cervical Disk Protrusion/Bulge/Herniation)

(Cervical Traction Treatment Protocol-
Right Lateral Cervical Disk Protrusion/Bulge/Herniation)

(Cervical Traction Treatment Protocol-
Right Lateral Cervical Disk Protrusion/Bulge/Herniation)

(Cervical Traction Treatment Protocol-
Left Lateral Cervical Disk Protrusion/Bulge/Herniation)

(Cervical Traction Treatment Protocol-
Left Lateral Cervical Disk Protrusion/Bulge/Herniation)

(Cervical Traction Treatment Protocol-
Left Lateral Cervical Disk Protrusion/Bulge/Herniation)

COMPUTER CONTROLLED LASER THERAPY TREATMENT TABLE

CROSS REFERENCES TO RELATED APPLICATIONS

This application is a continuation-in-part of U.S. application Ser. No. 13/421,433, filed on Mar. 15, 2012, which claims priority on U.S. Provisional Application. Ser. No. 61/465,200, filed on Mar. 15, 2011, titled "Innovations to Multi-Functional Medical/Rehabilitation Treatment Tables, Protocols and Associated Equipment," and which also is a continuation of U.S. application Ser. No 13/236,465, titled "Improved Multi-Function Medical/Rehabilitation Treatment Table and Equipment," filed on Sep. 19, 2011, with the disclosures of each incorporated herein by reference.

FIELD OF THE INVENTION

The present invention relates to the field of therapy tables, and more particularly to apparatus which are capable of providing increased performance capability for a medical practitioner while reducing the therapist's workload.

BACKGROUND OF THE INVENTION

Treatment tables are commonly used in various different medical fields, including the manual-therapy professions, such massage therapy, osteopathy, and physical therapy, and also for chiropractic medicine. Particularly for chiropractic treatments, a table may be necessary for a practitioner to perform certain examinations, adjustment, and procedures, as chiropractic physicians generally focus on the management of the neuro-musculoskeletal system without using medicines or surgery. Although the emphasis of such manual therapy may often be on the spine, for effective treatment of low back pain, lumbar disc herniation, etc., treatment may also be received on the cervical region for neck pain, some forms of headache, etc.

Therefore, treatment tables have been utilized for some time in these practices, with a typical example of such a chiropractic tables generally being illustrated within FIG. 1 of U.S. Pat. No. 7,472,441 to Steffenmeier for "Automatic Tilt-Elevating Chiropractic Table." However, despite the patentable and other advances that have been made to date, they have not developed sufficiently to support newer treatment techniques or to be able to provide the versatility and comfort level that is expected and needed by chiropractic patients. These deficiencies are addressed by the invention disclosed herein.

OBJECTS OF THE INVENTION

It is an object of the invention to provide a manual therapy treatment table, where the table is capable of being raised and lowered to suit the practitioner.

It is a further object of the invention to provide an improved means of triggering an actuator to extend or retract to raise or lower the table, which may occur by a conventional hand switch, a conventional foot pedal switch, and/or a wave switch system of the present invention which simply requires the practitioner waving a foot close to a tube.

It is another object of the invention to provide a manual therapy treatment table that includes an adjustable cervical section capable of linear axial traction, and also being capable of performing lateral traction as well.

It is a further object of the invention to provide a caster system being slidably attached to a base frame to be moveable between a first position where the casters are deployed and permit sliding transport of the table, and a second position where the casters are retracted and the frame provides stable static support for the table.

It is another object of the invention, to provide a cervical section head support offering improved padding and greater comfort provided by adjustable neck bolsters, as well as a three-point head strap to permit better securing of a patient's head without excessive tightening inherent in a conventional single strap system.

It is also an object of the invention to provide a pivotal traction platform to facilitate lateral traction for decompression therapy at a desired angle.

It is another object of the invention to provide a chest section, a lumbar section, and a leg section, each of which may be split into a fixed lower portion, and a removable upper padded portion that may be where replaceable with a treatment module.

It is also au object of the invention to provide an improved means of applying hot and cold compresses, through the use of electrically powered heating and cooling in a specialized treatment module.

It is another object of the invention to provide a treatment module permitting laser enhanced spinal decompression therapy.

Further objects and advantages of the invention will become apparent from the following description and claims, and from the accompanying drawing figures.

SUMMARY OF THE INVENTION

A multi-function, adjustable chiropractic table may comprise a table frame, a body section being fixedly secured to the table frame to support a patient's body, and a cervical section. The cervical section may be pivotally attached to a first end of the table frame to permit rotation relative to the body section, and may be secured to be at a desired angle with the table frame. A left arm pad with a bolster protruding upward therefrom, and a right arm pad with a bolster protruding upward therefrom may each be adjustably mounted to the table frame to be independently adjustable both medially and laterally, and they may also be independently adjustable both cephalically and caudally.

A padded head support may be mounted in an opening in a tray, with the tray being mounted to a plate of the cervical section. A forehead strap may be secured to the padded head support, and a pair of neck bolsters may also be pivotally mounted to the padded head support. The head support may be slidably mounted in tracks of the tray so as to be translatable relative to the tray, to thereby accomplish linear axial traction. The tray may be pivotally mounted to the cervical section to thereby accomplish lateral traction.

The multi-function adjustable chiropractic table may comprise a mechanism to permit the body section to be elevated and lowered, to accommodate the practitioner and patient. The mechanism may be constructed as follows. A first pair of mechanism supports and a second pair of mechanism supports may be fixed to a base frame, and may protrude upward therefrom. A first arm may have a first end being mounted to the first pair of mechanism supports to thereby be pivotable about a first axis, and the second end of the arm may be pivotally connected to the table frame. Also, a second arm may have a first end mounted to the second pair of mechanism supports to thereby be pivotable about a second axis, and the second end of the second arm may also be pivotally connected to the table frame. An actuator may have a first end be pivotally mounted to a portion of the base frame, and a second end be pivotally mounted to a portion of the first arm at a point being eccentric to the first axis. A connecting link may be pivotally connected to the first arm at a point being eccentric to the first axis, and may also be pivotally connected to the second arm at a point being eccentric to the second axis so that the motion of the second arm is slaved with movement of the first arm. So extension of the actuator drives the first an and the slaved second arm to causes raising of the table frame, and retraction of the actuator causes lowering of the table frame.

Triggering the actuator to extend or retract to thereby raise or lower the table may occur by one or more of a conventional hand switch, a conventional foot pedal switch, and a wave switch system of the present invention. The wave switch system may comprise either one or more sensor tubes positioned peripherally about the base frame, such that the raising/lowering of the table occurs by waving of a foot to toggle the sensor tube in either of two different directions.

The multi-function adjustable chiropractic table may further comprise two or more casters being slidably attached to the base frame and being moveable between a first position and a second position, where in the first position, each of the casters extends below the base frame with the casters supporting the table, and where in the second position, each of the casters are positioned above a bottom surface of the base frame and the base frame supports the table. Each of the two or more casters may have a linear actuator to cause the movement between the first and second positions, where the linear actuators may be simultaneously activated by a switch.

The multi-function adjustable chiropractic table may further comprise a traction platform being pivotally secured to the base frame in proximity to the table frame at the end which opposite to the end having the cervical section attached thereto. The traction platform may be laterally adjustable using either a tension knob on the platform being securable to a plate on the base frame, or using a locking pin on the platform being received in one of a plurality of holes in the plate. The traction platform may facilitate a machine for providing lateral traction for decompression therapy at a desired angle.

The body section of the chiropractic table, described above, may further comprise a chest section, a lumbar section, and a leg section. Each of the chest section, the lumbar section, and the leg section may comprise padding. Any of these sections, and particularly the lumbar section, may be split into a fixed lower portion and a removable upper padded portion, where the removable upper padded portion may be replaceable with a treatment module being secured to the fixed lower section. The treatment module may be traditional hot and cold compresses, or may comprise electrically powered heating and cooling.

A novel treatment module may comprise a laser enhanced spinal decompression (LESD) apparatus being secured to the base portion of the lumbar or other sections, including the cervical section. The apparatus for the laser enhanced spinal decompression apparatus may comprise a first linear actuator and a second linear actuator, which may be usable to position the laser along an X direction (medially and laterally) and along a Y direction (cephalically and caudally) for unassisted treatments. The laser as well as the first and second linear actuators may preferably be mounted within an enclosure or box. The laser box may have a cushioned gland around a top perimeter of the box to serve in creating a seal against a patients' skin surface to thereby reduce or eliminate the escape of any laser light.

The laser may emit laser light upon a spine of a patient, with the laser translating in the X and Y directions and being directed to emit light according to patient-specific; or protocol-specific treatment requirements. The laser enhanced spinal decompression apparatus may further comprise a controller that interfaces with a computer operating system to permit the treatment protocols to be pre-programmed and/or customized. A range of motion for the laser light of one treatment protocol may comprise travel of approximately 8 inches or more to each side of a center of a patient's spine, and travel up and down a patient's spine to cover spinal disks from L1 to S1 (Note—The table may be configured to facilitate laser treatment of each of the thirty-three human vertebrae). The laser enhanced spinal decompression apparatus may also include one or more sensors, such as proximity sensors, optical sensors, temperature sensors, pressure sensors, and motion sensors, which may be usable for ensuring proper treatment. For example, one or more temperature sensors may be used for thermographic imaging to monitor tissue temperatures to achieve an optimal dosage.

BRIEF DESCRIPTION OF THE DRAWINGS

FIG. 7 is a perspective view of the cervical section showing the rotatable neck support bolsters attached and in proper relation to the padded head support, along with a head strap extending from the head support, and secondary straps extending from the neck bolsters and having Velcro thereon to thereby be securable to the head strap.

FIG. 12A is a front perspective view showing partial assembly of two linear actuators that are used to create "X" and "Y" motion to position a laser during Laser Enhanced Spinal Treatment.

FIG. 15A is a screen shot of the software of/be current invention being run on the laptop of FIG. 14B, and illustrating the various regions of/be body upon which the laser may be used for treatment.

FIG. 15D-FIG. 15F are screen shots illustrating yet other aspects of the software of the current invention, showing window button options for spinal decompression therapy of central disk, right-side disk, and left-side disk regions.

FIG. 16A-16H show drawings for the pre-programmed automated laser motion protocols for various conditions.

FIG. 23A is a schematic illustration showing the rope angles formed by the positioning of the traction unit with respect to the treatment table, for a treatment protocol for central disc bulge/herniation at L1-L4.

FIG. 23B illustrates a first laser light pattern used with corresponding rope angles for the treatment protocol of FIG. 23A.

FIG. 23C illustrates a second laser light pattern used with corresponding rope angles for the treatment protocol of FIG. 23A.

FIG. 25A is a schematic illustration showing the rope angles formed by the positioning of the traction unit with respect to the treatment table, for a treatment protocol for left lateral disc bulge/herniation at L4-S1.

FIG. 25B illustrates a first laser light pattern used with corresponding rope angles for the treatment protocol of FIG. 25A.

FIG. 25C illustrates a second laser light pattern used with corresponding rope angles for the treatment protocol of FIG. 25A.

DETAILED DESCRIPTION OF THE INVENTION

Figure 1A:
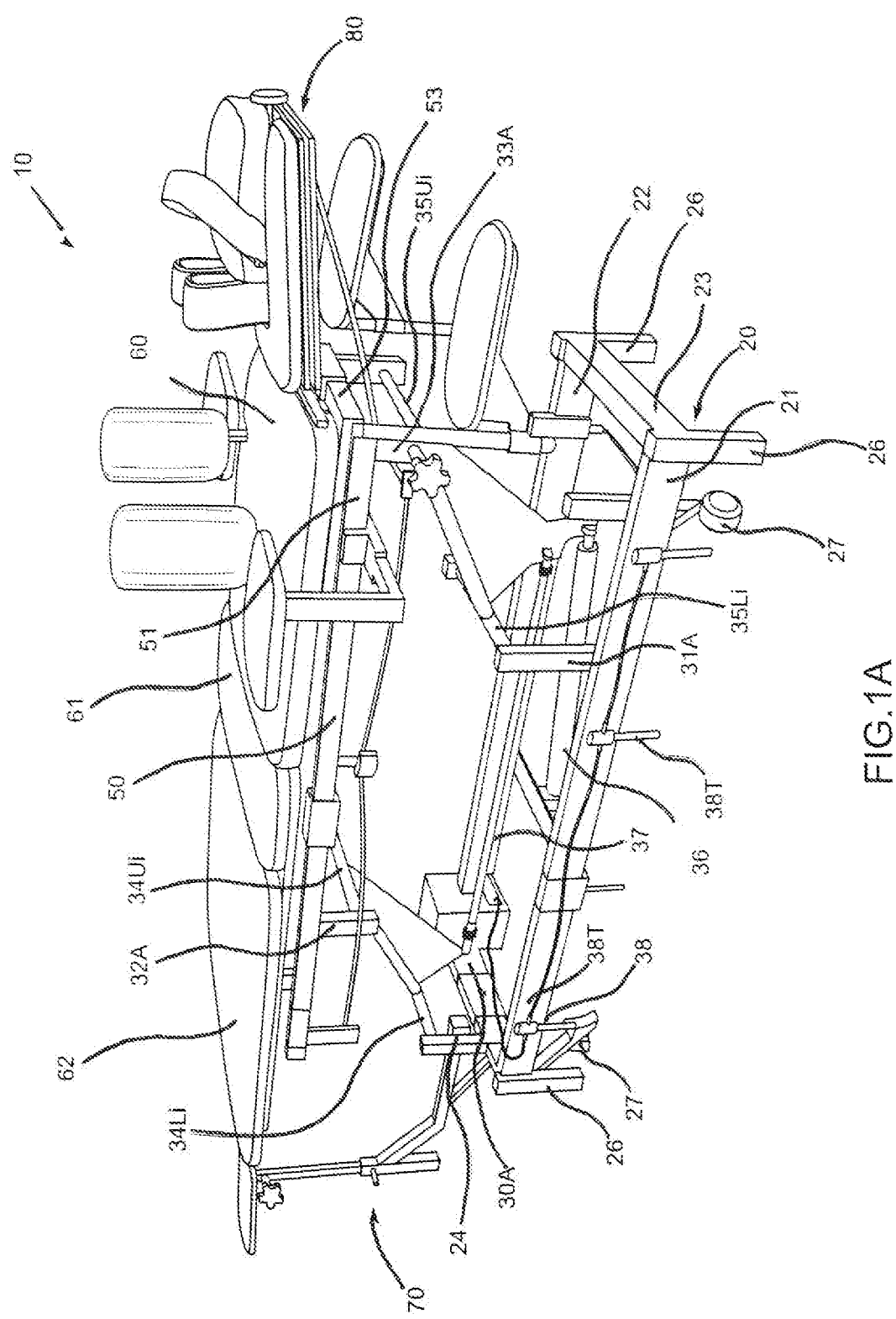
FIG. 1A is a perspective view of the multi-functional treatment table of the present invention.

As used throughout this specification, the word "may" is used in a permissive sense (i.e., meaning having the potential to), rather than the mandatory sense (i.e., meaning must). Similarly, the words "include", "including", and "includes" mean including but not limited to.

The phrases "at least one", "one or more", and "and/or" are open-ended expressions that are both conjunctive and disjunctive in operation. For example, each of the expressions "at least one of A, B, and C", "one or more of A, B, and C", and "A, B, and/or C" mean all of the following possible combinations: A alone; or B alone; or C alone; or A and B together; or A and C together; or B and C together; or A, B and C together.

Also, all references (e.g., patents, published patent applications, and non-patent literature) that are cited within this documents are incorporated herein in their entirety by reference.

Furthermore, the described features, advantages, and characteristics of any particular embodiment disclosed herein, may be combined in any suitable manner with any of the other embodiments disclosed herein.

FIG. 1 shows a first embodiment of the multi-function adjustable treatment table assembly 10 of the present invention. The table may comprise a base (support) frame 20 which may be made of a single unitary piece, which may be thrilled a machined part or a cast part. In general, the base frame 20 may formed at least a first elongated side 21 and a second elongated side 22, which may be connected by a first cross-member 23 and a second cross-member 24. Where four separate elongated sides 21 and 22, and separate cross-members 23 and 24 are utilized, they may be secured together using any suitable mechanical fasteners, or they may be welded together.

Extending downward from the base frame 20 may be four support legs 26 being fixed to the frame, and preferably spaced about the frame to provide stable support. In one embodiment, the legs 26 may be at a location proximal to the joining of the sides 21 and 22, and cross-members 23 and 24. The multi-function adjustable chiropractic table 10 may further comprise two or more casters 27 being slidably attached to the base frame 20 so as to be moveable between a first position and a second position. The first position may be a lowered, position where each of the casters 27 extends below the bottom surface of the base frame 20 to contact the ground and thereby support the table. The second position may be a raised position where the bottom of each of the casters 27 is positioned above the bottom surface of the base frame, so that the base frame is resting upon the ground. Each of the casters 27 may have a linear actuator to drive the movement between the first and second positions, and to lock the casters at each of those positions. The linear actuators may be simultaneously activated by a foot/hand switch. In a preferred embodiment, there may be four casters, with one being located proximate to each of the four legs 26, which, when deployed down to be in the first position, may permit rolling movement and relocation of the table assembly 10.

A body support section of table assembly 10 may be fixed to a table frame 50, and may comprise a chest section 60, a lumbar section 61, and a leg section 62 with each of those sections comprising a rigid support plate and padding thereon. The table frame 50 may be formed similar to the base frame 20, to be a single member, or it may be a build-up of four different members-two side members 51, 52, and two cross-members, 53, and 54. Raising and lowering of the body support section—the table frame 50 mounted chest section 60, lumbar section 61, and leg section 62—may be relative to the statically positioned base frame 20, and may occur through the use of a mechanism connecting the base frame 20 and the table frame 50. In a simple embodiment, a pair of arms may each have a first end be pivotally connected to the base frame 20 and have a second end be pivotally connected to the table frame 50.

In a preferred embodiment, table assembly 10 may have a first lower pair of mechanism supports, being first support 30A and second support 308, and a second lower pair of mechanism supports, being third mechanism support 31A and fourth mechanism 318, with each of those supports being fixed to the base frame 20, using fasteners or by welding, to protrude upward therefrom. Similarly, table assembly 10 may have a first upper pair of mechanism supports 32A and 328, and a second upper pair of mechanism supports 33A and 33B, with each of those supports being fixed to the table frame 50, using fasteners or by welding, to protrude downward therefrom. A first arm 34 may have a first end and a second end. The first end may comprise pins 34Li and 341Lii protruding from opposite sides of the arm 34 to be concentric with a first axis, tot pivotal mounting within the first lower pair of mechanism supports 30A and 30B. The second end may comprise pins 34Ui and 34Uii protruding from opposite sides of the arm 34 for pivotal mounting within the first upper pair of mechanism supports 32A and 328. A second arm 35 may have a first end and a second end. The first end may comprise coaxial pins 35Li and 35Lii, protruding from opposite sides of the arm 35 to be concentric with a second axis, for pivotal mounting within the second lower pair of mechanism supports 31A and 31B. The second end may comprise pins 35Ui and 35Uii protruding from opposite sides of the arm 35 for pivotal mounting within the second upper pair of mechanism supports 33A and 338.

Figure 1C:
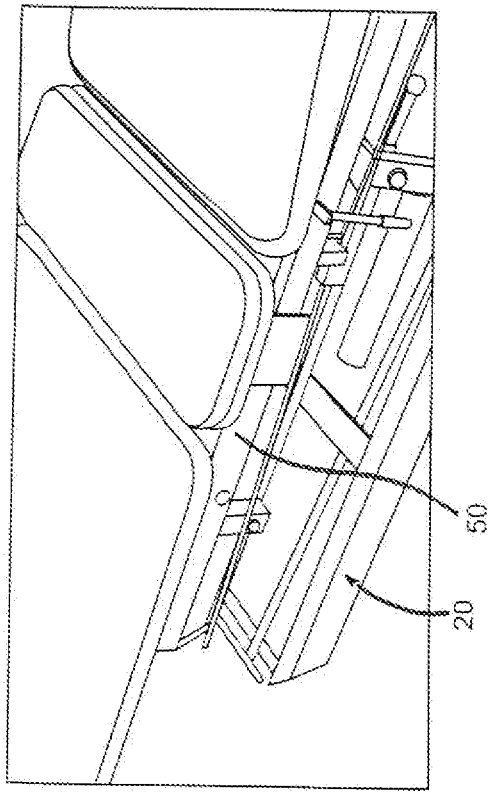
FIG. 1C is a perspective view showing the table of the present invention in a position prior to being lowered.
Figure 1D:
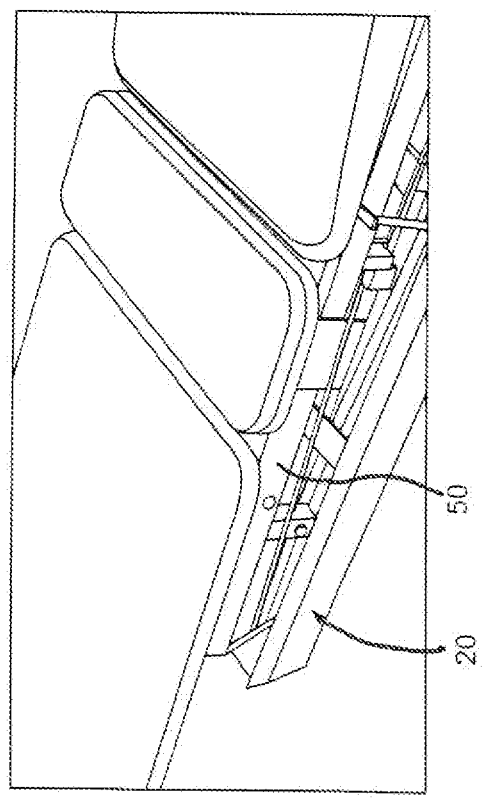
FIG. 1D is a perspective view showing the table of FIG. 1C after being actuated to be in a lower position.

An actuator 36 may have one end pivotally connected to the base frame 29, and a second end pivotally connected to the second arm 35 at a point being eccentric to the second axis. A connecting link 37 may have a first end be pivotally connected to the first arm 34 at a point being eccentric to the first axis, and may also have a second end be pivotally connected to the second arm 35 at a point being eccentric to the second axis to thereby slave the motion of the second arm to that of the first arm, when the first arm is actuated by actuator 37. With this arrangement, extension of the actuator 37 may result in elevating of the upper frame 50 and body support sections, and retraction of the actuator may conversely cause lowering of the upper frame (FIGS. 1C-1D). As the table 10 will generally be stationary, movement of the body support section may thus occur through rotation of the first arm about the first axis centered on pins 34Li and 34Lii, and by rotation of the second arm about the second axis centered on pins 35Li and 35Lii.

A modular power supply system may be utilized for the actuator/motor drive 37, to raise and lower the table, which exhibits proven reliability, safety, and ruggedness. A separate power supply, and control system allows inclusion of safety and control features, which enhance user friendliness and operational efficiency. A DC power supply/control system 12/24 volt mode gives increased lift capacity, while a 12 volt mode for lowering, gives reliable braking function for safe lowering.

Figure 1B:
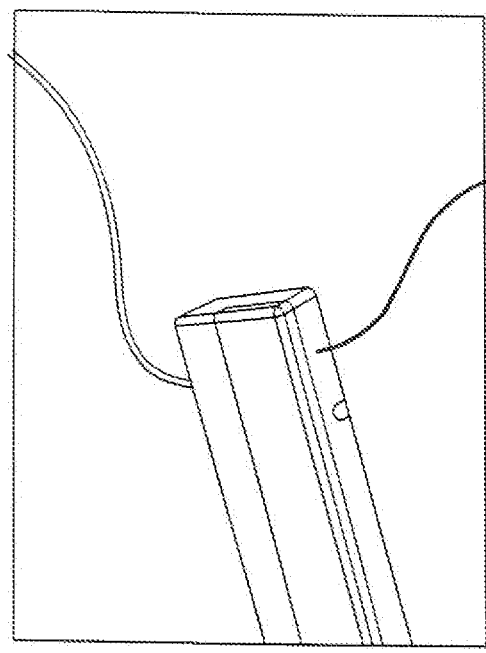
FIG. 1B is a perspective view showing a foot pedal usable for raising and lowering of the table.
Figure 3:
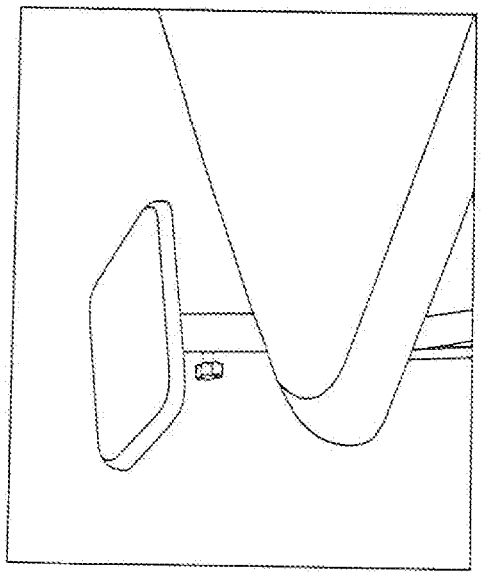
FIG. 3 is the perspective view of the traction machine platform of FIG. 2, with it being shown after being moved into a second position.

A foot pedal 37, as seen in FIG. 1B, may comprise switch that controls actuator extension and retraction, to cause elevating and lowering of the table. The foot pedal may be replaced by or complemented through the use of what is termed herein a "wave switch system," where a slight wave of the operator's toe is all that is needed to trigger the actuator 36 to raise or lower the table. The wave switch 38 may be mounted on the base frame 20 at one to four, or even more different places, and may be connected with a daisy-chain expandable/retractable electronic harness. A mounting bracket for each of the switches may be moveable to a particular desired position on the base frame 20. For any desired height adjustment of the table, all that is needed is a wave of the toe, against a resilient (rubberlike) tube 38T.

The tube 38T may lie made from flexible, semi-rigid material that attaches to a pendulum-like mechanism within the body of the switch at one end that attaches to the base frame 20, while the other end of the tube extends down to approx. ½" to 1" above the floor when the table is resting on the base frame 28 (not being supported by the casters 27). The wave switch 38 is intended to replace traditional hand switches (thus freeing up practitioners' hands) and traditional foot switches, that often get left in awkward, inconvenient places, making it difficult for the practitioner to spontaneously change the height of the table, particularly since the practitioner may also wish to freely move around to different area of the table and nonetheless retain the ability to adjust the table's height while applying treatments. The wave switches 38 can be "daisy chained" with flexible cabling around the bottom rail of the base frame so that a switch is located at regular intervals around the table.

The practitioner simply pushes the tube 38T with the side of his foot in one direction to activate the system to raise the table, and conversely pushes the tube 38T in the opposite direction to lower the table. The tube 38T is designed to be flexible to allow an object, such as a practitioner's foot, to push it in any direction, and even push it past the intended range of motion, without breaking or stressing the components of the switch. The pendulum that the tube is attached to may be spring-biased to return the tube to its center position, which is typically the "off" position. The switching components inside the housing of the "wave switch" may be a mechanical device (push button or lever), or may be a magnetic device, or may even be a proximity sensing device, all of which may be activated when the tube/pendulum is pushed in either direction to make contact with the internal switching target area. The switches may be connected together and connected to the power controller 40 (FIG. 1) with modular disconnect cabling that receives the signal from the switch to activate and power the actuator 36 that raises or lowers the table.

Figure 18:
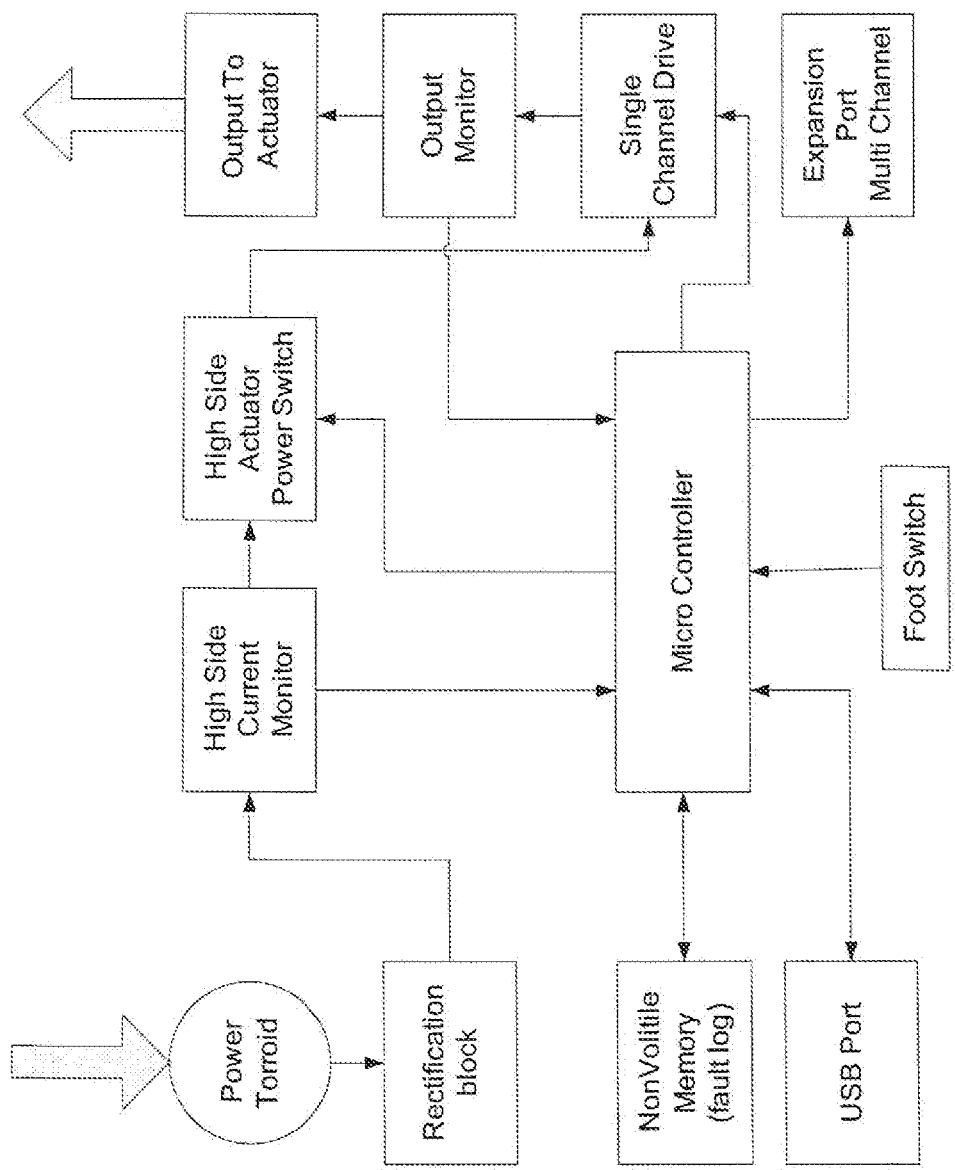
FIG. 18 is a block diagram of the control system of the multi-functional treatment table of the present invention.

The power (micro) controller 40 herein will comprise solid state electronics and add advanced features such as an over temperature and over current shut down, and fault diagnostics with safe shut down will be included. A set of LEDs may be used for user indication of system status. A system log may be maintained in the controller. This log can be retrieved via a common USB memory stick. This data can be sent back to the table's manufacturer via a simple email attachment. The log will contain system build information, fault information, and a usage log. The power controller 40 may comprise other new capabilities (FIG. 18), including a web interface for large institutions and practitioners to see usage reports from each table—reports that quantifies the usage of each table for maximum efficiency. This may also include:
- Remote access to adjust table functions and trouble-shoot through an internet portal;
- Options to create a link to the internet may include the following:
  - Ethernet connection, wireless connections such network card, blue tooth, cellular connection, USB internet access stick, etc.;
- Greater automation of table functions, such as pad adjustments;
- A user interface device that plugs into the power controller, with a display and buttons/switches or touch screen for controlling, monitoring and adjusting functions and seeing relevant information, such as patient information, pre-set functions, treatment protocols, etc; and
- Data storage and retrieval of patient information as it relates to treatment protocols and practitioner requirements.

Extending from one end of the upper frame 50, and being adjacent to chest section 60, may be a cervical section 80, which is shown in greater detail in FIGS. 5A-5F. The cervical section 80 may be pivotally attached to a first end of the upper frame 50 to permit rotation and securing of the cervical section (angled upward or downward) at a desired angle with respect to the body support section, and may be locked into position with a locking gas spring or locking pin and or lever 86 (FIG. 5G).

The cervical section 80 may comprise a padded head support 81. Adjustable neck bolsters 82L and 82R mount at each side of head support 81. The custom bolsters 82L and 82R are designed to be positioned at each side of the patients' neck at the base of the skull and are padded, contoured and adjustable for a comfortable it for each patient. The cervical section 80 further comprises a unique fully adjustable three-point cervical retainer strap system (FIG. 7) to hold the patient's head snugly, yet comfortably. This addresses a problem with current traction device strapping systems, which are inadequate for securing patients with different head sizes, and shapes, particularly for a patient with a sloping forehead, which generally results in the strap sliding across the forehead during traction. This three-point cervical retainer strap system may include one wide over-forehead strap 83 to secure the patients head and two smaller temporal straps, 83L and 83R, which are respectively secured to the bolsters 82L and 82R and may fasten to the over-forehead strap to prevent it from translating. Securing to the strap 83 may be using snap fasteners, hook and loop fastening materials (a descriptive name), sold under the trademark name of Velcro®, or any other suitable fastening system. Also, strap 83 may be a single elastic strap, or may alternatively be a split strap with Velcro attached respectively to each end to be securable about a patient's forehead. As a result of this arrangement herein, practitioners no longer need to secure a single strap around a patient's forehead so tightly, as had been necessary with other tables, and which tended to cause patient discomfort. Thus this strap/holster/padded support arrangement generally improves upon the treatment imparted to the patient.

Figure 8A:
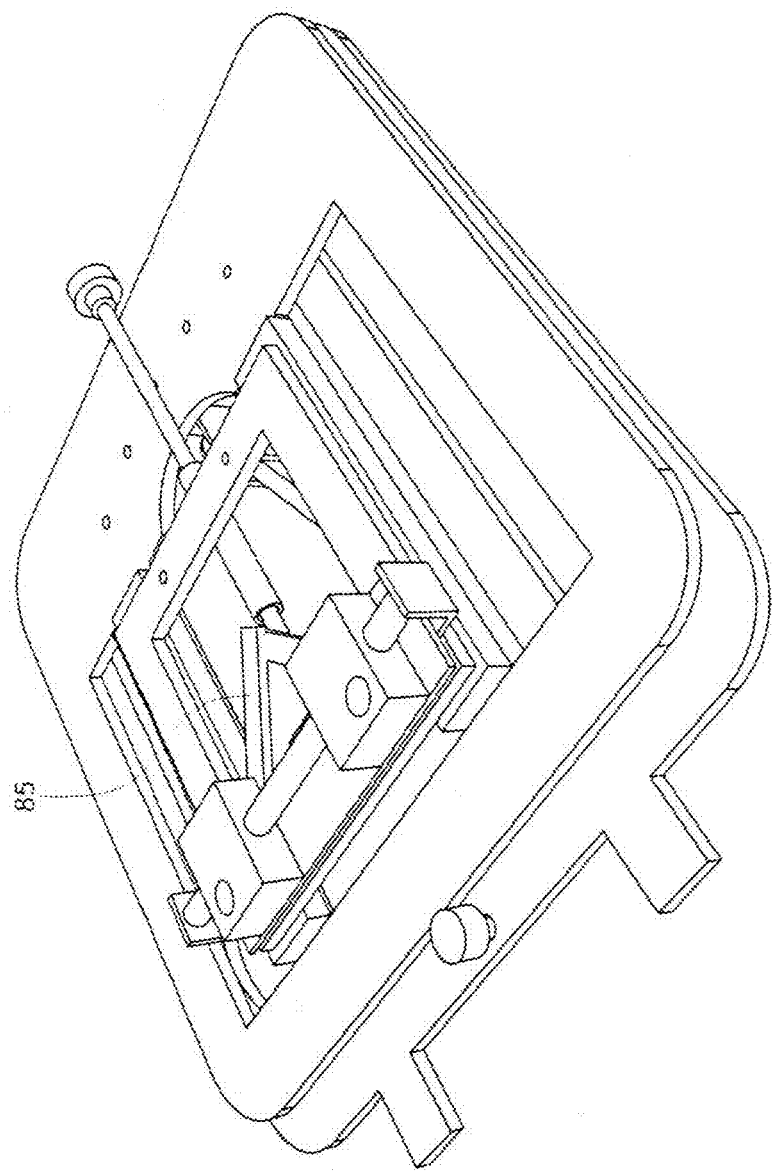
FIG. 8A is a top perspective view of the scissors-style mechanism of the cervical section tray, usable to provide adjustments to the neck holsters.
Figure 8B:
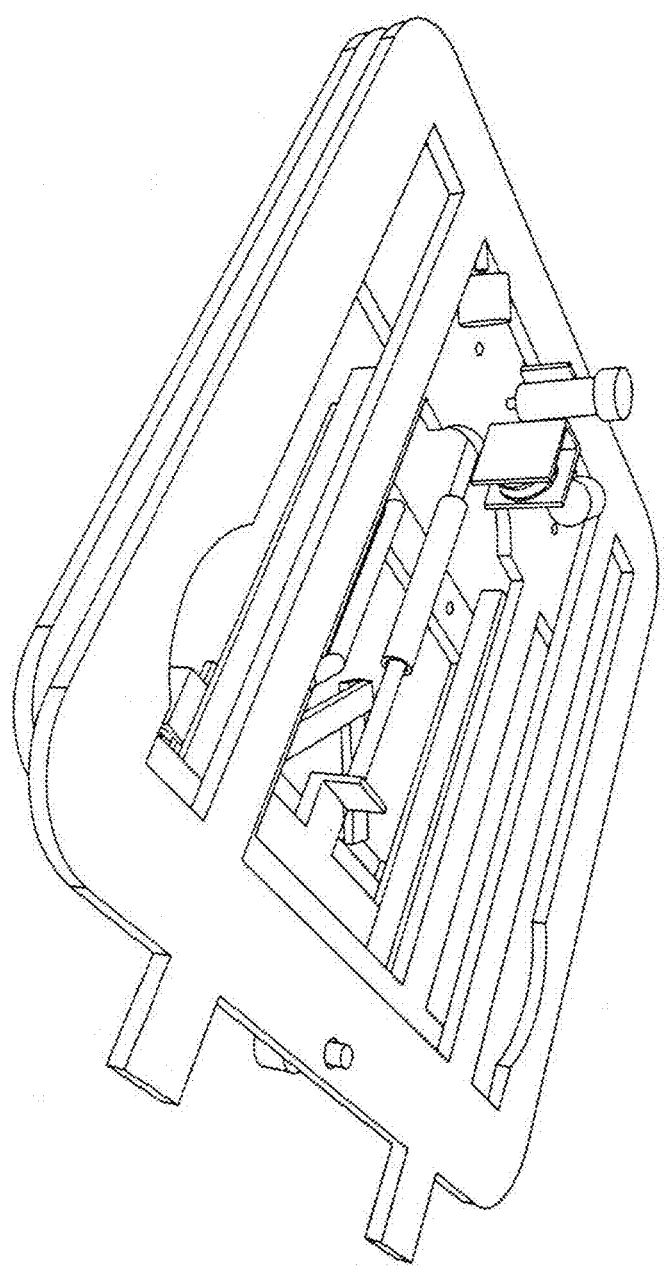
FIG. 8B is a bottom perspective view of the scissors-style mechanism of FIG. 8A.

Adjustment of the neck bolsters 82L/82R inward or outward to accommodate different sized patients may occur through the use of a scissors mechanism 85, which is shown in FIG. 8 during its sub-assembly, and which operates similarly to the arrangement in expired U.S. Pat. No. 4,089,435 to Corompt for "Transportation Equipment." the disclosures of which are incorporated herein by reference. The winding knob and threaded rod combination 84 of FIG. 5D may be rotated to adjust the bolsters inward or outward.

Figure 5B:
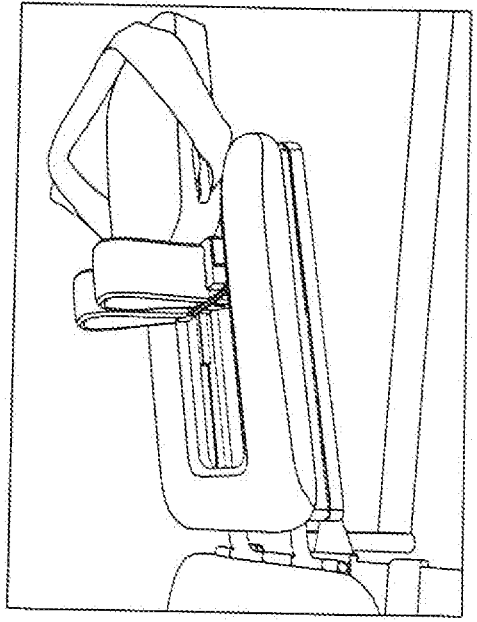
FIG. 5B is the perspective view of the padded head support of FIG. 5A, adjusted to provide traction and being in a second position, being at an extreme limit of travel for the support.
Figure 5D:
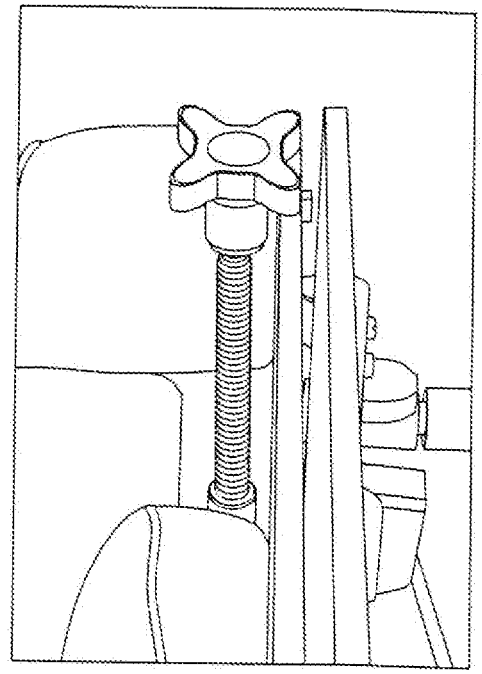
FIG. 5D is a perspective view showing a winding knob being usable to drive a scissors mechanism to actuate the neck holsters of the head support.
Figure 5A:
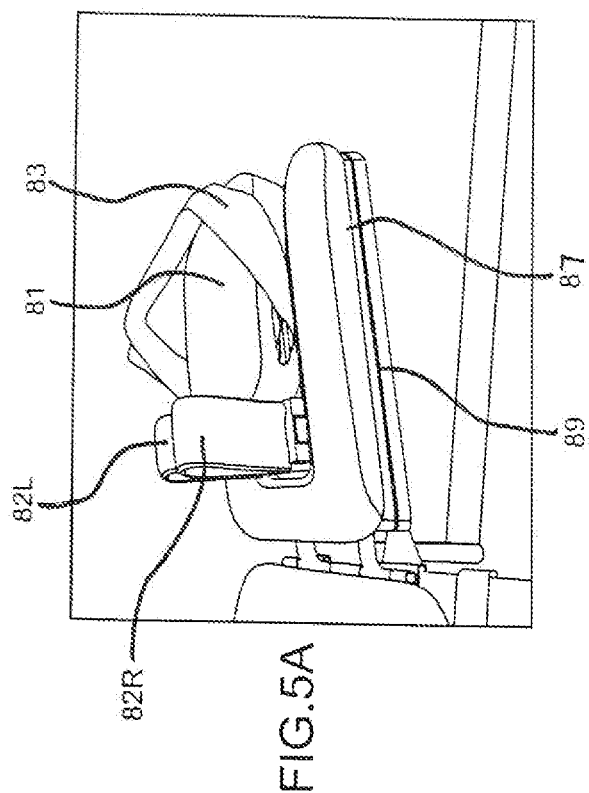
FIG. 5A is a perspective view of a padded head support of are adjustable cervical piece, being in a first position that is proximal to the chest section.
Figure 5C:
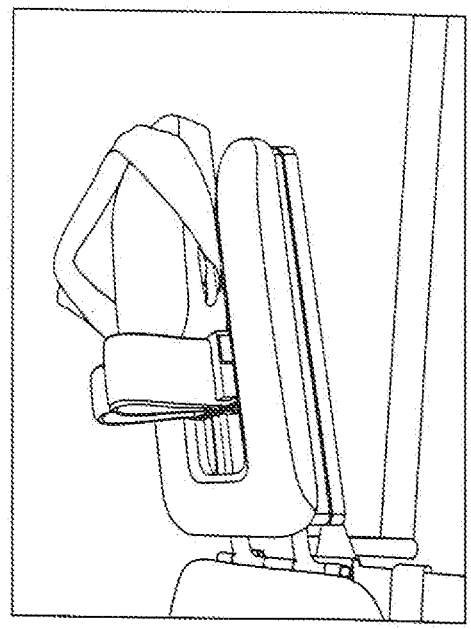
FIG. 5C is the perspective view of the padded head support of FIG. 5A, adjusted to provide traction, and being between the first and second positions.
Figure 5F:
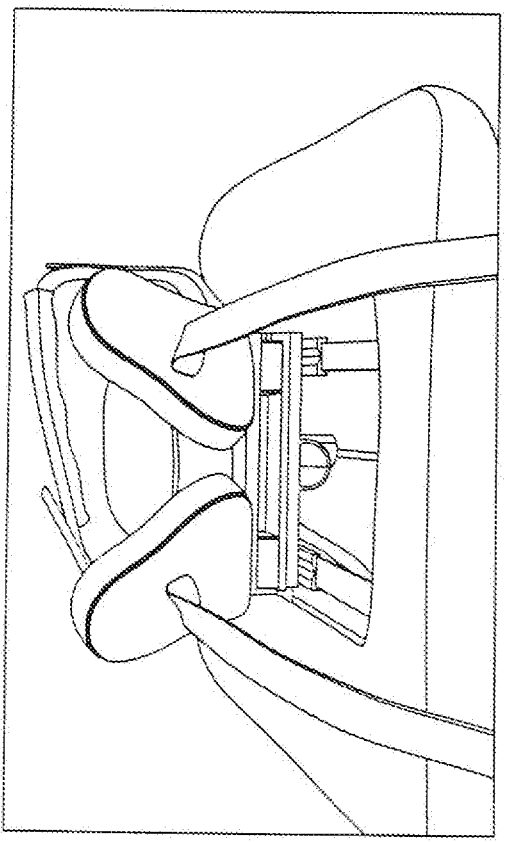
FIG. 5F is a side view of the cervical section with padded head support of FIG. 5B.
Figure 5E:
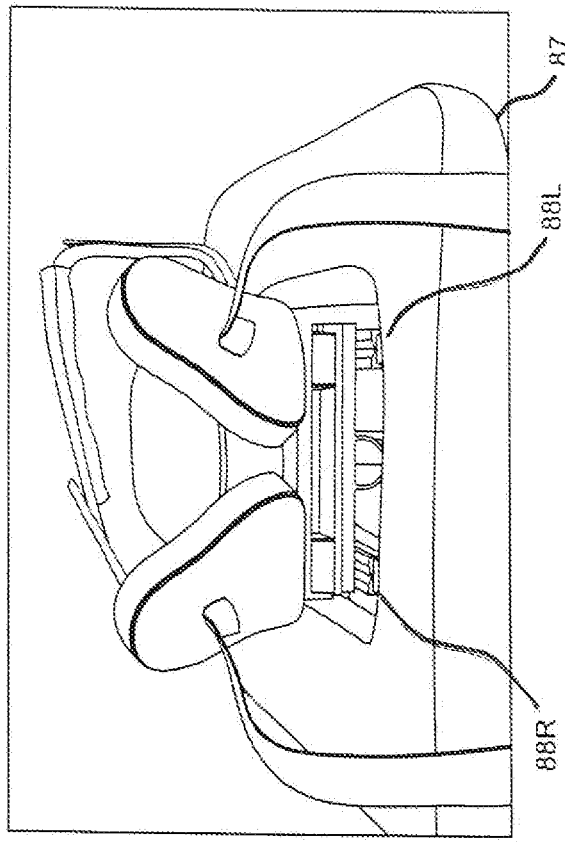
FIG. 5E is a side view of the cervical section with padded head support of FIG. 5C.
Figure 5G:
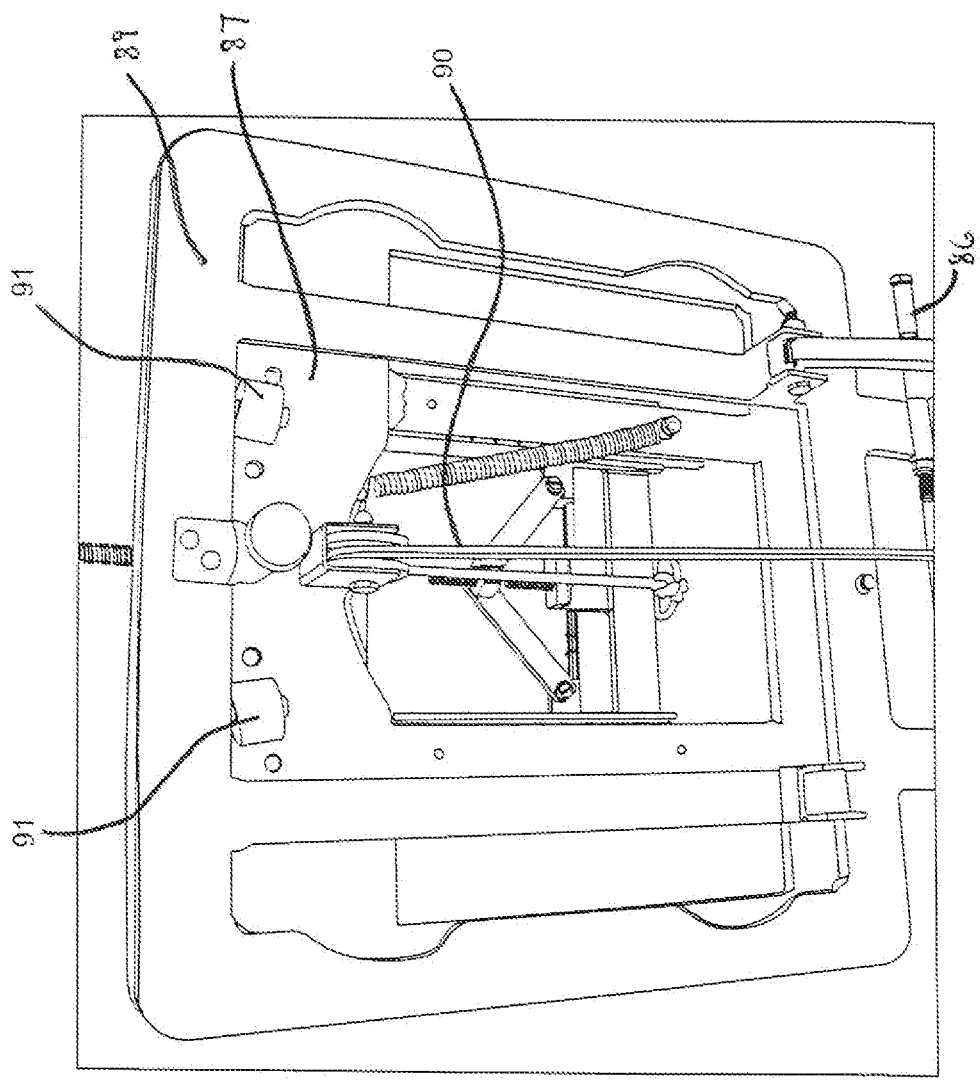
FIG. 5G is a bottom view of the cervical section.
Figure 5J:
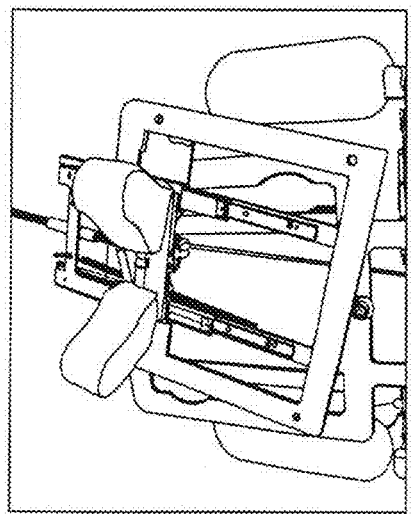
FIG. 5J is the top view of FIG. 5I, but with the head support and neck bolsters moved by the cable/rope and pulley system to be in a position distal to the chest section.
Figure 5I:
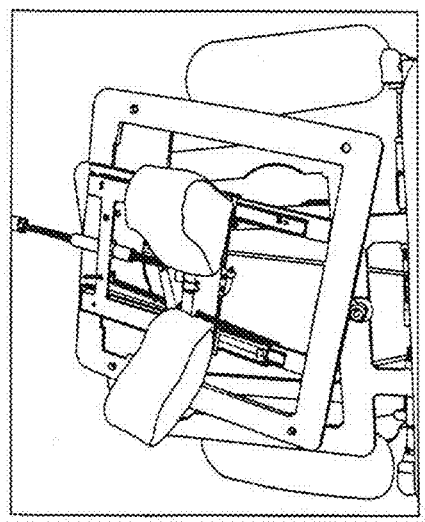
FIG. 5I is the top view of FIG. 5H, but with the head support and neck bolsters moved by the cable/rope and pulley system to be in a position less proximal to the chest section.
Figure 5H:
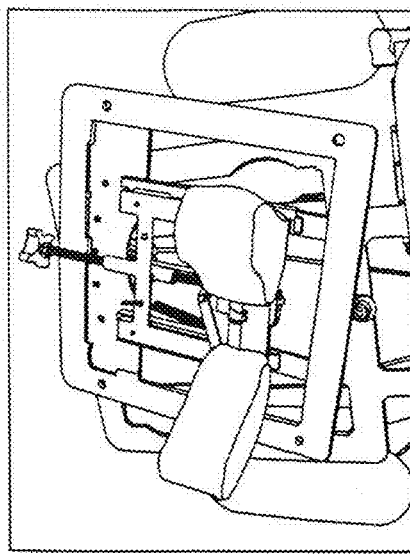
FIG. 5H is top view of the cervical section of FIG. 5G, with the padding removed to expose the scissors mechanism for the neck bolsters, and with the head support and neck bolsters shown in a position proximal to the chest section, and with the neck bolsters shown substantially separated.
Figure 5L:
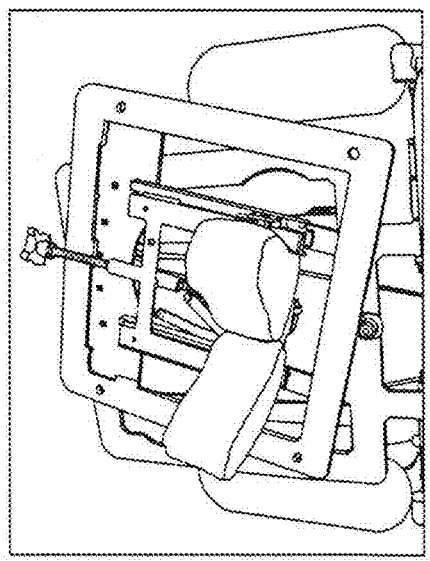
FIG. 5L is the top view of FIG. 5K, but with the neck bolsters moved by the scissors mechanism to be touching each other.
Figure 5K:
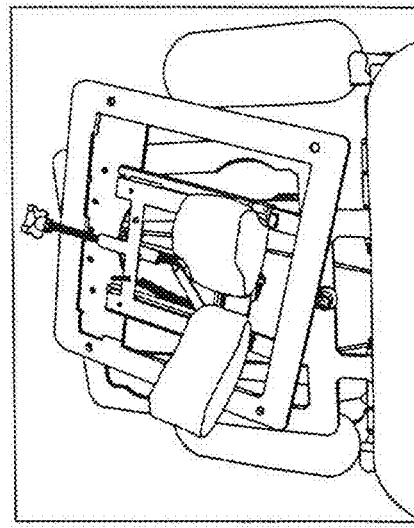
FIG. 5K is the top view of FIG. 5H, but with the neck bolsters moved by the scissors mechanism to be closer together.

As seen in FIGS. 5E and 5F, the head support 81 may be mounted in tracks 88L and 88R of a tray 87 that is mounted to a plate 89 of the cervical section, which is pivotally mounted to the table frame 50 using hinges. This sliding arrangement may be used to facilitate linear axial traction. The padded head support 81 may be translatable in the tracks 88L, and 88R relative to tray 87, by using a traction cable or rope 90 that runs along a pulley system attached to the mechanisms of the head support 81, and which runs along the length of the table 10 to the foot of the table. This innovation ensures proper and comfortable patient positioning, and ensures a minimal need fix the patient to change positions to participate in other therapies that are disclosed herein.

Figure 6A:
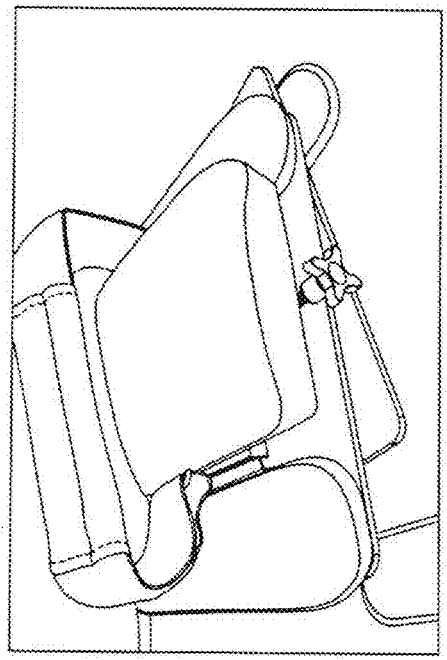
FIG. 6A is a reverse side view of the cervical section of FIG. 5A, with the cervical section being in a neutral position and not providing any lateral traction.
Figure 6B:
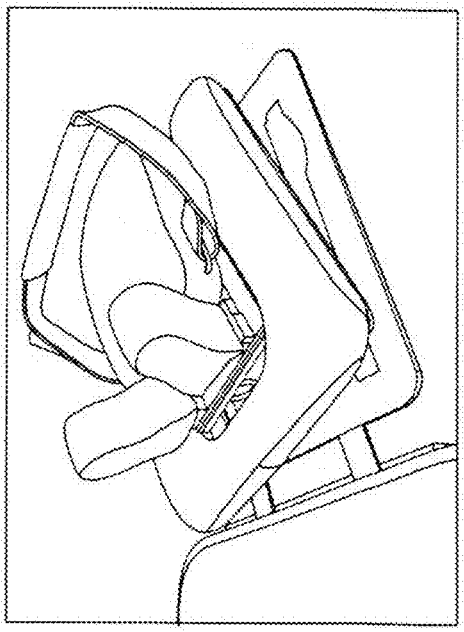
FIG. 6B is the side view of the cervical section of FIG. 6A, but with the tray of the cervical section having been rotated to provide lateral traction, and apply tension to the patient's right side.
Figure 6C:
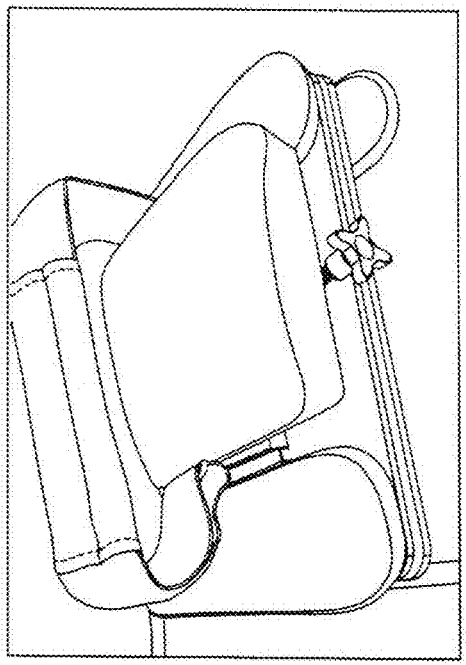
FIG. 6C is the side view of the cervical section of FIG. 6A, but with the tray of the cervical section having been rotated to provide lateral traction, and apply tension to the patient's left side.
Figure 6D:
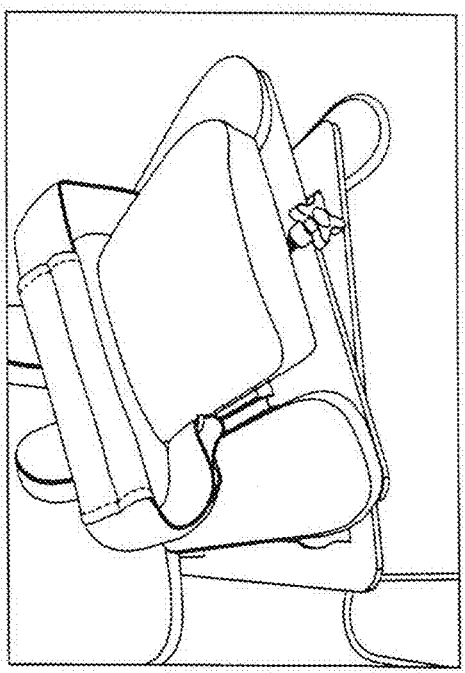
FIG. 6D is a perspective view of the arrangement of FIG. 6C.

Another unique innovation relating to the cervical section 80 is derived from the tray 87 being pivotally mounted to the plate 89 to permit lateral rotation of the padded head support 81 of at least 15 to 30 degrees from each side of center to facilitate lateral cervical spinal decompression (FIGS. 6A-6C). The tray 87 and padded head support 81 may swivel from side-to-side on roller wheels 91 (FIG. 5G) located on the plate 89, which acts as a platform. A spring loaded knob/pin 92 under the plate 89 (FIG. 5D) may lock the tray 87 relative to the plate, once it is positioned in the desired position. This innovation is intended to treat specifically identified patient conditions such as unilateral radiculopathy, neck pain, arm pain and postural abnormalities such as scoliosis.

Figure 4B:
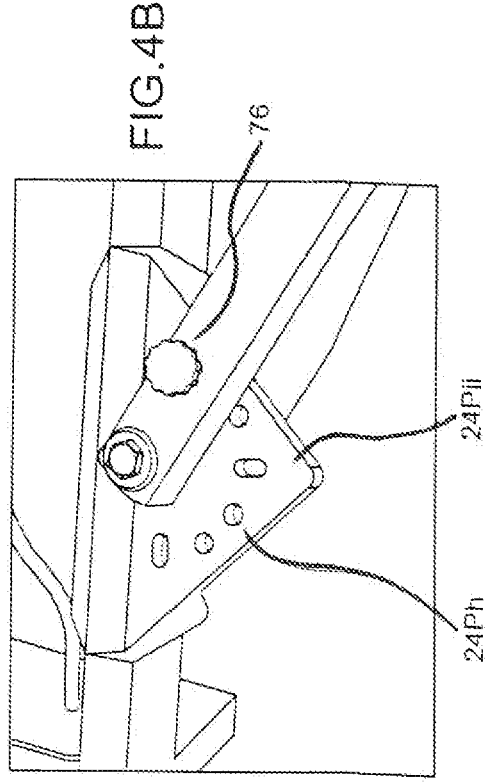
FIG. 4B is the platform arm of FIG. 2 with it capability of being rotation laterally into multiple different positions using a second embodiment of a plate and a spring biased locking pin.
Figure 2:
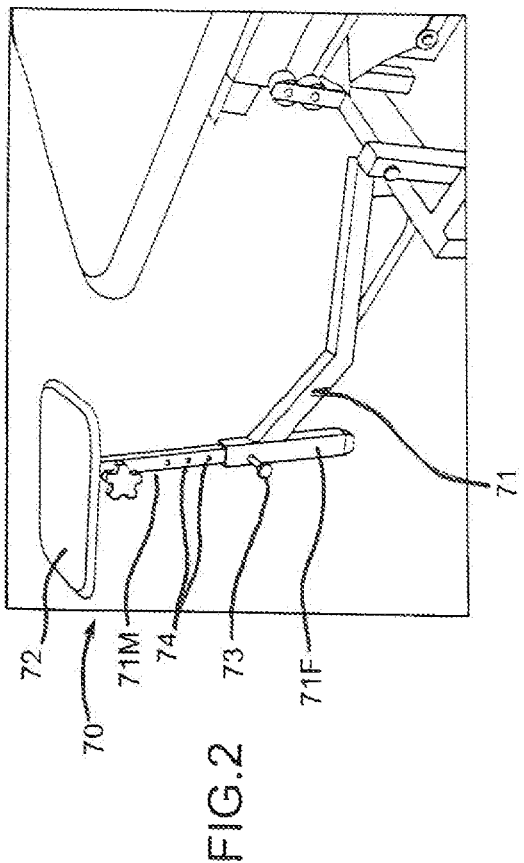
FIG. 2 is a perspective view focusing on the traction machine platform at the foot of the table, with it being shown in a first position.
Figure 4A:
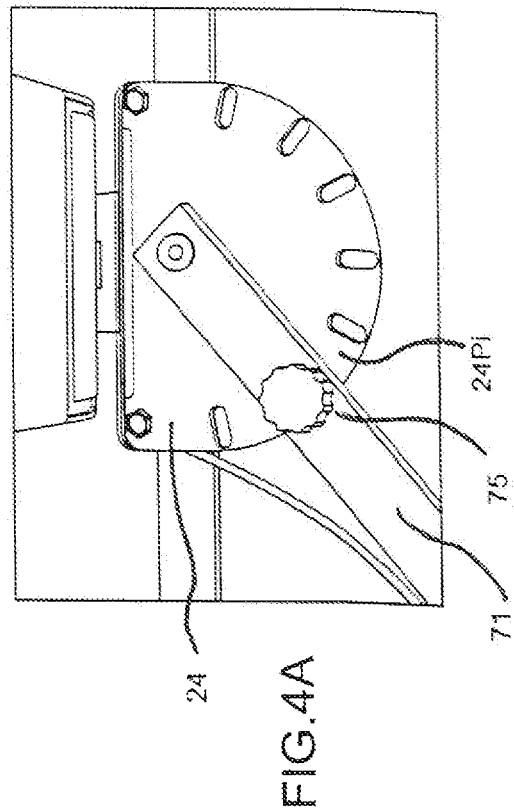
FIG. 4A is the platform arm of FIG. 2 with it capability of being rotation laterally into multiple different positions using a first embodiment of a plate and tension knob.

The traction platform 70 (FIGS. 1A and 2) may comprise a curved or bent arm 71 that may be pivotally attached to the table frame 50 at the end of the frame being opposite to that which the cervical section 80 is mounted. The free end of the arm 71 may comprise a tube-like member 71F having a circular, rectangular, or other cross-sectional shape. A female opening in member 71F may slidably receive a corresponding male-shaped member 71M upon which is mounted a platform member 72. The height of the platform member 72 relative to the table is adjustable through a locking pin 73 in the member 71F being received in one of a series of holes 74 in the male-shaped member 71M. The traction platform 70 may be laterally adjustable, relative to a centerline running along the axial length of the table, using either a tension knob 75 on the arm 71 of the platform, and being securable to a plate 24Pi that is attached to the cross-member 24 of the base frame 20 (FIG. 4A), or using a locking pin 76 on the platform being received in one of a plurality of holes 24Ph in the plate 24Pii (FIG. 4B). This lateral and vertical adjustability in the traction platform 70 may provide a suitable platform to hold a traction machine at a convenient location to thereby apply traction to the patient.

Figure 9:
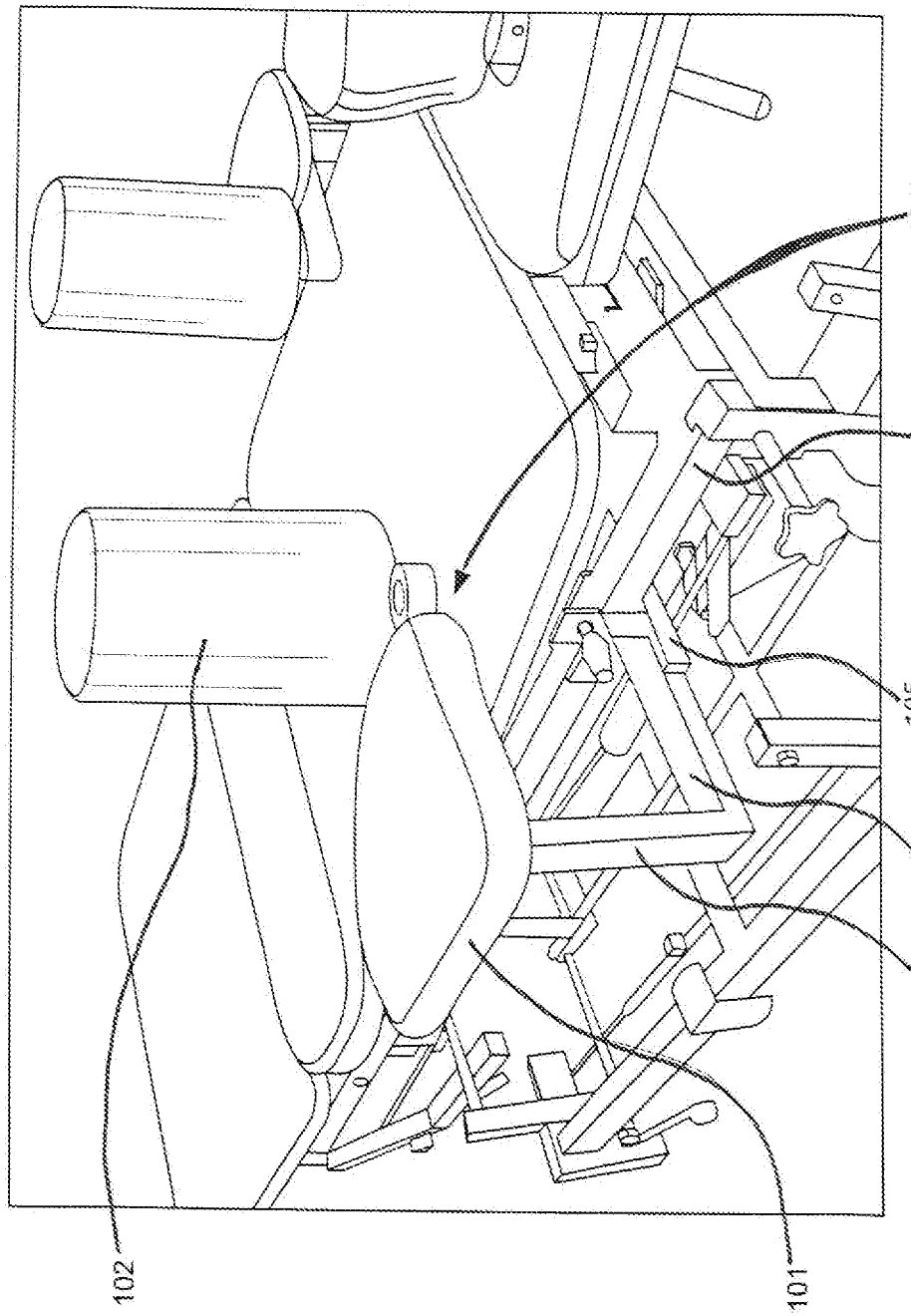
FIG. 9 is an enlarged perspective view of the multi-function treatment table of FIG. 1, showing features of the bolstering and arm rest system.
Figure 9A:
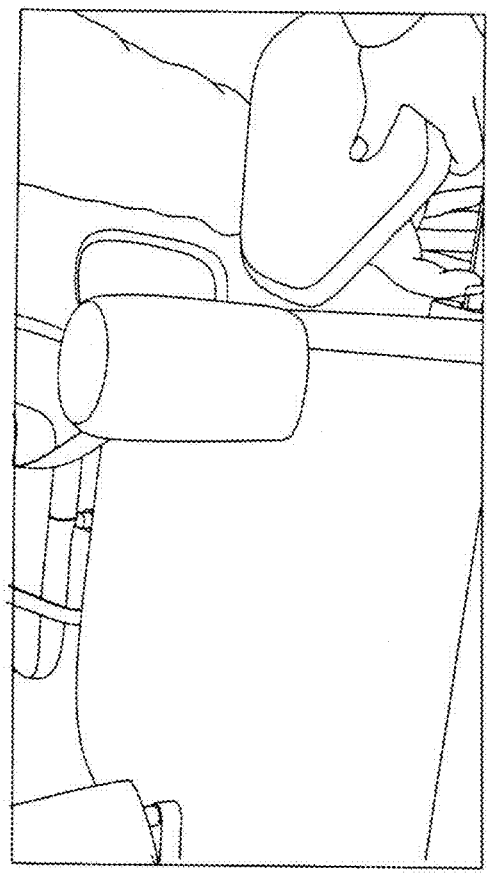
FIG. 9A is the bolstering and arm rest system of FIG. 9 having been adjusted to be in a position more distal from a patient's head.
Figure 9B:
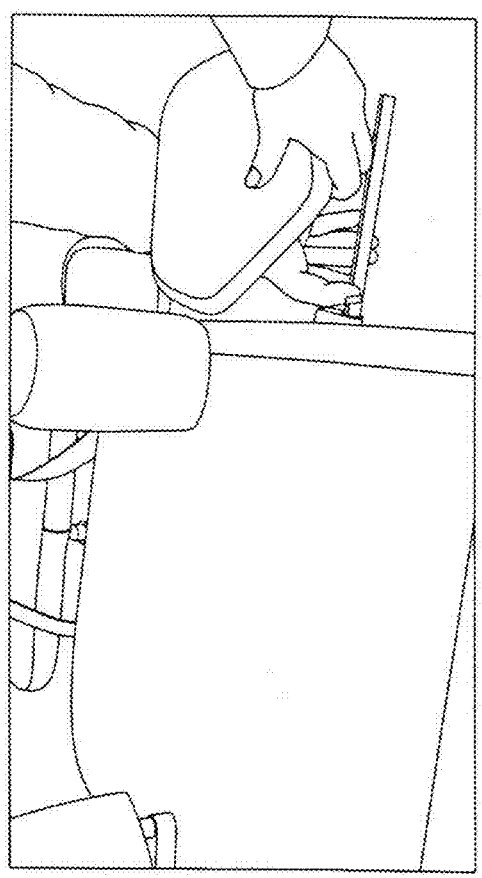
FIG. 9B is the bolstering and arm rest system of FIG. 9 having been adjusted to be in a position more proximal to a patient's head.
Figure 10:
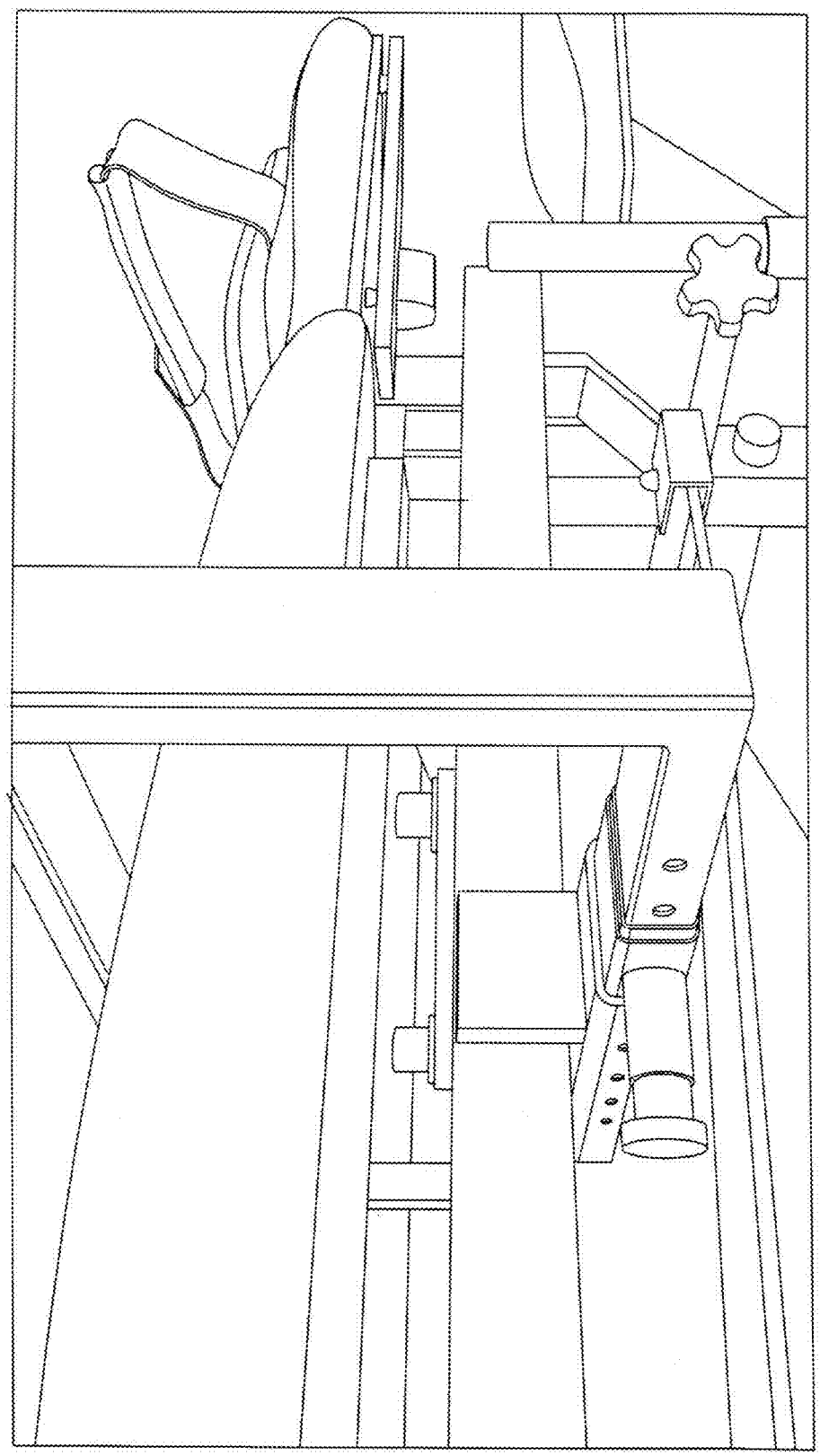
FIG. 10 is a side perspective view of the bolstering and arm rest system of FIG. 9.
Figure 11:
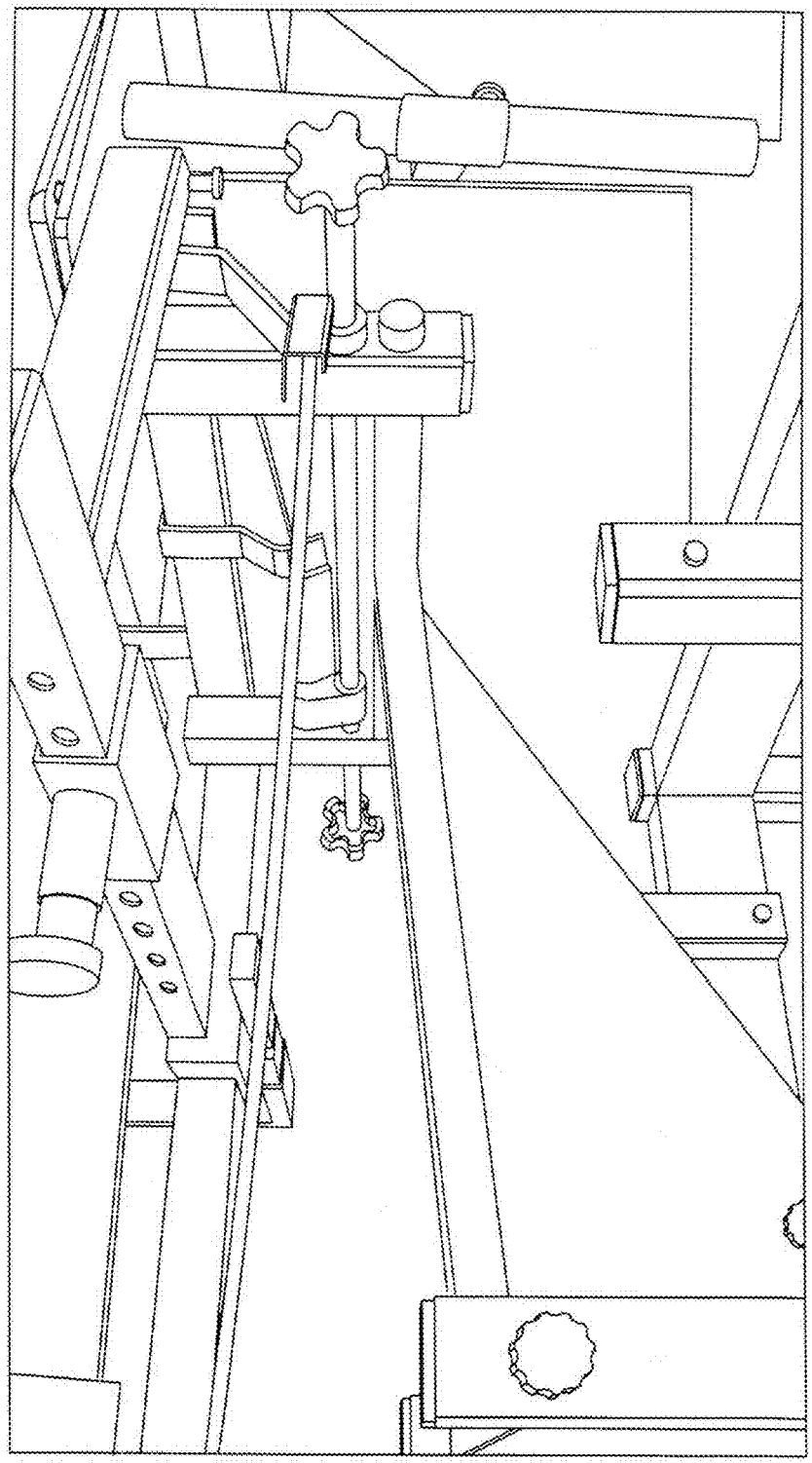
FIG. 11 is a perspective view looking up at the underside of the table, to show adjustable attachment details of the bolstering and arm rest system.

The table 10 may also include an adjustable arm rest system 100 (FIG. 9). It is designed with a padded arm support platform 101, from which a cylindrical arm bolster 102 may protrude upward therefrom, for each of the left arm and right arm of the patient. The arm support platform 101 may accommodate vertical height adjustments through its attachment to male/female members similar to the vertical adjustability of the traction platform 70. The vertical support member 103 for the arm support platform 101 may be fixed to a horizontal member 104. Horizontal member 104 may be slidably received in a bracket 105 that is itself slidably mounted to the side member 51 of table frame 50. This permits adjustment of the underarm bolster system both cephalically and caudally (toward the head and toward the foot—FIGS. 9A-9B) to account for different patient heights, as well as adjustments medially and laterally (FIG. 10). The adjustment may preferably be in 1 inch increments to account for different patient widths, through the use, again, of spring biased locking pins. The armrests may adjust sufficiently for supine patient positioning to widen so as to make it comfortable and suitable for treatments where arms outstretched is a desired positioning (acupuncture, massage therapy postures, spinal decompression postures).

Each of the body support sections—chest section 60, lumbar section 61, and leg section 62—may be split into a fixed lower portion and a removable upper padded portion, where the removable upper padded portion may be replaceable with a treatment module being secured in an opening in the fixed lower section. Alternatively any of the chest, lumbar and leg sections may be integrally formed, or the body support may comprise a single table member. One example of the treatment module may comprise hot and cold compresses, which may be traditional hot and cold compresses (hot water or ice) or may comprise electrically powered heating and cooling.

Another treatment module may comprise a laser for laser therapy in treating skin conditions, and/or joint or spinal problems. As an example, an enhanced spinal decompression apparatus 110 is disclosed for non-surgical spinal decompression that combines the benefits of vertical and lateral traction, and enhanced laser treatment protocols to treat soft tissue damage and herniated disks. The laser enhanced spinal decompression apparatus 110 may comprise a first linear actuator 111 and a second linear actuator 112 (FIG. 12A) being usable to position a laser along an X direction and along a Y direction, wherein the laser and the first and second linear actuators are mounted within a box 114 (FIG. 13). The laser and associated equipment may all be contained within the metal enclosure of box 114 to prevent light from escaping and to protect against accidental damage to the equipment.

There are many different types of linear actuators, any one of which may be suitably adapted for use within the enclosure 114 to drive the laser. There are mechanical actuator types, such as ball & screw (worm gear drive shaft); wheel and axle; hoist; winch; rack & pinion; chain drive; belt drive; and cam-types, as well as hydraulic actuator types, pneumatic actuators, piezoelectric actuators, and electro-mechanical actuators. To be exemplary, the linear actuators picture herein comprise worm-drive type actuators with a stepper motor.

Figure 12B:
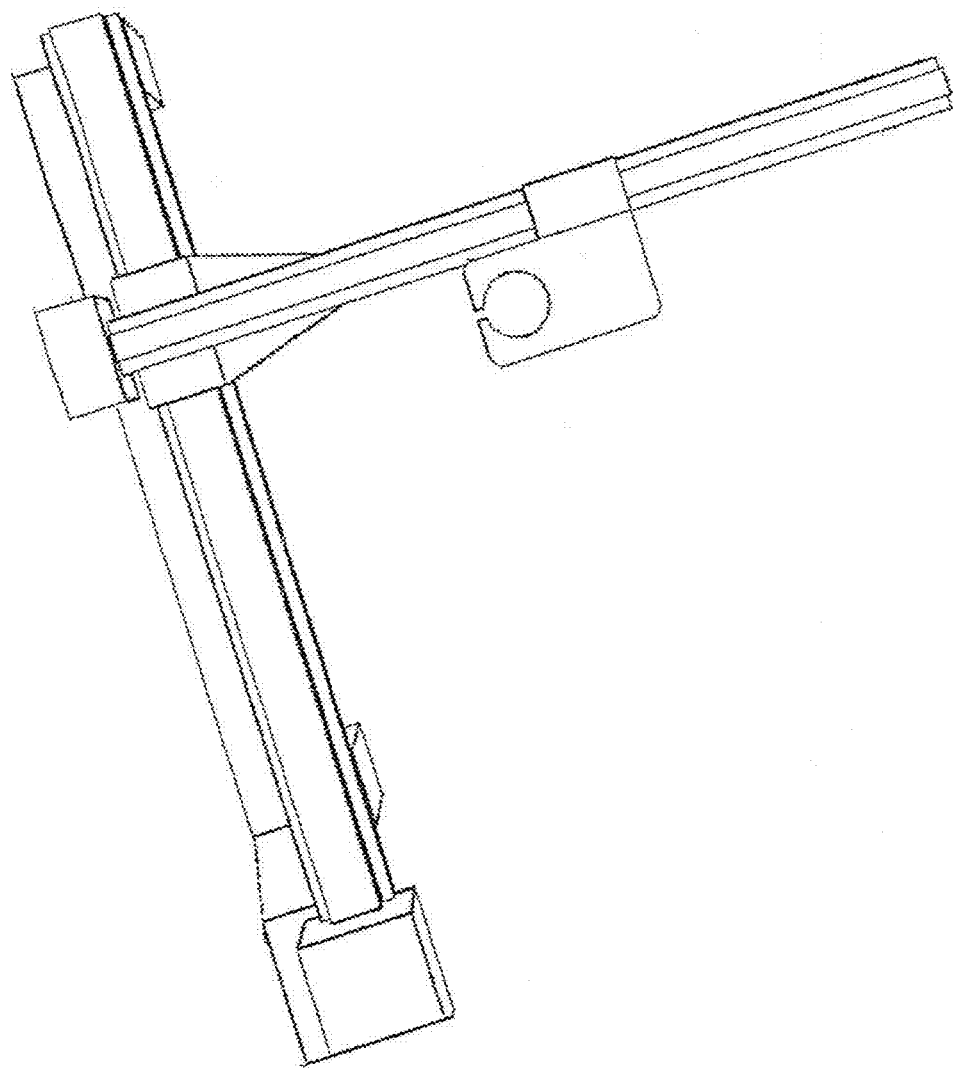
FIG. 12B is a side perspective view of the partial assembly of FIG. 12A.
Figure 13A:
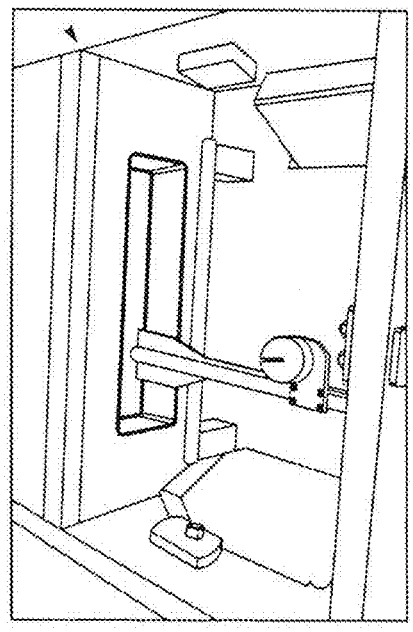
FIG. 13A is a side perspective view of the two assembled linear actuators of FIG. 12A, after being mounted in the laser automation box/enclosure.
Figure 13B:
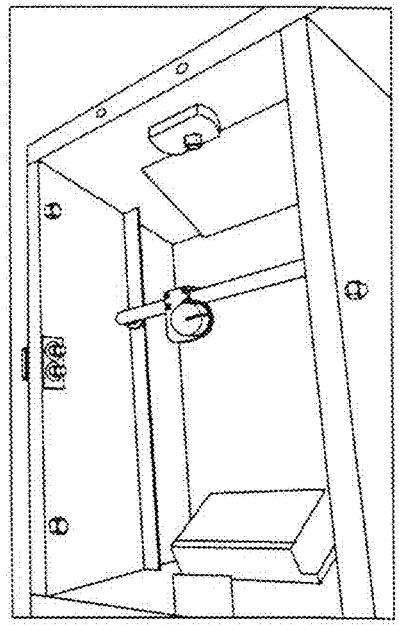
FIG. 13B is a reverse side perspective view of the laser automation box/enclosure of FIG. 12A.
Figure 13C:
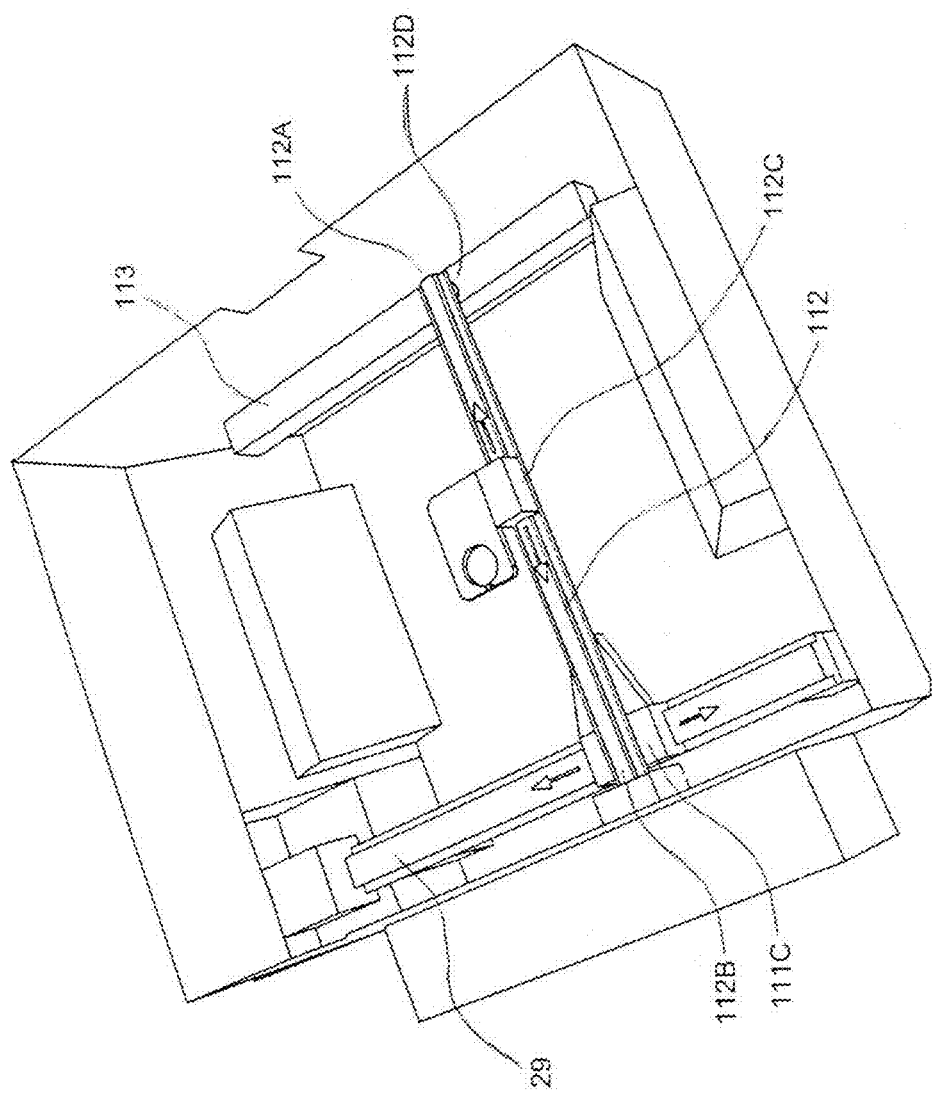
FIG. 13C is an angled perspective view of the laser automation box/enclosure of FIG. 12A.

FIGS. 12A and 12B illustrate the two worm drive actuators sitting on a fixture prior to installation within the enclosure box 114, and being oriented orthogonally with respect to each other. FIGS. 13A and 13B show side perspective views of the actuators after installation within the enclosure box 114, which is mounted to the treatment table frame. FIG. 13C shows an angled perspective view into the box 114, where a metal plate is secured to a member known as a "car" or "carriage" 112C, and which is driven by the Y-axis worm drive actuator boom 112, and is thereby drivable in the positive/negative Y directions. The second end 112B of the Y-axis worm drive actuator boom 112 may be secured to the "carriage" 111C of the X-drive actuator 111, which, when actuated, may thereby cause the Y-axis worm drive actuator boom 112 to translate in the positive/negative X directions. A first end 112A of the Y-axis worm drive actuator boom 112 may have a plastic interface part secured thereto, which may be a disk 112D that may be made of a crystalline plastic known as Delrin®, and which may travel along a fixed beam 113 that is secured to a sidewall of the box 114. This arrangement permits the first end of the Y-axis worm drive actuator boom 112 to smoothly glide along the beam and offer support to the boom, without resulting in excessive friction.

Figure 13D:
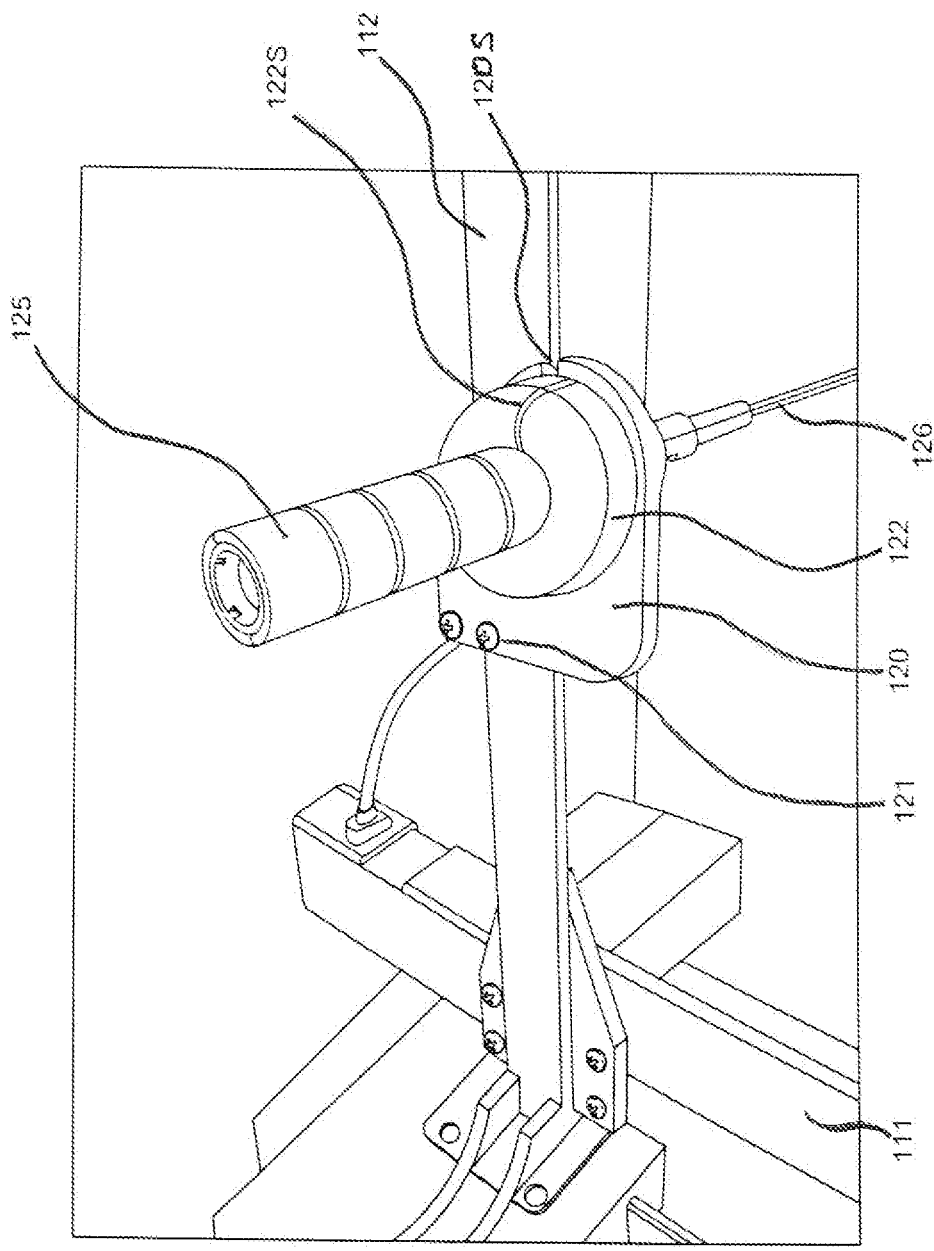
FIG. 13D is an enlarged view of the laser hand-piece of the current invention being releasably received into the corresponding retaining ring that is secured to an aluminum tray attached to the X-axis linear actuator.

As seen in FIG. 13D, the Y-axis worm drive actuator 112 may have a plate 120 secured to the actuator boom "car" 112C, which may be a metal plate that is secured using mechanical fasteners such as screws 121. The plate 120 may cantilever away from the actuator 112 to provide unrestricted support for a laser holder 122 that may releasably receive the laser hand-piece 125 with its associated fiber optic cable 126. The laser holder 122 may be cylinder-shaped member with a concave center portion to receive a corresponding shape of the laser hand-piece 125. Both the plate 120 and the laser holder 122 may have a respective slot 120S and 122S therein to accommodate the fiber optic cable 126 that connects the laser hand-piece 125 with the control module. This permits the laser hand-piece 125 to be easily seated or removed without disconnecting the cables. A detent or snap ring may be used to releasably retain the laser hand-piece 125 within the laser holder 122.

Figure 13E:
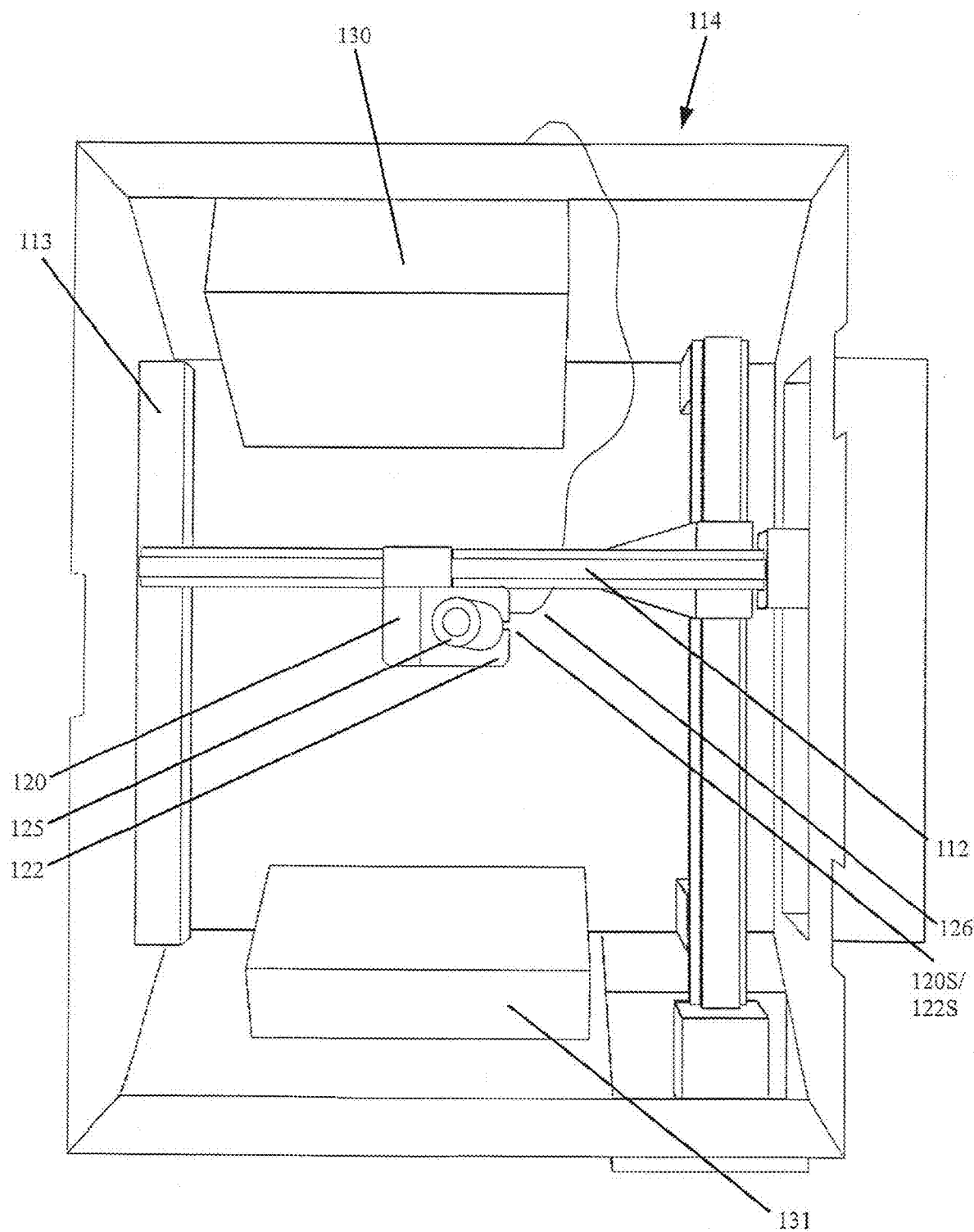
FIG. 13E is a top perspective view looking into the opening of the laser automation box/enclosure.

Each of the actuators 111 and 112 may have an encoder to determine the distance of travel by each of the respective cars, 111C and 112C, so the system may accurately determine or sense the portion of the laser through the position of each car. Software for driving the lasers with the actuator cars may work in conjunction with the encoders, and may contain safety protocols that may sense an unexpected stoppage in motion, which will trigger a relay or switch to shut the system down, including power to the laser. This may serve to prevent overheating of the target area of the patient by the class 4 laser, or damage to the system. In addition, secondary position sensing may be provided at the furthest limits of travel in both directions for each of the two linear actuators the using limit switches or proximity sensors, which may serve to calibrate the system or serve as a primary system stop to prevent over travel and damage to the actuators. A hard stop may provide a backup, whereby contact of the actuator carriage with the hard stop due to failure of the encoder or sensor may result in an over-current condition that is detected by the controller. In FIG. 13E, the green colored controller circuit board 130 is positioned within the upper portion of enclosure 114, while the power supply 131 is positioned within the lower portion of the box 114, and may be protected by a metal grate.

Figure 14A:
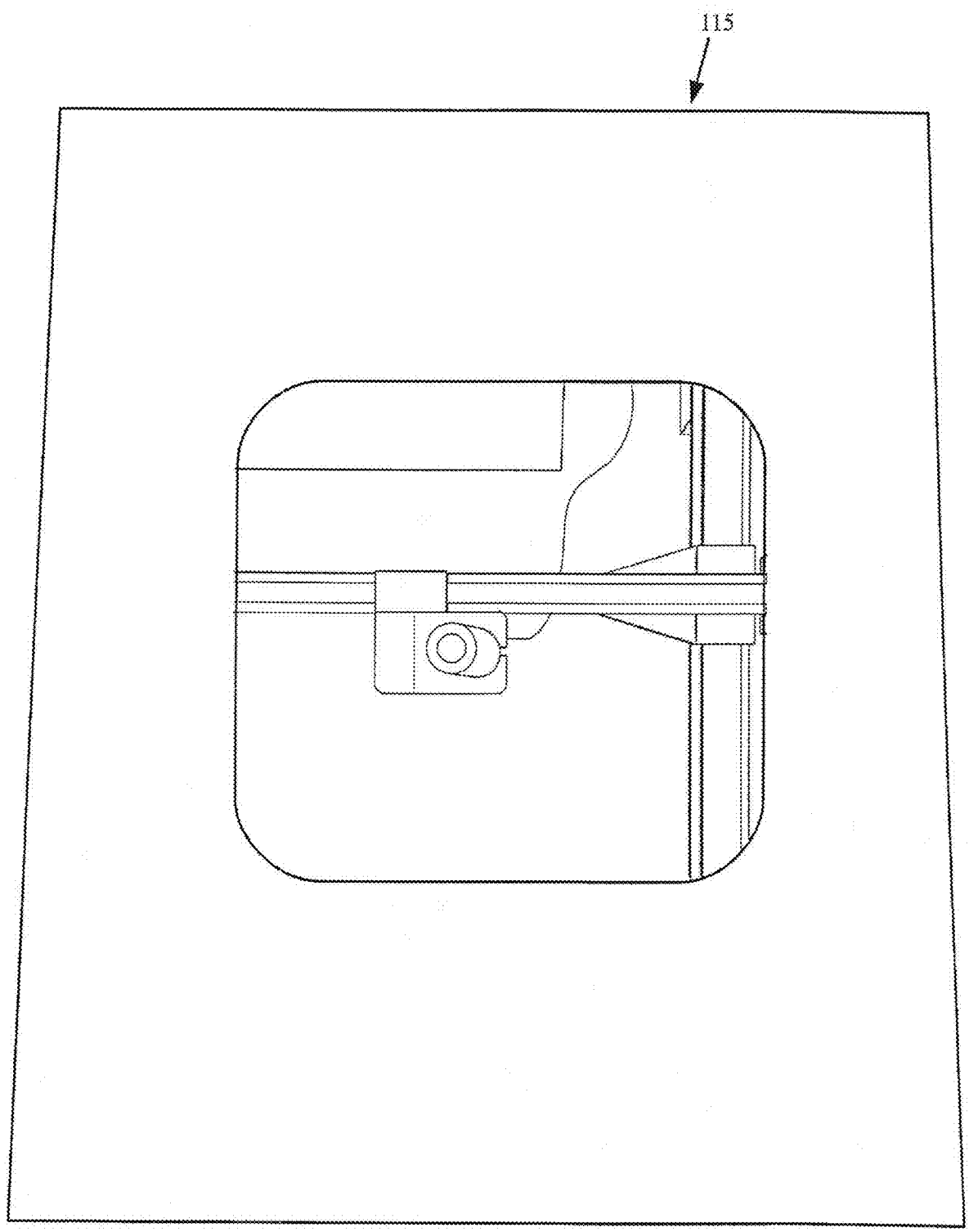
FIG. 14A is a top perspective view of the enclosure of FIG. 13F, after installation within the treatment table of the current invention, and after installing the protective cushioned gland around the perimeter of the top of the box, for sealing against a patient.

FIG. 14A shows the enclosure 114 of FIG. 13E being covered by a cushioned gland 115 around a top perimeter of the box to create a seal against a patients' skin surface to thereby prevent or reduce laser light from being transmitted about the room by escaping therefrom. Additional proximity sensors, which are known in the art, may also be used near the opening in the box 114 to detect the presence of a torso on the center pad (over the laser box) to provide a safety shut off to the laser to avoid potential eye damage when the laser box opening, is not covered during treatment being provide by the laser. The laser treatment provided by this enhanced spinal decompression apparatus may comprise the laser emitting specialized laser light upon a spine of a patient, with the laser translating in the X and Y directions and being directed to emit light according to a specific treatment protocol. The laser may emit a range of different wavelengths, however in one embodiment, a wavelength of 940 nm+/−15 nm is used, and may provide a depth of penetration on the order of approximately 5 millimeters on a low power setting for treatment of dermatological conditions and scarring, and a depth of approximately 10 cm on full power for treatment of deeper spinal and joint conditions. The laser may be capable of delivering 620 joules per minute of energy.

The laser enhanced spinal decompression apparatus may comprise the controller 130 interfacing with software to permit any number of specialized treatment protocols to be pre-programmed and/or to be customizable for individual patients. In particular, an interface application program (see screenshots in FIGS. 15A-15E) that allows a practitioner to initiate laser treatments from the screen of a PC running Windows (or alternatively initiated from an existing portable control device that mounts to a docking port on the table), may coordinate with a commercially available controller program, such as "Gallil Tools," which is available from Galin Motion Control of Rocklin, Calif. (see www.galilmc.com/products/galiltools.php, the disclosures of which are incorporated herein by reference).

Figure 19:
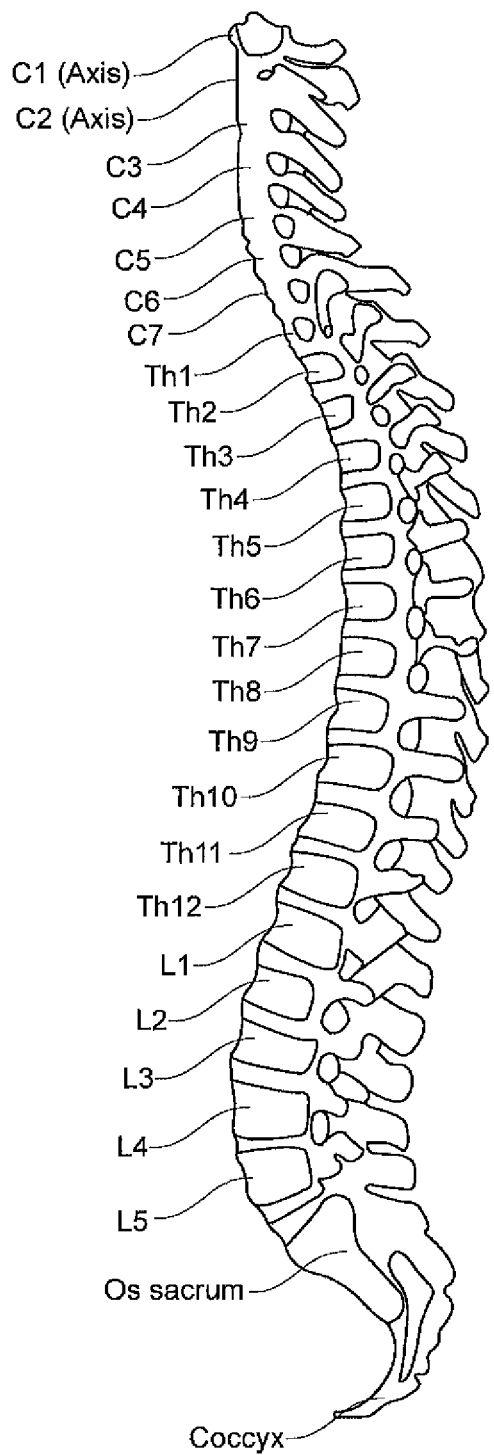
FIG. 19 is a generic illustration of the division of segments in a human spine.
Figure 20:
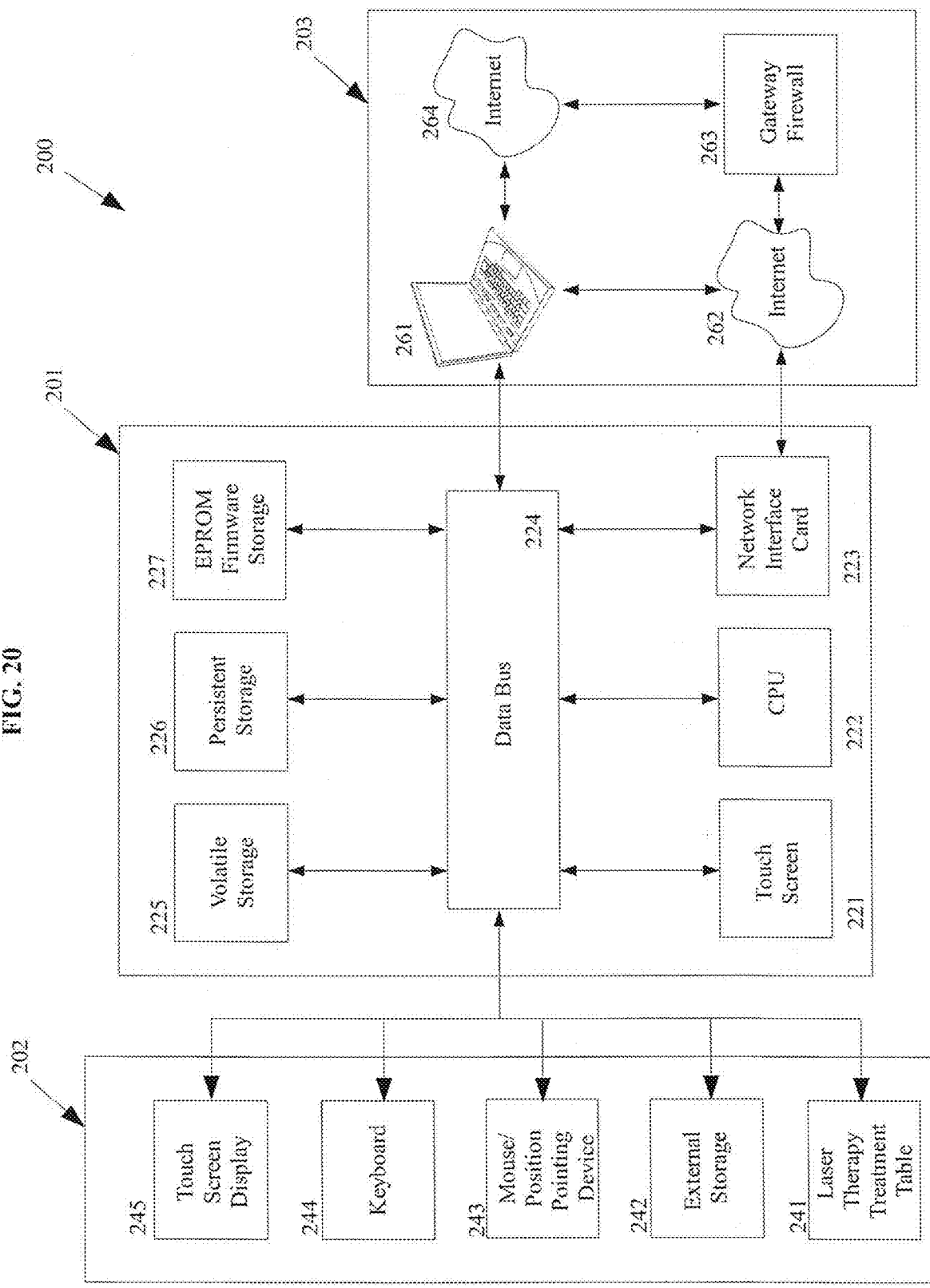
FIG. 20 is a schematic of an exemplary computing unit being capable of running the software of the current invention and interacting with other computers over the internet, and with external peripherals, including specialized equipment of the treatment table of the current invention.

The linear actuators may preferably provide the laser with a range of motion for the treatment protocol comprising travel of approximately 4 to 8 inches or even more to each side of a center of a patient's spine (or a particular joint), and a range of motion for travel up and down a patient's spine to cover spinal disks from L1 to S1 (see FIG. 19). The optimal angle for emission of the laser is, in part, controlled by the laser's specially designed lens, which diverges the beam at an optimal angle while maintaining uniform dosage intensity across the beam, and is designed by Biolase Technologies, Included is an optional mechanism by which the laser hand-piece can be automatically angled at 45 degrees to the treatment surface which can be maintained within or beyond the travel range.

The laser enhanced spinal decompression apparatus may also comprise one or more sensors, being optical sensors, temperature sensors, pressure sensors, and/or motion sensors. The sensor may provide useful data during treatment. For example, one or more temperature sensors may be used for thermographic imaging to thereby monitor tissue temperatures to achieve an optimal dosage by the laser.

Figure 14B:
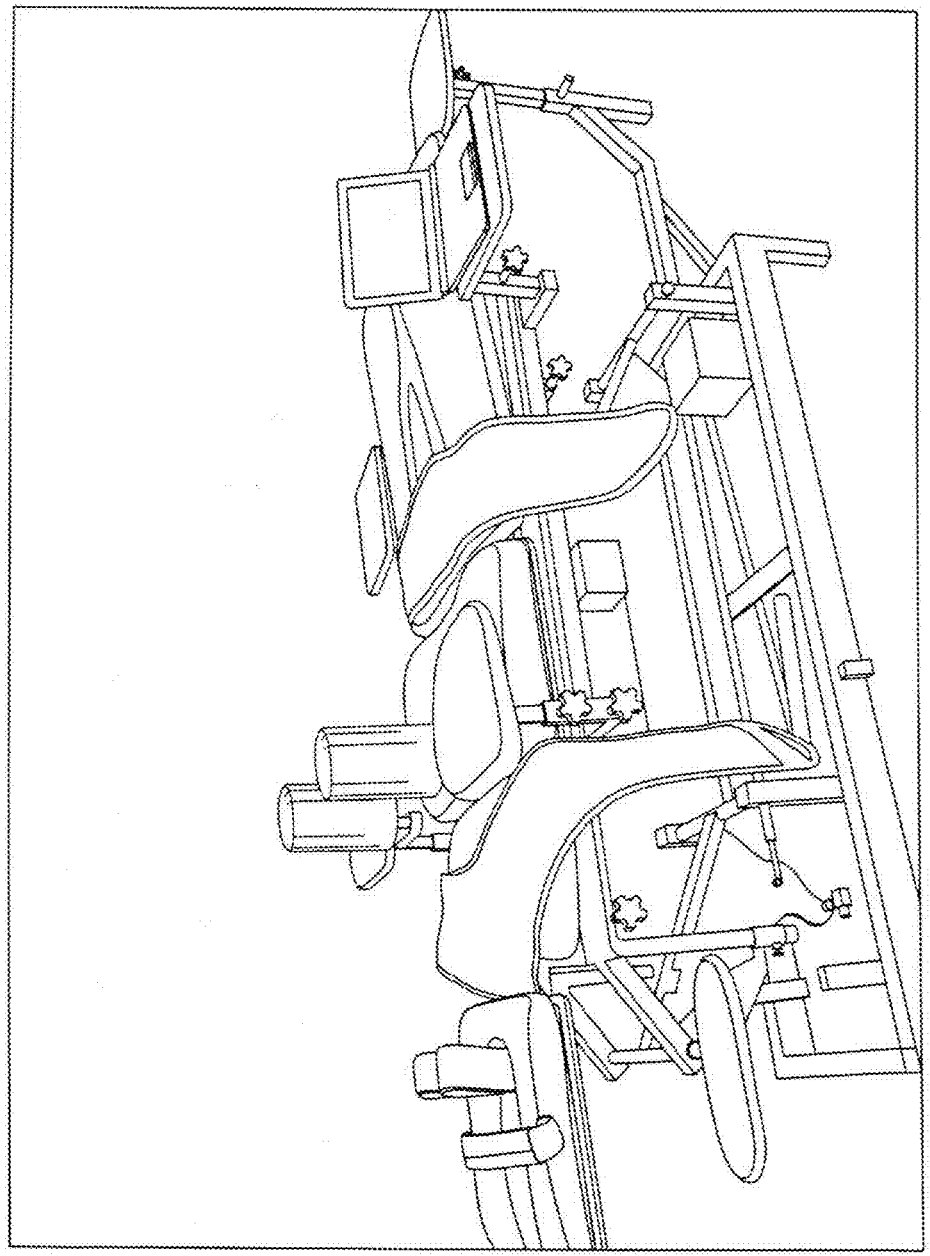
FIG. 14B is a perspective view of a treatment table of the current invention, utilizing a laser treatment module/box in a lumbar, with the electrical drive circuitry for the laser and the linear actuators being coupled to a laptop computer through a motion controller, and being responsive to instructions from software running on the computer.
Figure 14C:
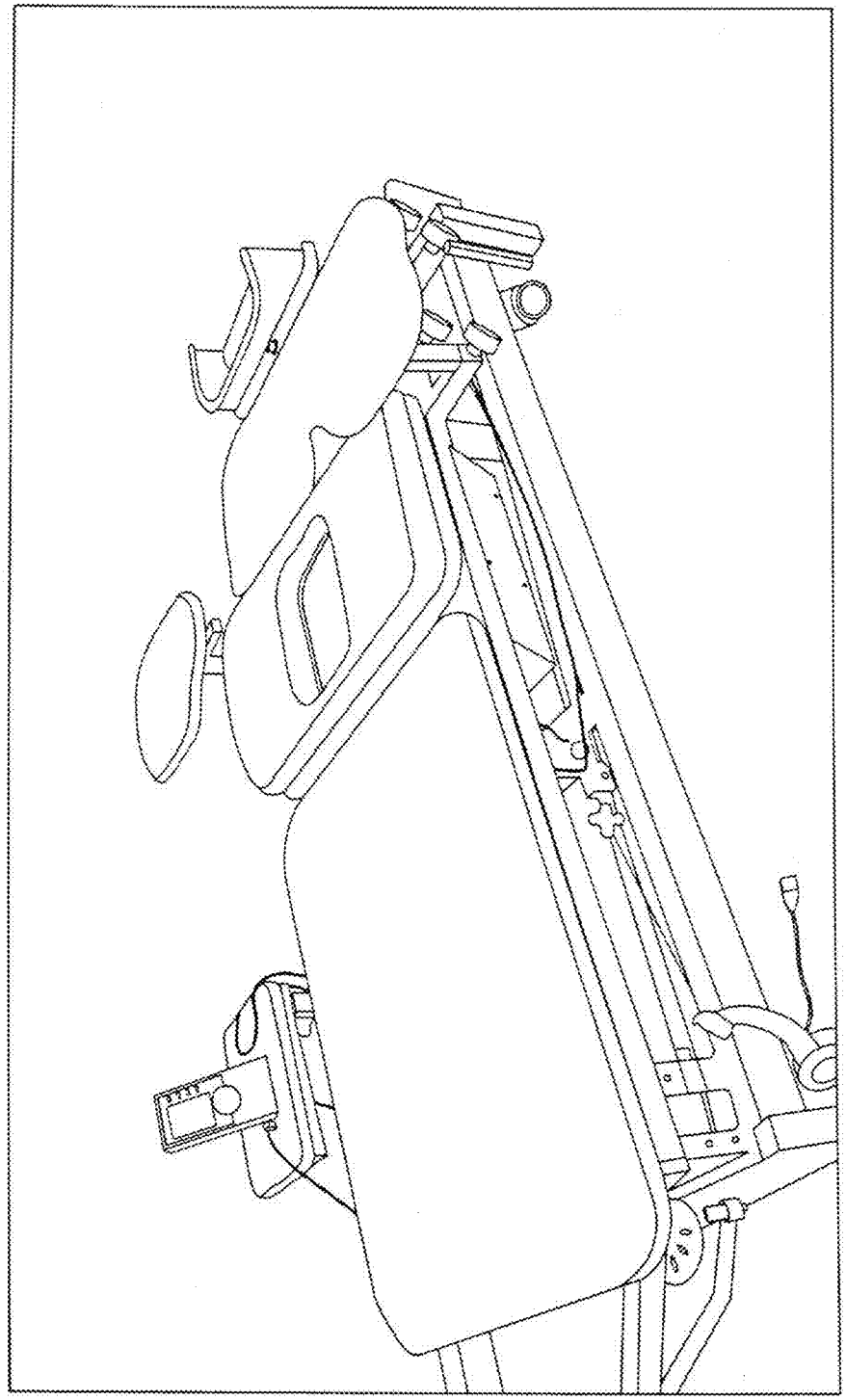
FIG. 14C is a reverse perspective view of the treatment table of FIG. 14B.
Figure 14D:
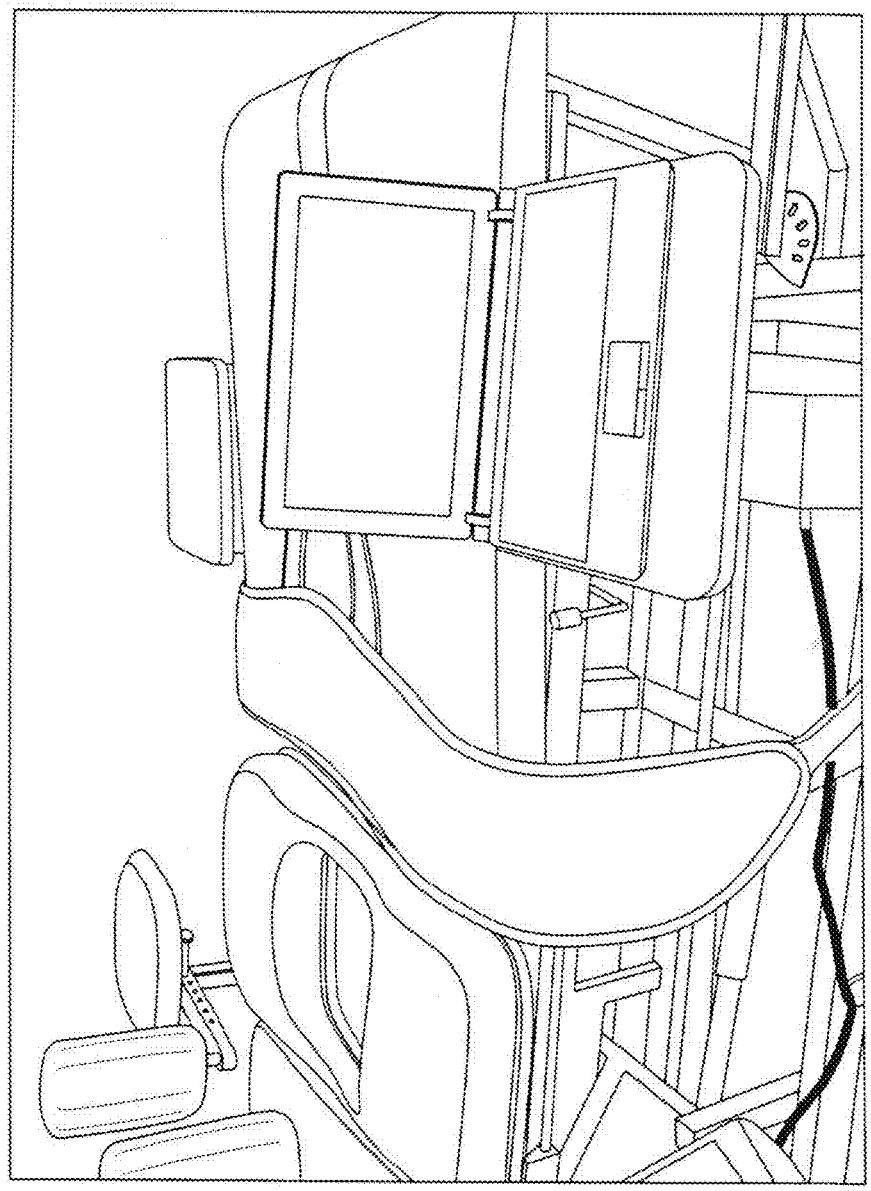
FIG. 14D is the treatment table of FIG. 14B, but enlarged to show the gland above the laser treatment module/box and the opening therein, as well as the laptop computer being coupled using a USB cable to command the treatment protocols that are performable by the module.
Figure 15B:
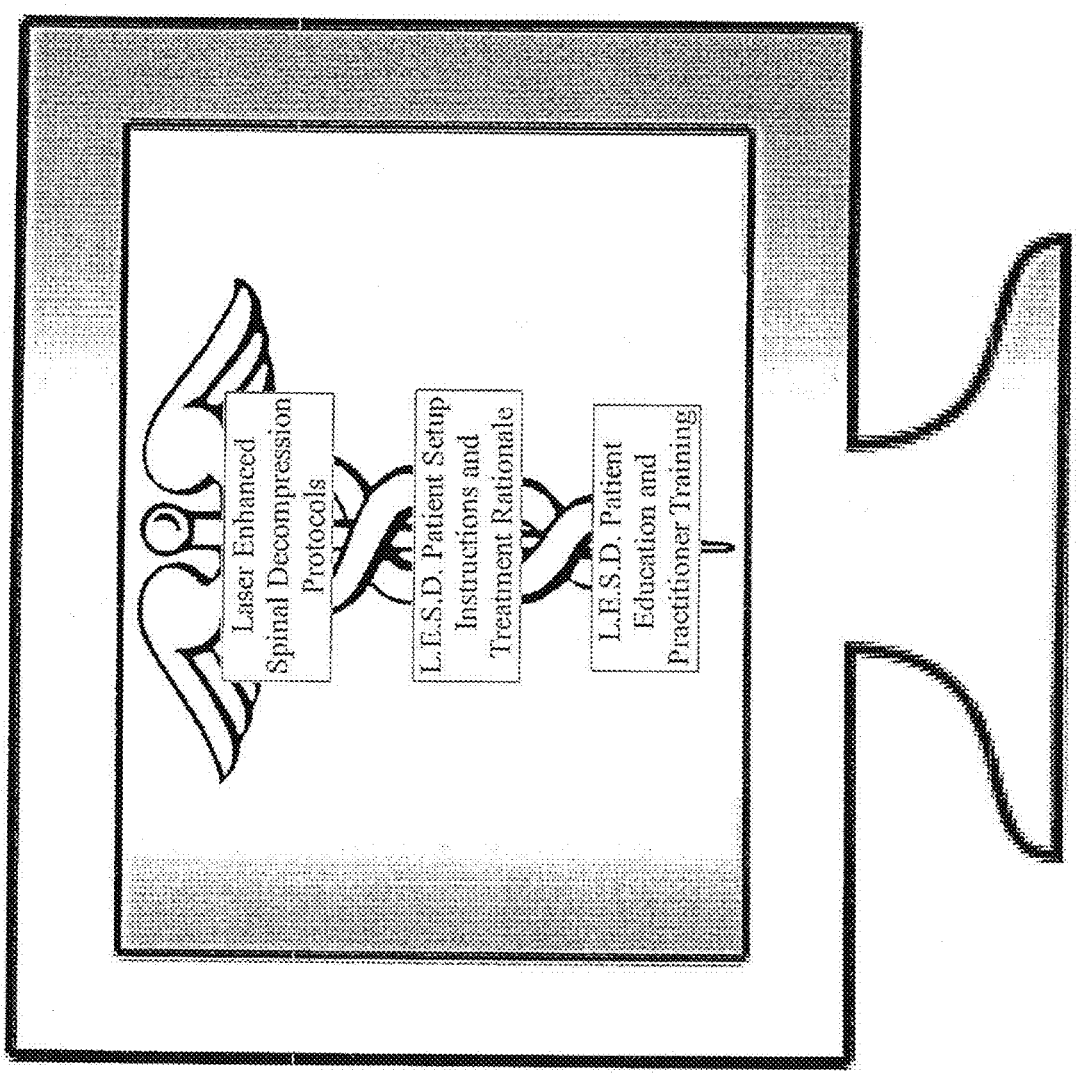
FIG. 15B is a screen shot illustrating one aspect of the software of the current invention, showing options relating to the Laser Enhanced Spinal Decompression of the current invention, including window buttons to access specific Protocols, Patient Set-up instructions, and Practitioner training options.
Figure 15C:
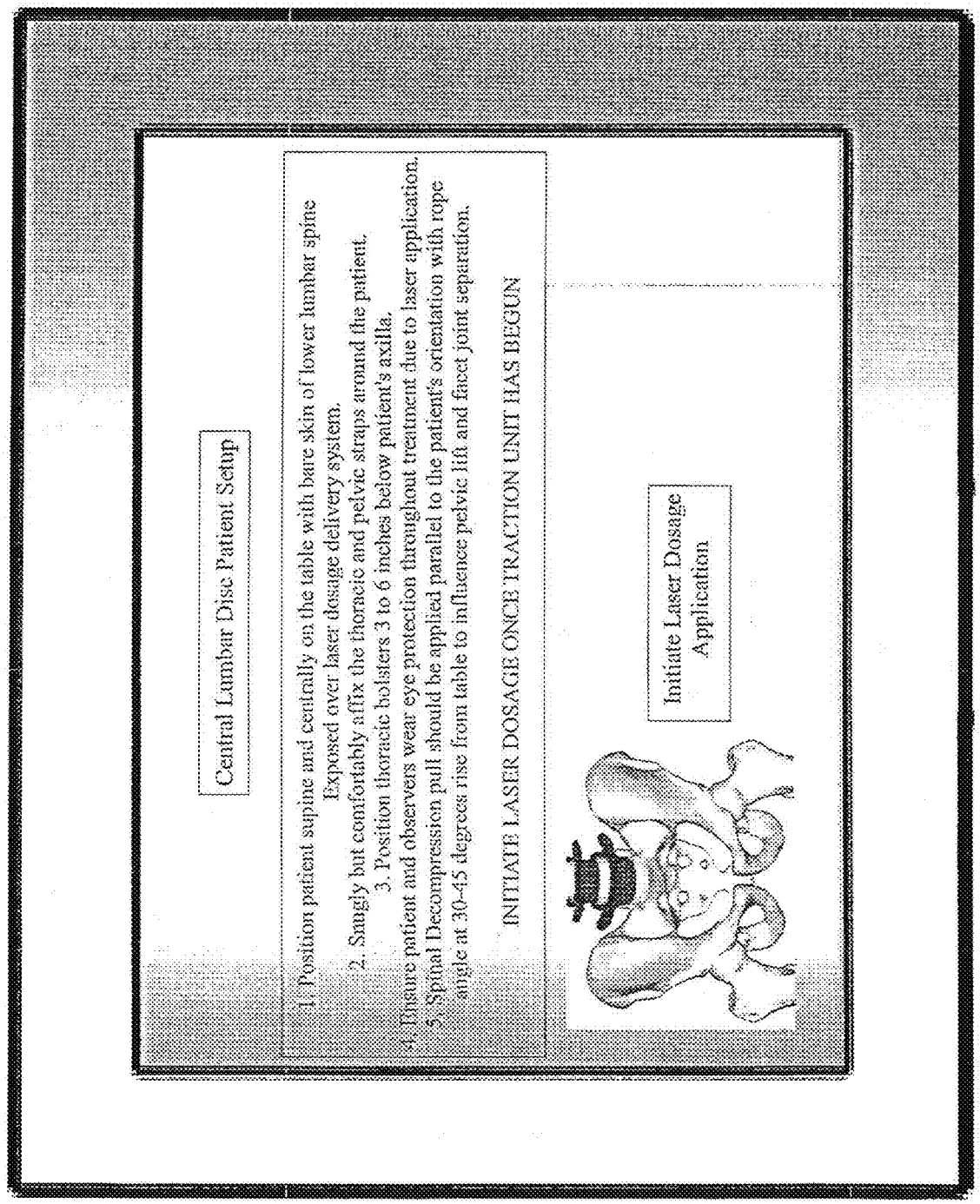
FIG. 15C is a screen shot illustrating another aspect of the software of the current invention, showing a checklist for a practitioner to follow in performing central lumbar disc Laser Treatment.
Figure 16A:
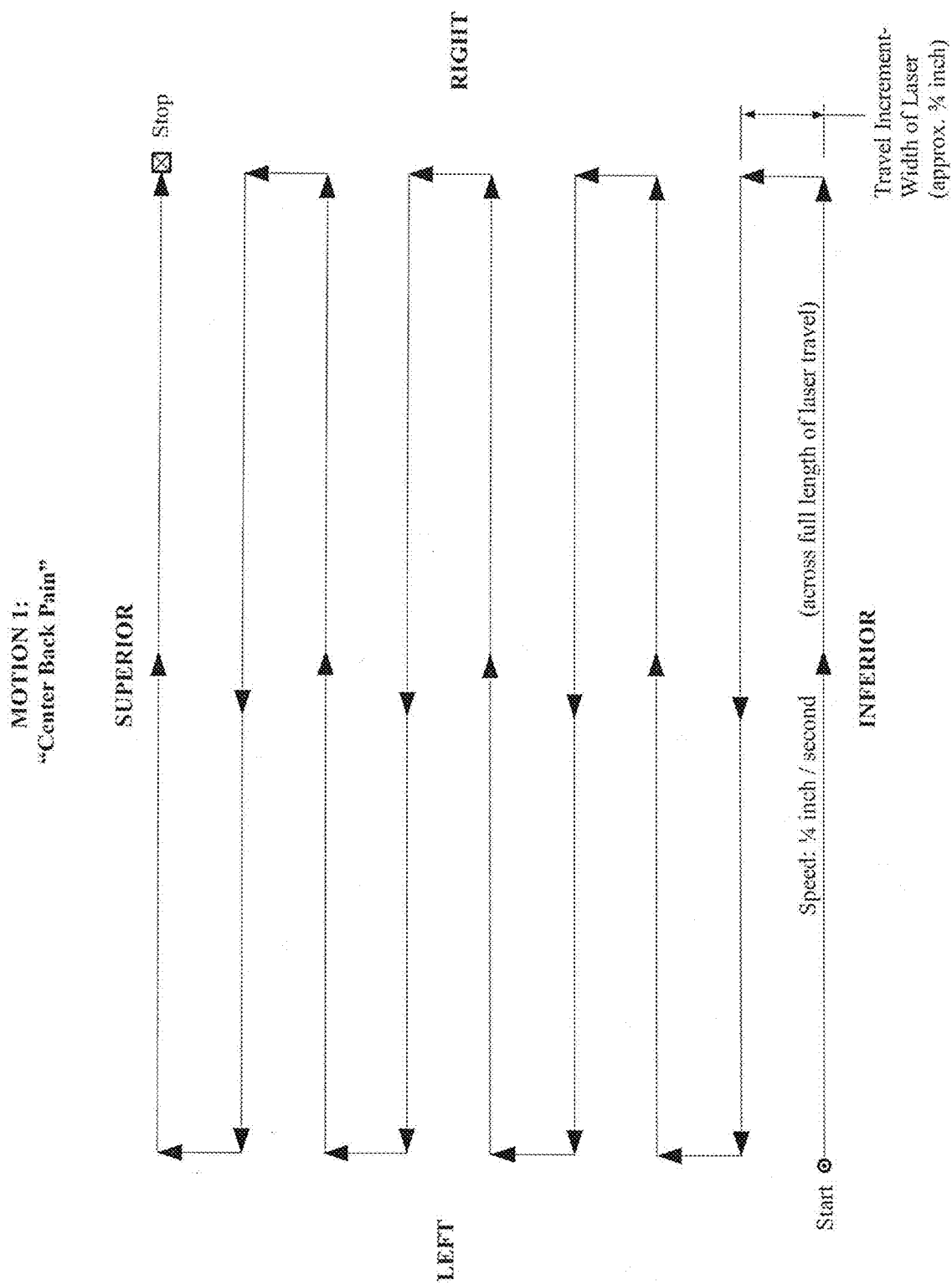
Figure 16C:
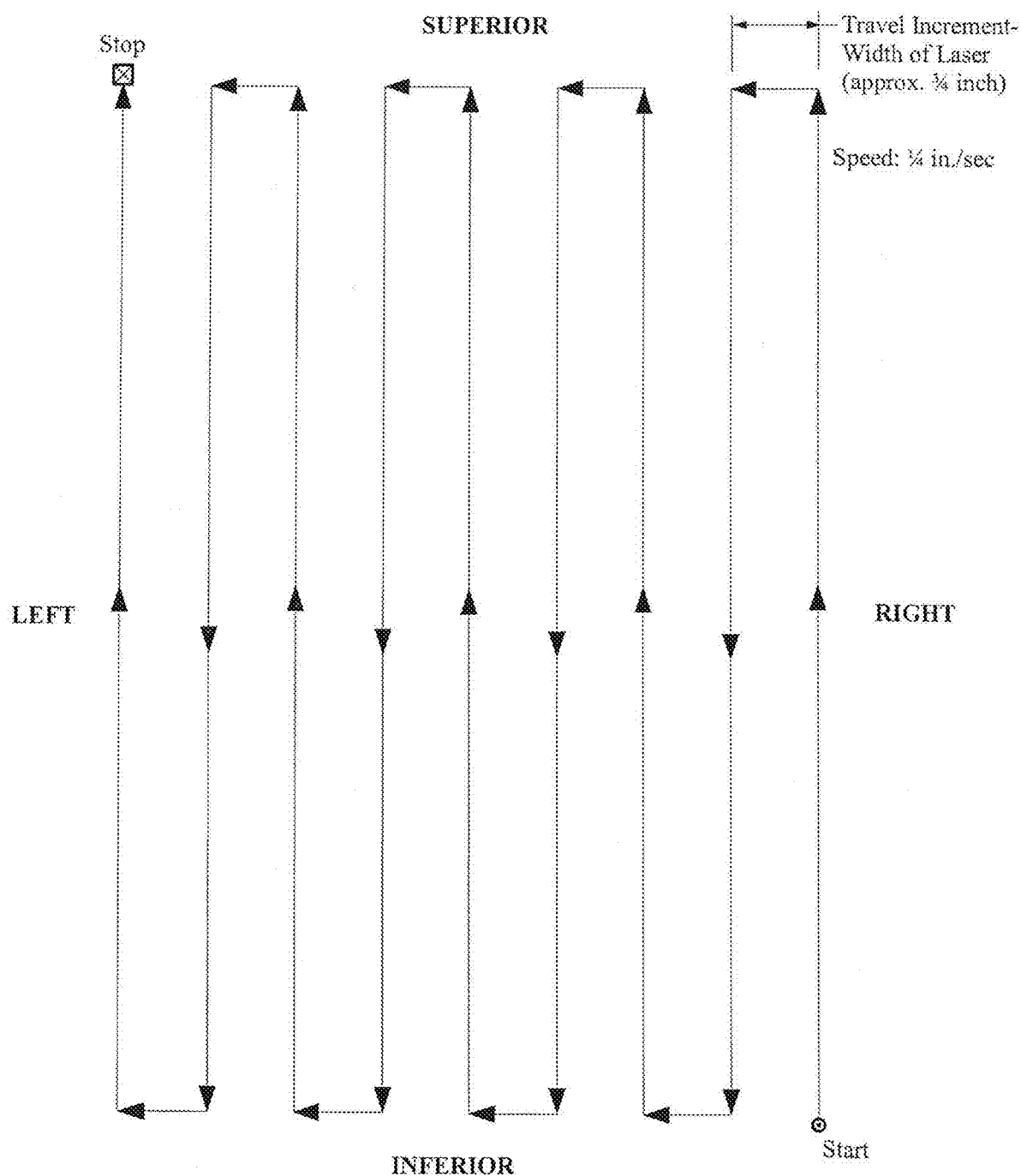
Figure 16D:
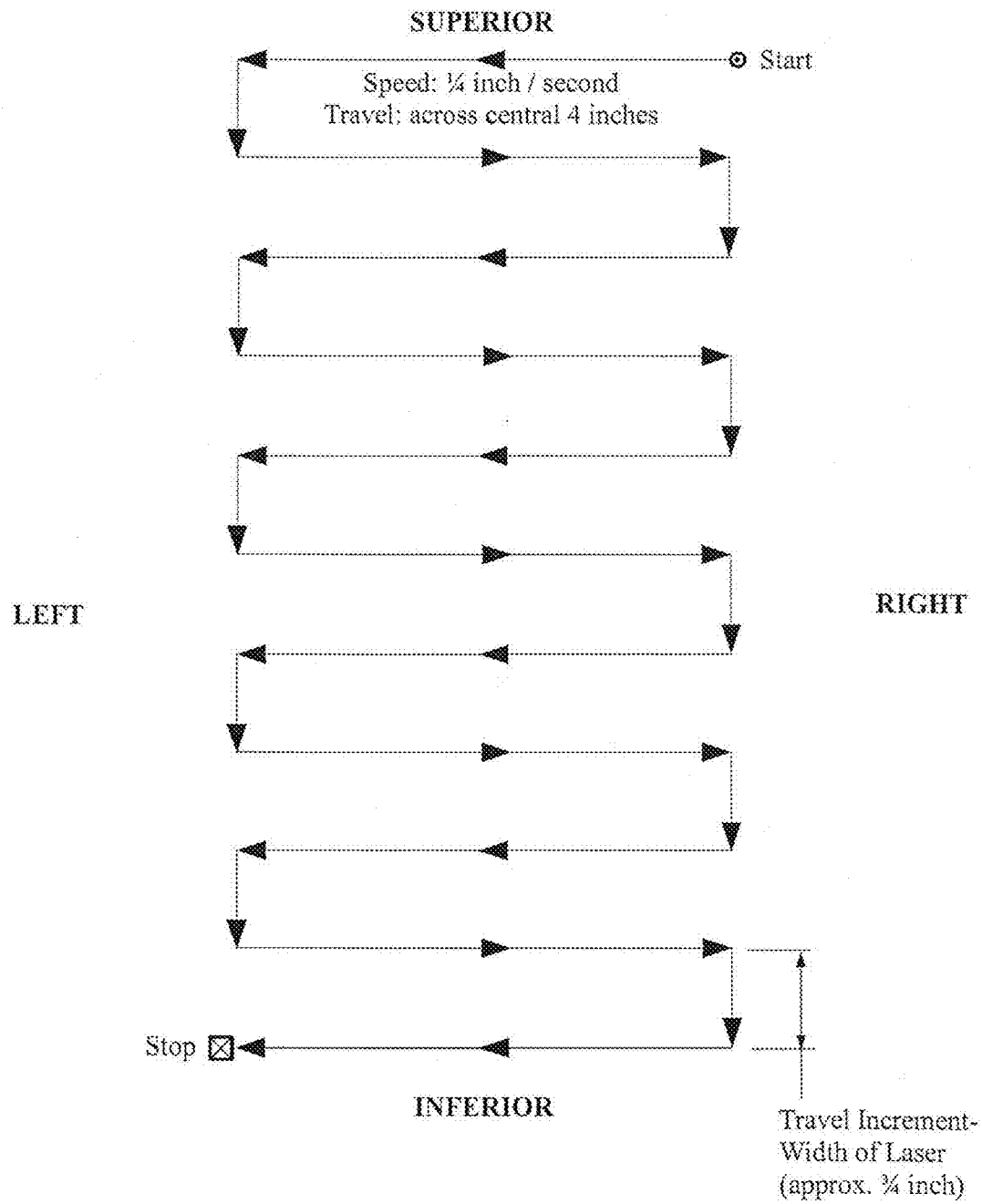
Figure 16E:
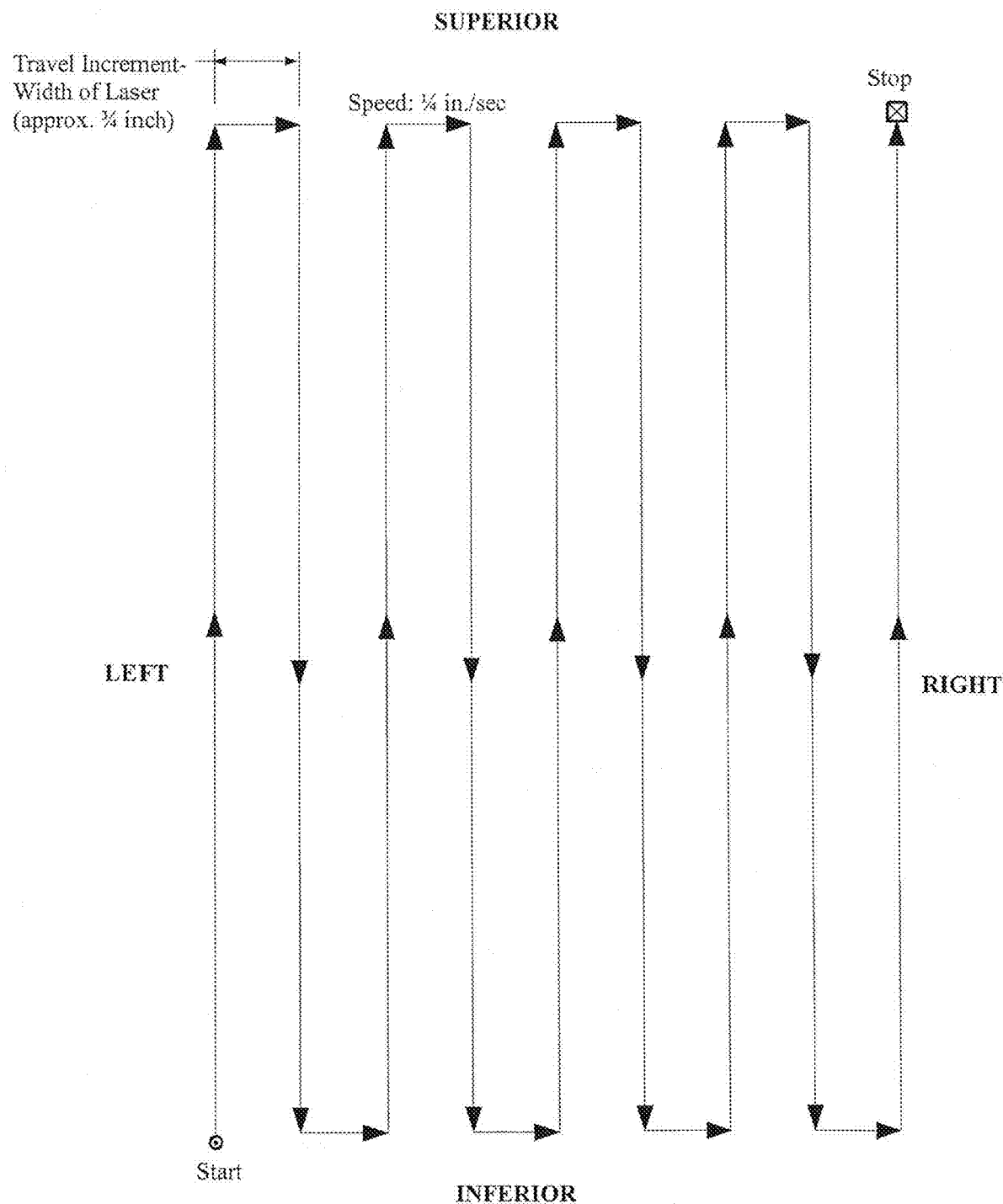
Figure 16F:
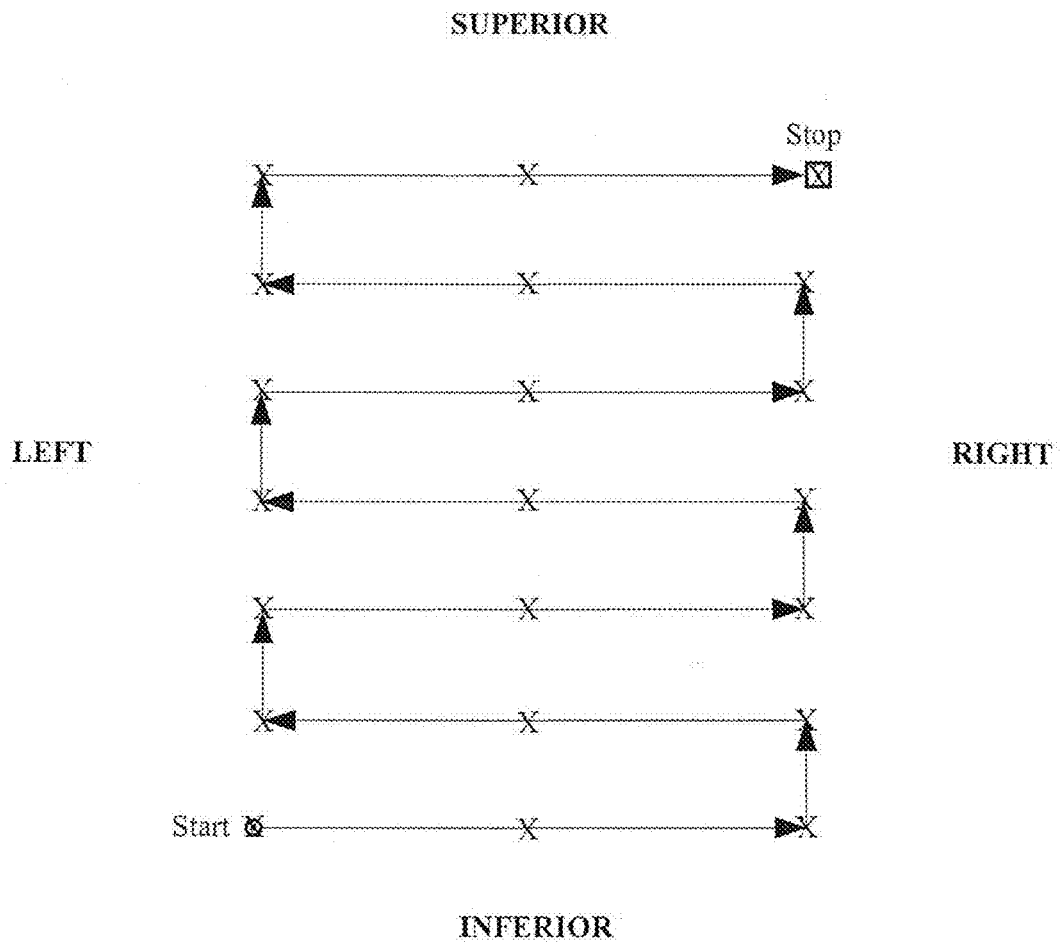
Figure 16G:
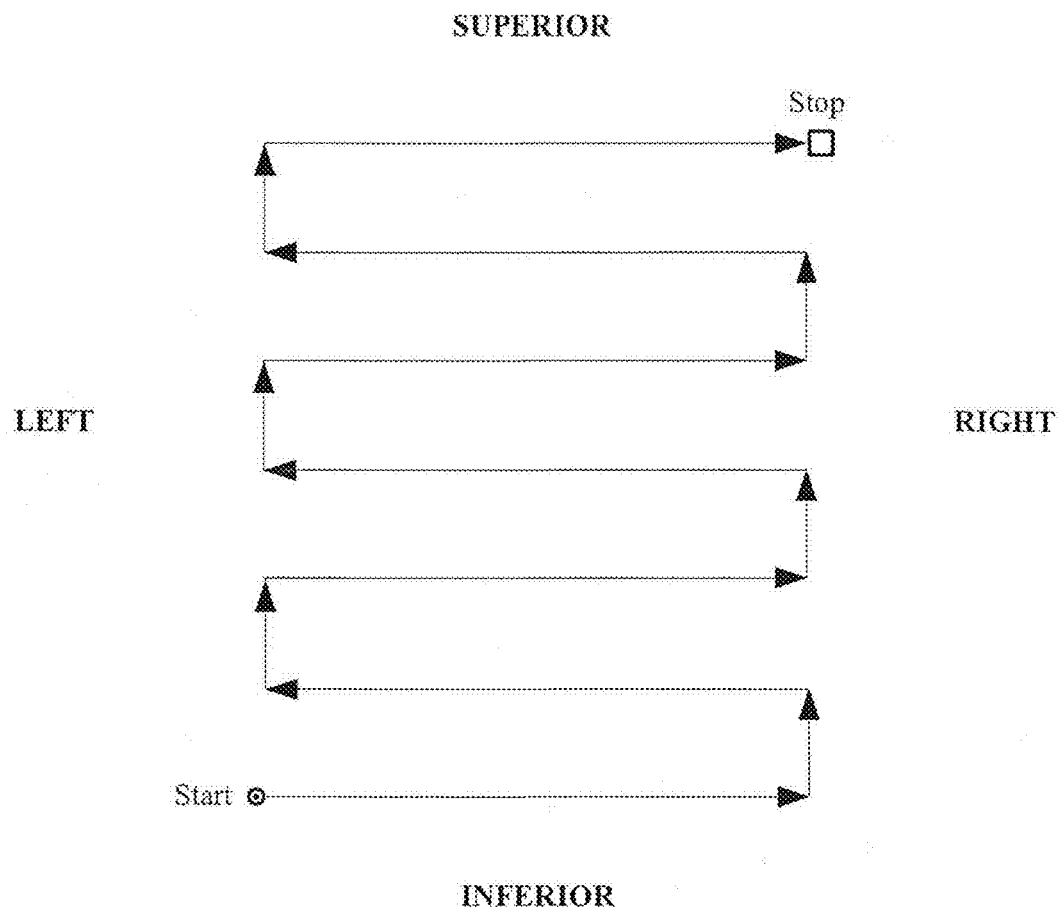
Figure 16H:
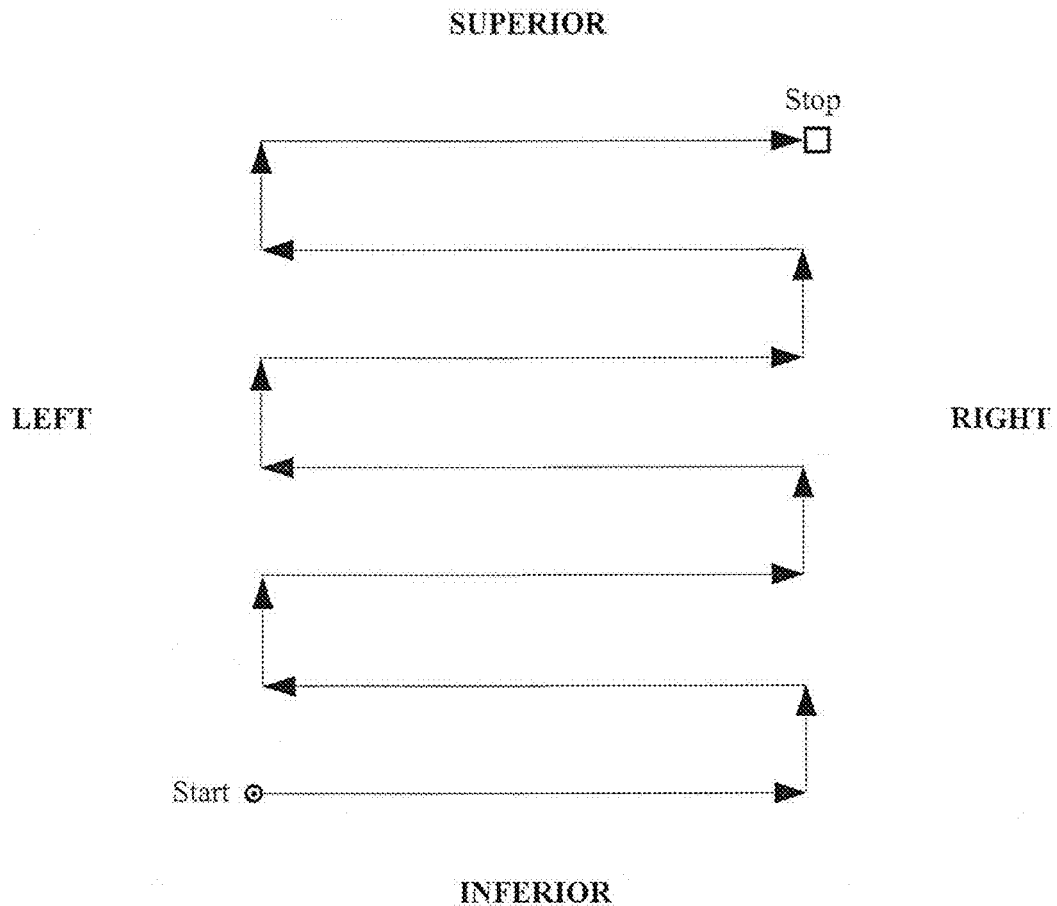
Figure 17A:
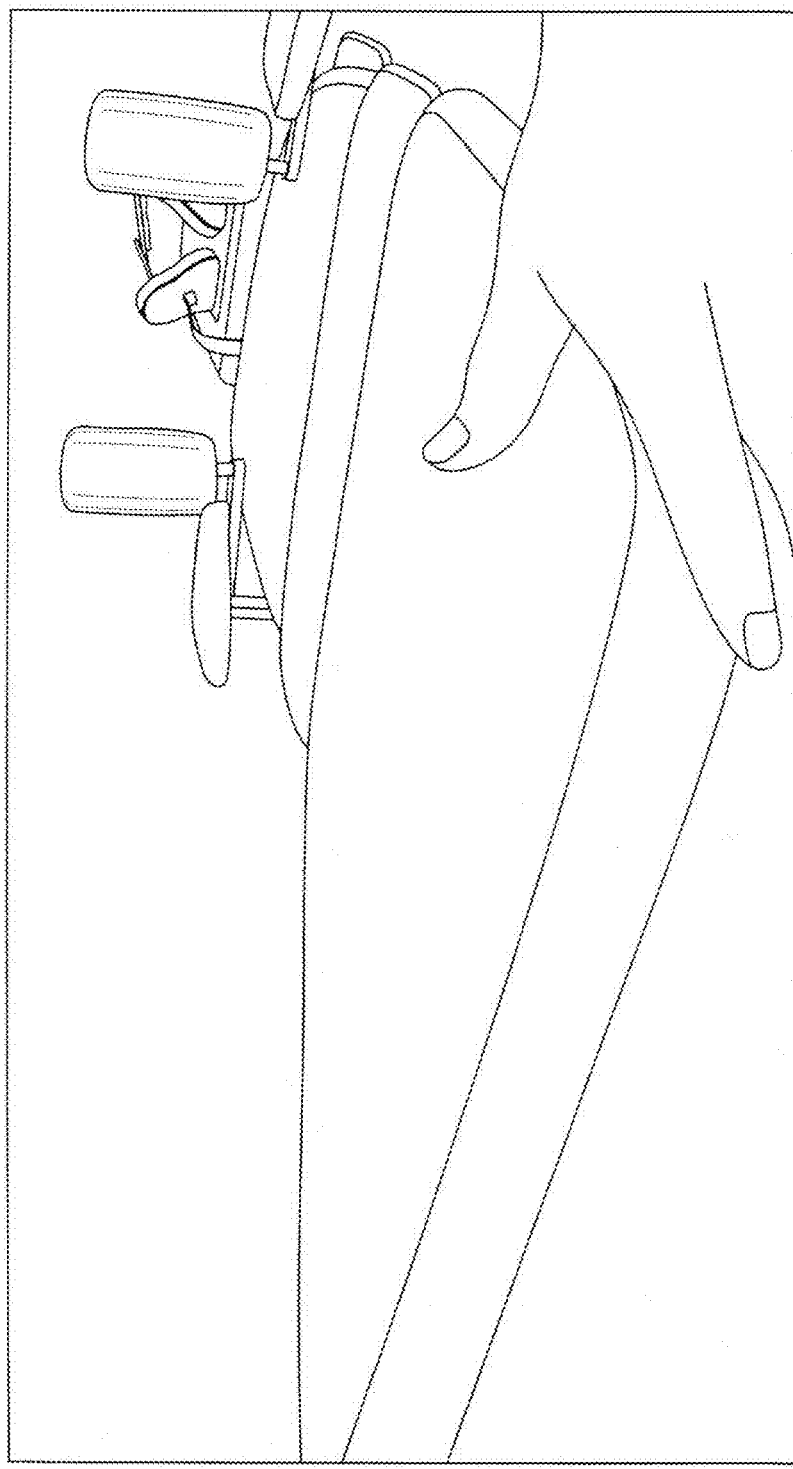
FIG. 17A shows the leg section of the treatment as it is initially being pivoted into an angled position.
Figure 17B:
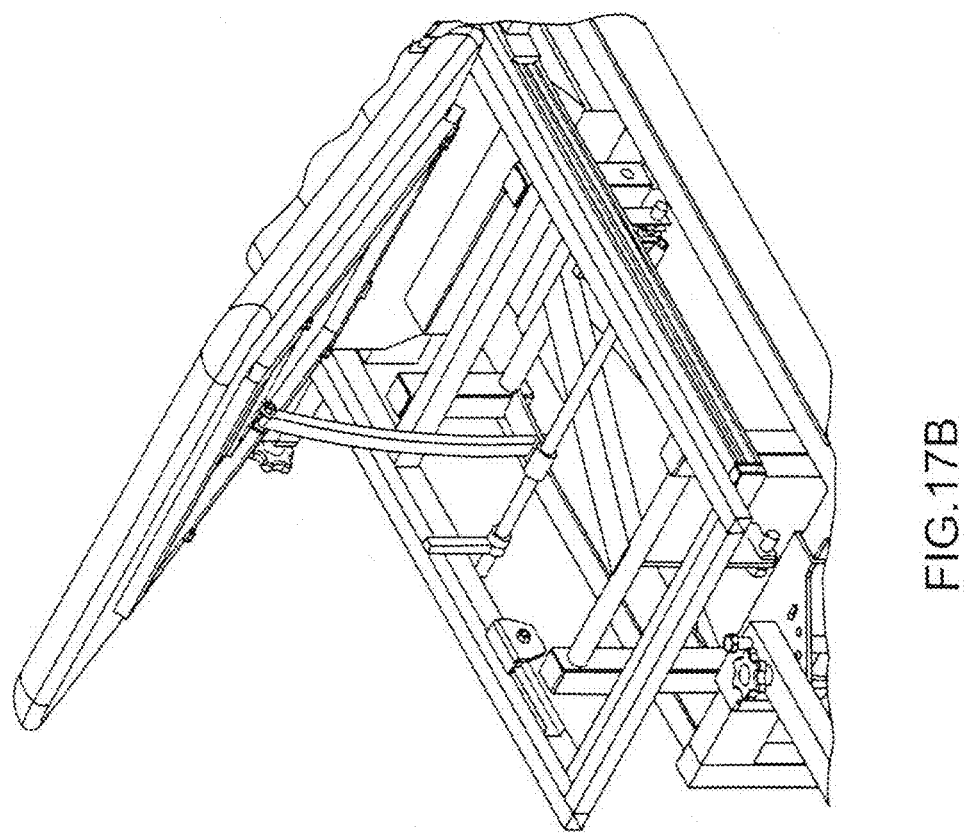
FIG. 17B shows the leg section elevated into an upward-angled position, and locked thereat using a support member.

Programmed Protocols for the Laser Enhanced Spinal Decompression Technique may be in one of at least two modes: a Quadrant Selection Mode and a Protocol Mode. In the quadrant selection mode, six quadrants may be treated as follows:
  2 center between approximately L3-S2 (distal) and T12-L3 (proximal)
  2 right sided and 2 left sided at the same level.
Any of these quadrants may be selected to tailor laser application to specific region based on pain or decompression sequence In the Protocol Mode, which may be selected from an interactive screen on a computer, as seen in FIGS. 14D and 15A, there may be preprogrammed patient-specific or treatment-specific protocols—protocols usable for different regions of the body (e.g., for small joint pain in the fingers or large joint pain such as for the knee or ankle, per FIGS. 16G and 16H). With respect to spinal decompression protocols, as seen for the computer screen image of FIG. 15B, there may preferably be Five Protocols as follows:
1. Parallel Axial Laser Enhanced Spinal Decompression for Left Sided Involvement—Beginning left to right travel of the laser implement working upwards—for straight decompression protocols with left sided involvement/pain. (See e.g., FIG. 16A)
2. Parallel Axial Laser Enhanced Spinal Decompression for Right Sided Involvement—Beginning right to left travel of laser implement working upwards—for straight decompression protocols with right sided involvement/pain.
3. Lateral Axial Laser Enhanced Spinal Decompression for Right Sided Involvement—Beginning caudal to cephalad travel of laser implement moving from right to left—for right lateral flexion decompression protocols creating concentrated decompression of right spinal elements (stretching the spine into a right sided convexity). This applies laser to the right side first aiding decompression of the right sided elements. (See Motion #3A and #3B in FIGS. 16C and 16D)
4. Lateral Axial Laser Enhanced Spinal Decompression for Left Sided Involvement—Beginning caudal to cephalad travel of laser implement moving from left to right—for left lateral flexion decompression protocols creating concentrated decompression of left spinal elements (stretching the spine into a left sided convexity). This applies laser to the left side first aiding decompression of the left sided elements. (See Motion #4A and #4B in FIGS. 16E and 16D)
5. Parallel Axial Laser Enhanced Spinal Decompression with Automated Laser Acupuncture—Beginning caudal to cephalad in the center of the laser travel moving in 1 inch increments concentrating the laser dosage at each increment for a stopping period of 15 seconds at each increment. Implement then moves to 2 inches left from center and travels cephalad to caudal with same pattern to the bottom of the travel followed by another caudal to cephalad pattern 2 inches to right of center. (Note an alternative "Lumbar Laser Acupuncture" protocol is illustrated in FIG. 16F).

Note, that for all protocols, the laser unit may preferably be set at 10 Watts continuous power unless a patient is sensitive to laser light or has increased melanin/darker skin tones. In these cases the laser may instead be set on the pulsed method, giving 10 Watts pulsed or a net 5 Watts.

A Central Lumbar Spinal Pain or Disc Bulge/Herniation/Stenosis Decompression Protocol may comprise: a decompression angle being arranged parallel with spine beginning at approximately 40% of a patient's body weight working to approximately 70% of the patient's body weight or to patient tolerance (never exceeding 85% body weight for lumbar). In some cases it will be advantageous to apply lateral decompression protocols after the 6th session to enhance paraspinal muscle flexibility. This may be applied this for a time of 8 minutes per side consecutively after a 5 minute straight decompression. This is especially advantageous for those suffering from chronic muscle hypertonicity and Osteoarthritis. Mobility is the key for these patients and this technique more effectively achieves this. The laser would be applied to the side/area being stretched, (i.e., straight decompression=central or laser across entire travel of motion device beginning from the sacrum to L1 (caudal to cephalad), decompression of right spinal elements creating right spinal convexity=laser applied to right musculature/ spinal elements first working across the center and then left lumbar spine to finish), decompression of left spinal elements creating left spinal convexity=laser applied to left musculature/spinal elements first followed by the center and right spinal elements.)

The intent of computer controller laser therapy treatment table is to decrease treatment times and provide more effective therapy, as it allows the practitioner to apply the laser dose while the patient is under decompression, instead of prior to or following the decompression session. As the spinal segments are decompressed the laser dose can travel into the desired disc and related tissue more freely, being less inhibited by the surrounding bony structures. The laser is also intended to increase the circulation and elasticity of the involved tissues allowing the decompression treatment to be more comfortable for the patient and more thorough in its application to the desired tissues.

Optional accessories uniquely designed for mounting to the multi-functional table 10 of the current invention may comprise:

An Examination Paper Holder to provide hands-free assistance to the practitioner;
Configurations of headpiece, armrests, strapping and bolster systems that have been designed for ideal use by multiple different practitioner types (Chiropractors, Physio/Physical Therapists, Acupuncturists, Naturopathic Doctors, Massage Therapists, Athletic Therapists, Rehabilitation Specialists and Assistants, Medical Doctors and Specialists). The intent of this is to provide a system that is not only suitable for multiple practitioner use, but is ergonomically ideal for each practitioner. This creates a treatment device suitable for any practitioner in a one device one solution for multiple users using a minimal amount of valuable treatment space and time.
Leg stirrups;
Safety Side Rails—fold down or swing down;
Safety straps;
Fitted pad covers for protection;
Fitted pad covers with extra padding for treatments and other uses requiring a more comfortable patient support surface;
Treat table surfaces, components and accessories with bacteriophage for decontamination purposes; and
Brand name IV-7 and the like, such as silver ion solution for decontamination purposes;

Protocols selectable using the present invention are designed with very specific programming and capabilities relating to a specific patient diagnosis. This allows the doctor to select a pre-programmed protocol deemed most suitable for each patient condition, considering symptomatic factors along with the areas of anatomical injury. The protocols may include use of particular rope angles for application of the traction by the traction machine, which angle(s) may be adjusted, as described above, by adjusting the height of the platform member 72 relative to the table. Eight additional protocols with particular angular requirements for the traction are hereinafter disclosed.

Figure 21B:
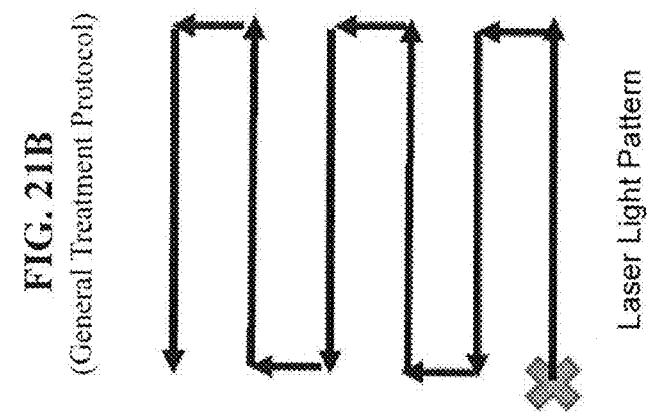
FIG. 21B illustrates the laser light pattern used with the rope angle arrangement for the treatment protocol of FIG. 21A.
Figure 21A:
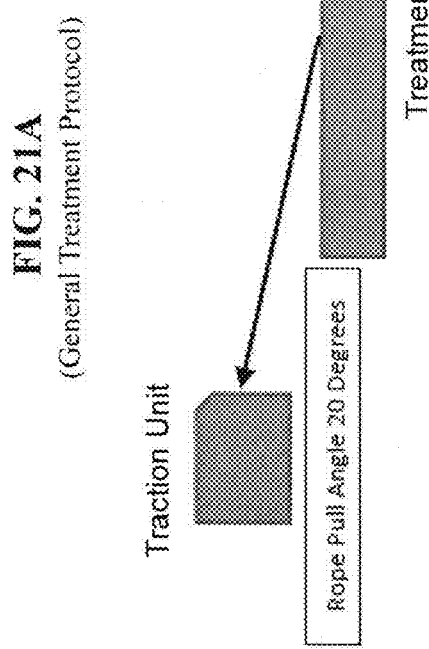
FIG. 21A is a schematic illustration showing the rope angle formed by the elevated positioning of the traction unit with respect to the treatment table, for use in a general treatment protocol.

A first such additional protocol is as lumber protocol suitable for mechanical low back pain of central disc bulge or general non-disc etiology, and is represented schematically in FIGS. 21A-21B. The decompression/traction may be selected to range from 40% to 70% of the patient's body weight, depending upon the stage of treatment. The first few treatments may start at the 40% value, and may progress upwards in accordance with patient tolerance. The traction machine may be set to pull linearly parallel to the patient's position with a 20 degree rope angle, as shown in FIG. 21A, which may be as suitable angle to generally stretch the entire lumbar spine. (Note that the traction unit may, for example, be the unit manufactured by DJO, LLC, in Vista Calif., sold under the trademarked name of Triton DTS®). With this protocol, the laser is set to traverse the entirety of the treatable lumbar area in a ladder type pattern (see FIG. 21B), starting at the bottom right of the patients lumbar area moving towards bottom left, then moving cephalad one beam width (approximately 1 inch), then back across to the patients right side. This pattern is continued in the manner illustrated until reaching the top of the treatable area at which time the laser may return to its home position in the center of the treatment area for cooling of the laser (approximately 6 minutes), as the 15 minute decompression traction treatment continues.

Figure 22B:
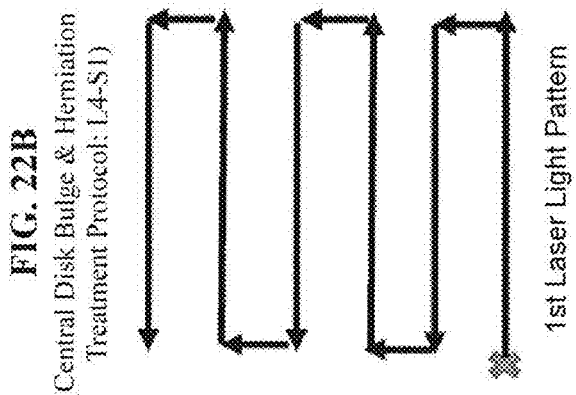
FIG. 22B illustrates a first laser light pattern used with the rope angles for the treatment protocol of FIG. 22A.
Figure 22C:
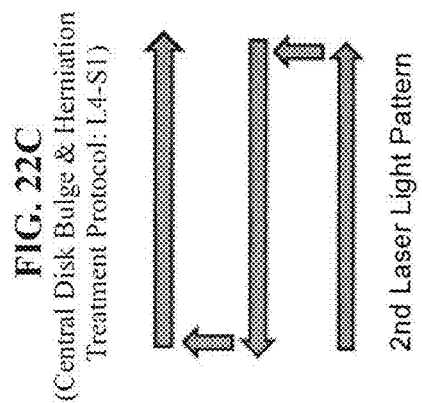
FIG. 22C illustrates a second laser light pattern used with the rope angles for the treatment protocol of FIG. 22A.
Figure 22A:
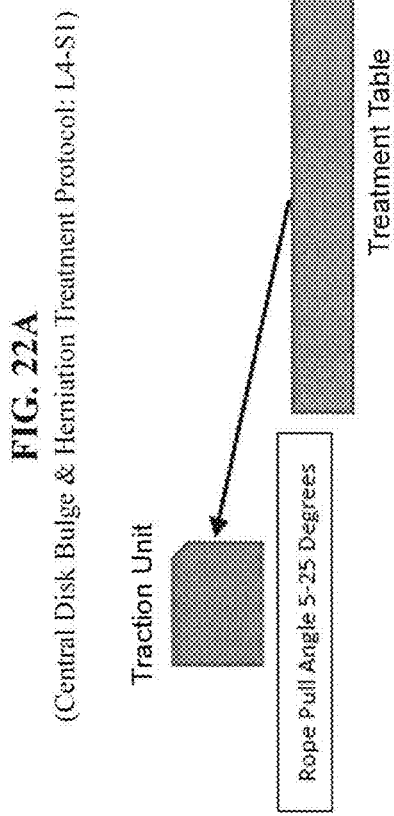
FIG. 22A is a schematic illustration showing the rope angles formed by the positioning of the traction unit with respect to the treatment table, for a treatment protocol for central disc bulge/herniation at L4-S1.

A second such additional protocol is suitable for central disc bulge/herniation at L4-S1. A decompression/traction force may be selected as described for the first additional protocol (i.e., 40% to 70% of the patient's body weight . . . ). Also, the height of the platform member 72 may be suitably adjusted relative to the treatment table for the traction machine being utilized to apply traction with a rope angle in the range of 5 degrees to 25 degrees, as illustrated schematically in FIG. 22A. In particular, the protocol may be subdivided for treatment of L5 to S1 and for treatment of L4-L5, such that the rope angle used for traction for treatment of L5-S1 is between 5 degrees and 15 degrees, and the rope angle used for traction for treatment of L4-L5 is 15 degrees to 25 degrees. During this protocol the laser is set to traverse the pattern shown in FIG. 22B, which may be identical to the pattern shown in FIG. 21B. This second protocol may further include two additional minutes of laser light treatment covering an area that is approximately four inches by six inches, using the horizontal ladder pattern illustrated in FIG. 22C, being focused on the specific areas of identified lumbar pathology from L4-S1.

A third such additional protocol is suitable for central disc bulge/herniation at L1-L4. A decompression/traction force may be selected as described for the first additional protocol (i.e., 40% to 70% of the patient's body weight . . . ). Also, the height of the platform member 72 may be suitably adjusted relative to the treatment table for the traction machine being, utilized to apply traction with a rope angle in the range of 25 degrees to 45 degrees, as illustrated schematically in FIG. 23A. In particular, the protocol may be subdivided for treatment of L3-L4 and for treatment of L1-L2, such that the rope angle used for traction for treatment of L3-L4 is 25 degrees, where the rope angle for treatment of L2-L3 is 35 degrees, and the rope angle used for traction for treatment of L1-L2 is 45 degrees. During this protocol the laser is set to traverse the pattern shown in FIG. 23B, which may be identical to the pattern shown in FIG. 21B. This third protocol may further include three additional minutes of laser light treatment covering an area that is approximately four inches by six inches, using the horizontal ladder pattern illustrated in FIG. 23C (which may be identical to the pattern shown in FIG. 22C), with this additional treatment pattern being focused on the specific areas of identified lumbar pathology from L1-L4.

Figure 24B:
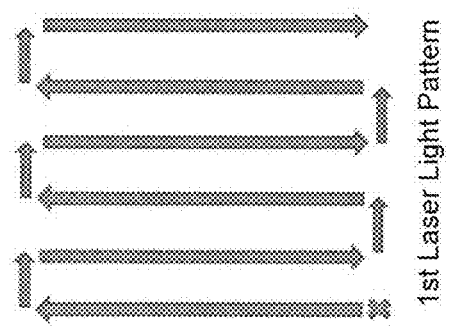
FIG. 24B illustrates a first laser light pattern used with corresponding rope angles for the treatment protocol of FIG. 24A.
Figure 24C:
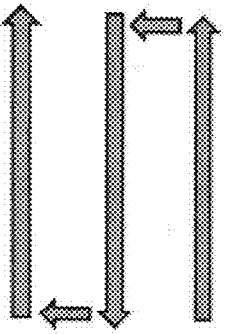
FIG. 24C illustrates a second laser light pattern used with corresponding rope angles for the treatment protocol of FIG. 24A.
Figure 24A:
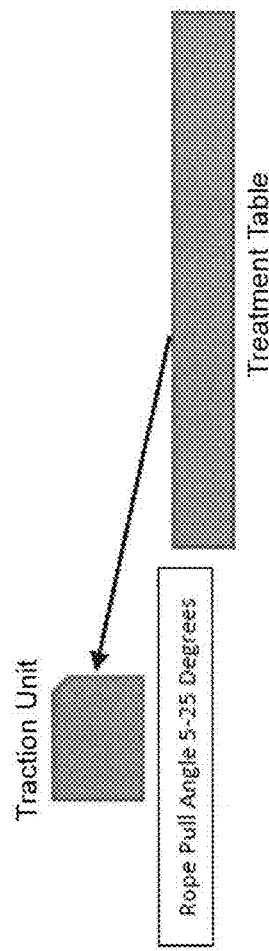
FIG. 24A is a schematic illustration showing the rope angles formed by the positioning of the traction unit with respect to the treatment table, for a treatment protocol for right lateral disc bulge/herniation at L4-S1.

A fourth such additional protocol is suitable for right lateral disc bulge/herniation at L4-S1. A decompression/ traction three may be selected as described for the first additional protocol (i.e., 40% to 70% of the patient's body weight . . . ). Also, the height of the platform member 72 may be suitably adjusted relative to the treatment table for the traction machine being utilized to apply traction with a rope angle in the range of 5 degrees to 25 degrees, as illustrated schematically in FIG. 24A. In particular, the protocol may be subdivided for treatment of L5 to S1 and for treatment of L4-L5, such that the rope angle used for traction for treatment of L5-S1 is in the range of 5 degrees to 15 degrees, and the rope angle used for traction for treatment of L4-L5 is in the range of 15 degrees to 25 degrees. The traction platform 72 may also be suitably adjusted laterally relative to the treatment table, to be positioned 30 degrees towards the patient's left side (see e.g., FIG. 4B), so as to create a greater distraction force to the right side of the patient's spine, effectively decompressing the specific area of disc bulge on the right side. During this protocol the laser may be set to traverse the pattern shown in FIG. 24B, and may traverse from the bottom right of the treatable area towards the top right, then incrementally working its way towards the patient's left side using a ladder pattern. This protocol may further include two additional minutes of laser light treatment covering an area that is approximately four inches by six inches, with the horizontal ladder pattern illustrated in FIG. 24C (which may be identical to the pattern shown in FIG. 22C), with this additional treatment pattern being focused on the specific areas of identified lumbar pathology from L4-S1. The purpose of this pattern beginning on the patient's side of pathology (right) and incrementally working towards the opposite side (left) is to initially focus on the pathology and structures experiencing the most decompressive force to relax and relieve, providing a much more specific concentration on the diagnosed condition.

A fifth such additional protocol is suitable for left lateral disc bulge/herniation at L4-S1. A decompression/traction force may be selected as described for the first additional protocol 40% to 70% of the patient's body weight . . . ). Also, the height of the platform member 72 may be suitably adjusted relative to the treatment table for the traction machine being utilized to apply traction with a rope angle in the range of 5 degrees to 25 degrees, as illustrated schematically in FIG. 25A. In particular, the protocol may be subdivided for treatment of L5-S1 and for treatment of L4-L5, such that the rope angle used for traction for treatment of L5-S1 is in the range of 5 degrees to 15 degrees, and the rope angle used liar traction for treatment of L5 is in the range of 15 degrees to 25 degrees. The traction platform 72 may also be suitably adjusted laterally relative to the treatment table, to be positioned 30 degrees towards the patient's right side (see e.g., FIG. 4A), so as to create a greater distraction force to the left side of the patient's spine, effectively decompressing the specific area of disc bulge on the left side. During this protocol the laser may be set to traverse the pattern shown in FIG. 25B, and may traverse from the bottom left of the treatable area towards the top left, then incrementally working its way towards the patient's right side using a ladder pattern. This protocol may further include two additional minutes of laser light treatment covering an area that is approximately four inches by six inches, using the horizontal ladder pattern illustrated in FIG. 25C, with this additional treatment pattern being focused on the specific areas of identified lumbar pathology from L4-S1. The purpose of this pattern beginning on the patient's side of pathology (left) and incrementally working towards the opposite side (right) is to initially focus on the pathology and structures experiencing the most decompressive force to relax and relieve, providing a much more specific concentration on the diagnosed condition.

Figure 26B:
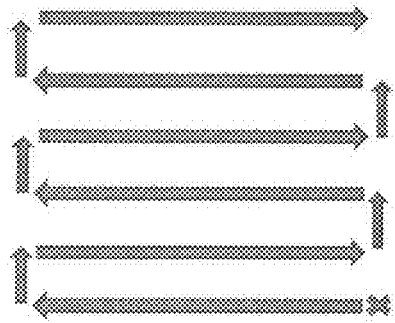
FIG. 26B illustrates a first laser light pattern used with corresponding rope angles for the treatment protocol of FIG. 26A.
Figure 26C:
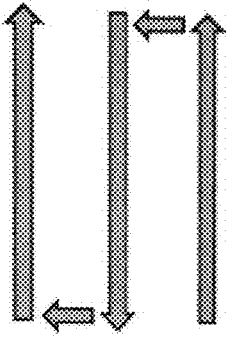
FIG. 26C illustrates a second laser light pattern used with corresponding rope angles for the treatment protocol of FIG. 26A.
Figure 26A:
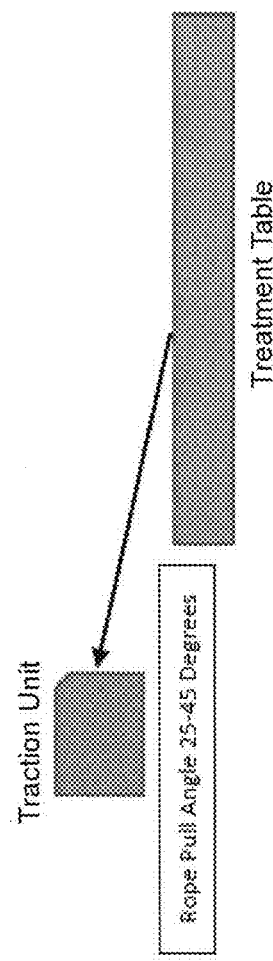
FIG. 26A is a schematic illustration showing the rope angles formed by the positioning of the traction unit with respect to the treatment table, for a treatment protocol for right lateral disc bulge/herniation at L1-L4.

A sixth such additional protocol is suitable for right lateral disc bulge/herniation at L4. A decompression/traction force may be selected as described for the first additional protocol (i.e., 40% to 70% of the patient's body weight . . . ). Also, the height of the platform member 72 may be suitably adjusted relative to the treatment table for the traction machine being utilized to apply traction with a rope angle in the range of 25 degrees to 45 degrees, as illustrated schematically in FIG. 26A. In particular, the protocol may be subdivided for treatment of L3-L4 and for treatment of L1-L2, such that the rope angle used for traction for treatment of L3-L4 is 25 degrees, and the rope angle used for traction for treatment of L1-L2 is 45 degrees. The traction platform 72 may also be suitably adjusted laterally relative to the treatment table, to be positioned 30 degrees towards the patient's left side (see e.g., FIG. 4B), so as to create a greater distraction force to the right side of the patient's spine, effectively decompressing the specific area of disc bulge on the right side. During this protocol the laser may be set to traverse the pattern shown in FIG. 26B, and may traverse from the bottom right of the treatable area towards the top right, then incrementally working its way towards the patient's left side using a ladder pattern. This protocol may further include three additional minutes of laser light treatment covering an area that is approximately four inches by six inches, with the horizontal ladder pattern illustrated in FIG. 26C, with this additional treatment pattern being focused on the specific areas of identified lumbar pathology from L1-L4. The purpose of this pattern beginning on the patient's side of pathology (right) and incrementally working, towards the opposite side (left) is to initially focus on the pathology and structures experiencing the most decompressive force to relax and relieve, providing a much more specific concentration on the diagnosed condition.

Figure 27B:
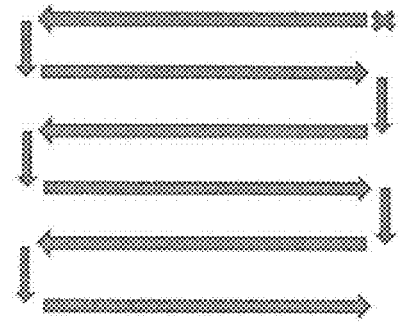
FIG. 27B illustrates a first laser light pattern used with corresponding rope angles for the treatment protocol of FIG. 27A.
Figure 27C:
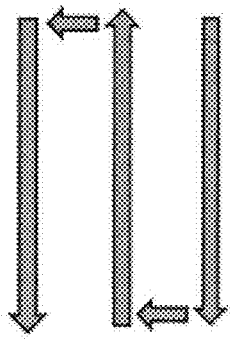
FIG. 27C illustrates a second laser light, pattern used with corresponding rope angles for the treatment protocol of FIG. 27A.
Figure 27A:
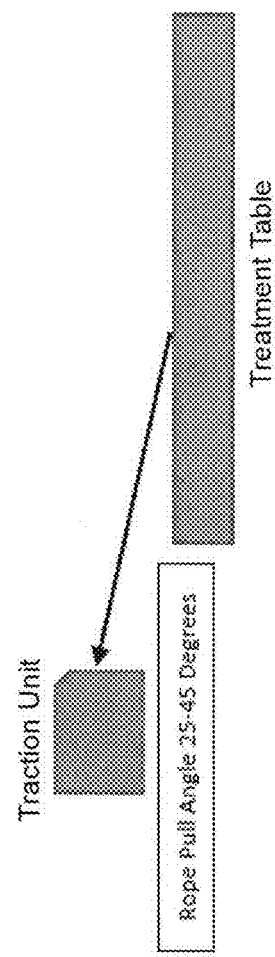
FIG. 27A is a schematic illustration showing the rope angles formed by the positioning of the traction unit with respect to the treatment table, for a treatment protocol for left lateral disc bulge/herniation at L1-L4.

A seventh such additional protocol is suitable for left lateral disc bulge/herniation at L1-L4. A decompression/traction force may be selected as described for the first additional protocol (i.e., 40% to 70% of the patient's body weight . . . ). Also, the height of the platform member 72 may be suitably adjusted relative to the treatment table for the traction machine being utilized to apply traction with a rope angle in the range of 25 degrees to 45 degrees, as illustrated schematically in FIG. 27A. In particular, the protocol may be subdivided for treatment of L3-L4 and for treatment of L1-L2, such that the rope angle used for traction for treatment of L3-L4 is 25 degrees, and the rope angle used for traction for treatment of L1-L2 is 45 degrees. The traction platform 72 may also be suitably adjusted laterally relative to the treatment table, to be positioned 30 degrees towards the patient's right side (see e.g., FIG. 4A), so as to create a greater distraction force to the left side of the patient's spine, effectively decompressing the specific area of disc bulge on the right side. During this protocol the laser may be set to traverse the pattern shown in FIG. 27B, and may traverse from the bottom left of the treatable area towards the top left, then incrementally working its way towards the patient's right side using a ladder pattern. This protocol may further include three additional minutes of laser light treatment covering an area that is approximately four inches by six inches, using the horizontal ladder pattern illustrated in FIG. 27C, with this additional treatment pattern being focused on the specific areas of identified lumbar pathology from L1-L4. The purpose of this pattern beginning on the patient's side of pathology (left) and incrementally working towards the opposite side (right) is to initially focus on the pathology and structures experiencing the most decompressive force to relax and relieve, providing a much more specific concentration on the diagnosed condition.

Figure 28:
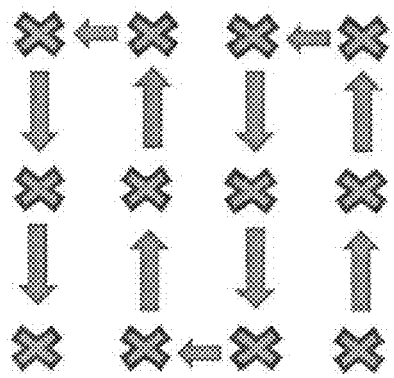
FIG. 28 illustrates a laser light pattern used with an acupuncture treatment protocol.

An eighth such additional protocol is suitable for general low back, mid/upper/cervical spine pain, and is similar to the laser lumbar acupuncture protocol described above and illustrated in FIG. 16F. In this protocol the laser light may be directed to incremental positions according to the ladder pattern shown in FIG. 28, and may instead use a five second dwell at each of the X-marked positions, with the pattern repeated, being performed two times to equal the total ten second spot treatment time discussed above, but which is applied on two separate passes. Use of dwell times longer than five seconds may tend to be uncomfortable for certain patients, and is addressed by this protocol.

The present invention may also provide particularly designed cervical traction protocols. The cervical traction protocols may include use of a particular pull angle being applied by rotation of the tray 87 with respect to the plate 89 using roller wheels 91, to apply lateral cervical traction. The protocols may further include use of a cervical extension angle that may be provided by pivoting of the plate 89 of the cervical section upward/downward about its mounting hinges, for positioning and securing of the plate at the desired angle. Three particular cervical traction protocols are hereinafter disclosed.

For each of the cervical traction protocols, the patient's upper back and neck may be sealed against the cushioned gland, to be positioned over the interconnected openings through which the laser beam is directed. Each of the cervical traction protocols may begin with a general class 4 laser therapy session over the neck and upper back to relieve pain, muscle tension and increase healing, in preparation for cervical decompressive traction.

Figure 29B:
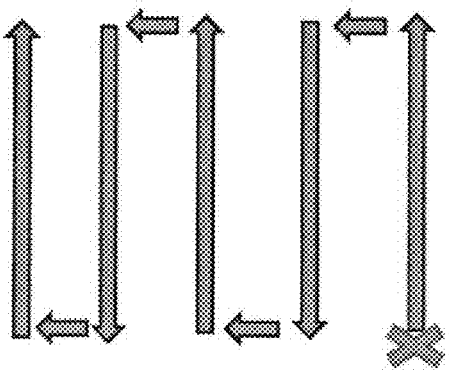
FIG. 29B illustrates a laser light pattern used for the treatment protocol of FIG. 29A.
Figure 29A:
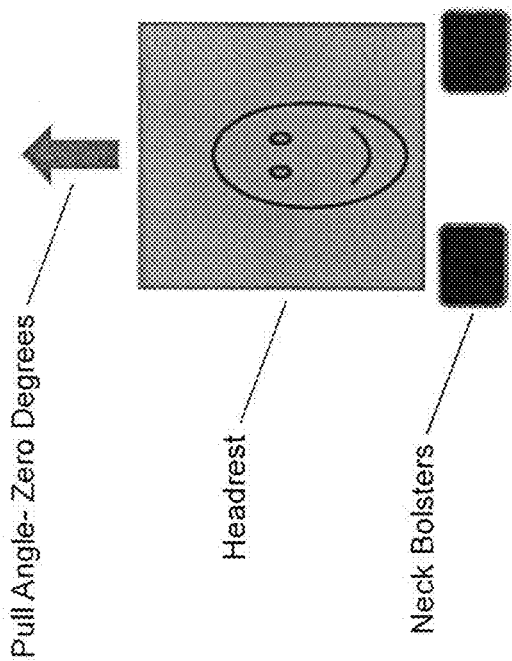
FIG. 29A is a schematic illustration showing a zero degree pull angle for the positioning of a headrest of a cervical traction restraint system with respect to the treatment table, for a treatment protocol for general neck/upper hack pain and central disc protrusion/bulge/herniation.

The first cervical protocol is suitable for general neck/upper back pain and central cervical disc protrusion/bulge/herniation. Following the laser treatment, traction would be applied, and a traction weight would be selected, and may begin at 20 pounds, and may be raised up to 45 pounds incrementally, at a rate dependent upon patient tolerance during such treatments. The traction pull angle would be parallel to patient's body position (i.e., zero degrees laterally—see FIG. 29A), and with zero degrees of elevation. Laser light may be applied using the ladder pattern shown in FIG. 29B.

Figure 30A:
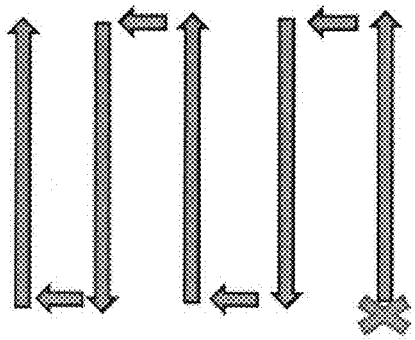
FIG. 30A is a schematic illustration showing a thirty degree pull angle for the positioning of a headrest of a cervical traction restraint system with respect to the treatment table, for a treatment protocol for right lateral cervical disc protrusion/bulge/herniation.
Figure 30B:
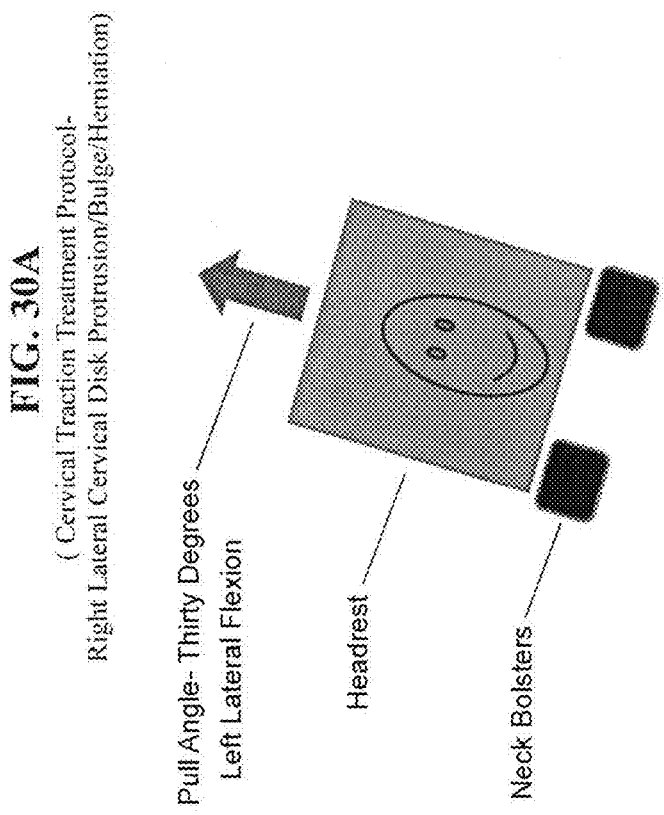
FIG. 30B illustrates a laser light pattern used for the treatment protocol of FIG. 30A.
Figure 30C:
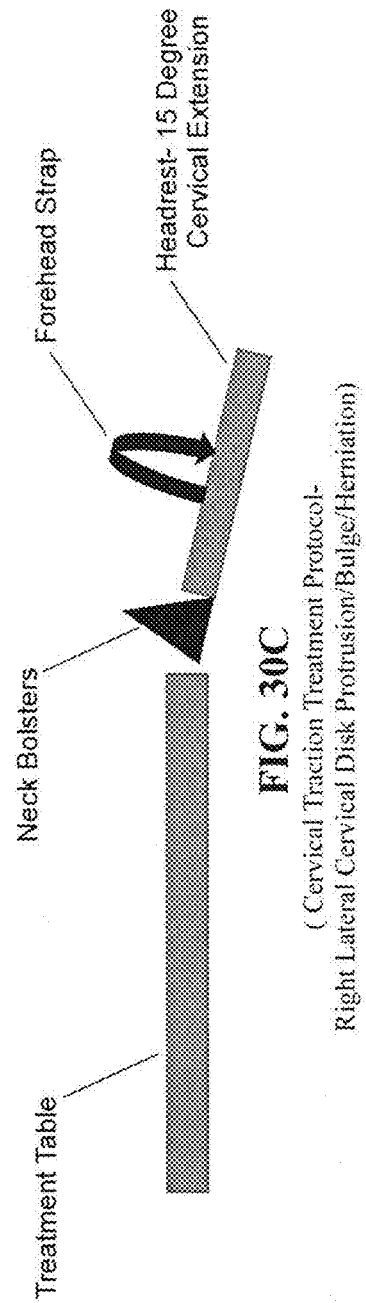
FIG. 30C is a schematic illustration showing use of fifteen degrees of cervical extension for the headrest of FIG. 30A, with respect to the treatment table.

The second cervical protocol—a right lateral cervical disk protocol—is suitable for general neck/upper back pain and right lateral cervical disc protrusion/bulge/herniation. Following the laser treatment, traction would be applied, and a traction weight would be selected, and may begin at 20 pounds, and may be raised up to 45 pounds incrementally, at a rate dependent upon patient tolerance during such treatments. The traction pull angle would be 30 degrees left of patient body position, as shown in FIG. 30A, to provide left lateral flexion. As shown in FIG. 30C, a 15 degree down elevation of the plate 89 relative to the treatment table may be used 15 degrees of cervical extension), to best isolate the right sided disc pathology. Laser light may be applied using the ladder pattern shown in FIG. 30B.

Figure 31A:
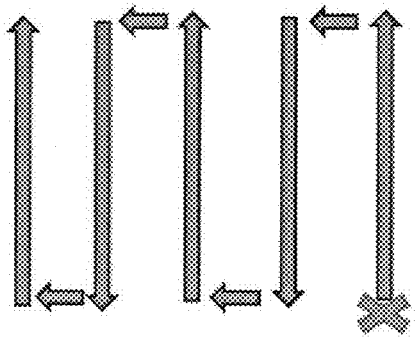
FIG. 31A is a schematic illustration showing a thirty degree pull angle for the positioning of a headrest of a cervical traction restraint system with respect to the treatment table, for a treatment protocol for left lateral cervical disc protrusion/bulge/herniation.
Figure 31B:
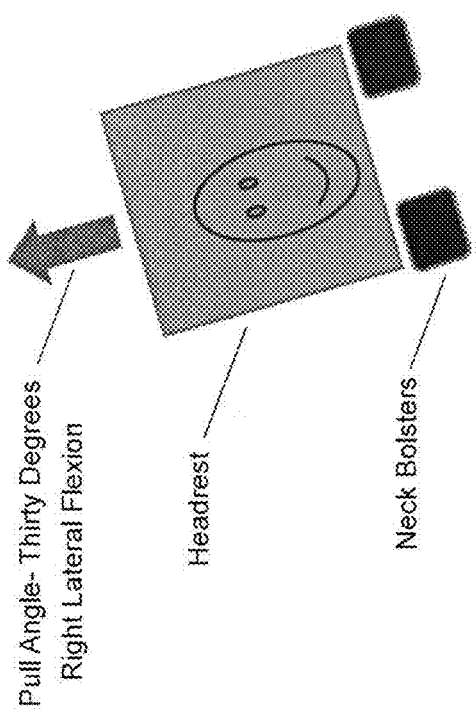
FIG. 31B illustrates a laser light pattern used for the treatment protocol of FIG. 31A.
Figure 31C:
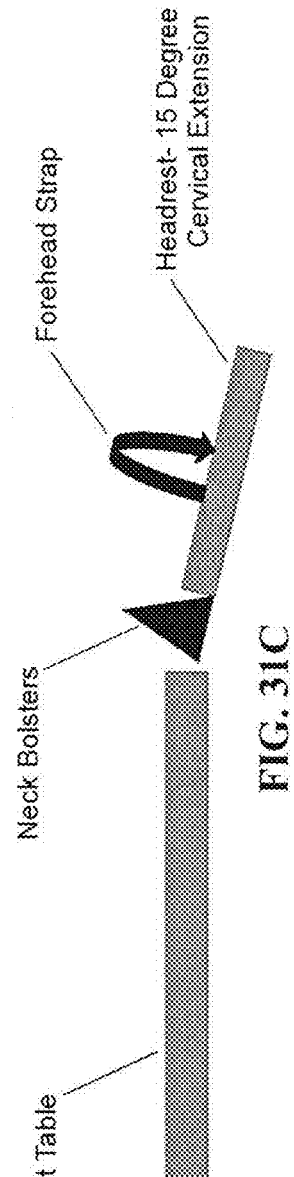
FIG. 31C is a schematic illustration showing use of fifteen degrees of cervical extension for the headrest of FIG. 31A, with respect to the treatment table.

The third cervical protocol—a left lateral cervical disk protocol—is suitable for general neck/upper back pain and left lateral cervical disc protrusion/bulge/herniation. Following the laser treatment, traction would be applied, and a traction weight would be selected, and may begin at 20 pounds, and may be raised up to 45 pounds incrementally, at a rate dependent upon patient tolerance during such treatments. The traction pull angle would be 30 degrees right of patient body position, as shown in FIG. 31A to provide right lateral flexion. As shown in FIG. 31C, a 15 degree down elevation of the plate 89 relative to the treatment table may be used (i.e., 15 degrees of cervical extension) to best isolate the left sided disc pathology. Laser light may be applied using the ladder pattern shown in FIG. 31B.

Figure 32A:
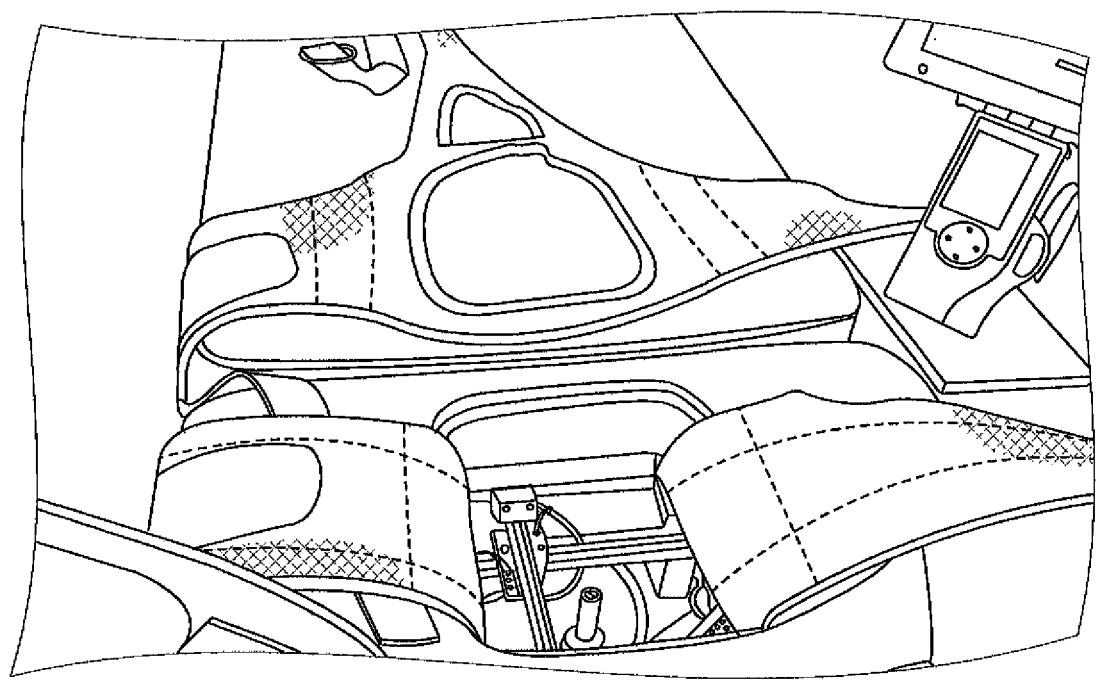
FIG. 32A is side perspective view of an alternative arrangement for the lowers straps that are to be secured across the patient's hips, and which may be incorporated into the cushioned gland or may be fixedly secured thereto.
Figure 32B:
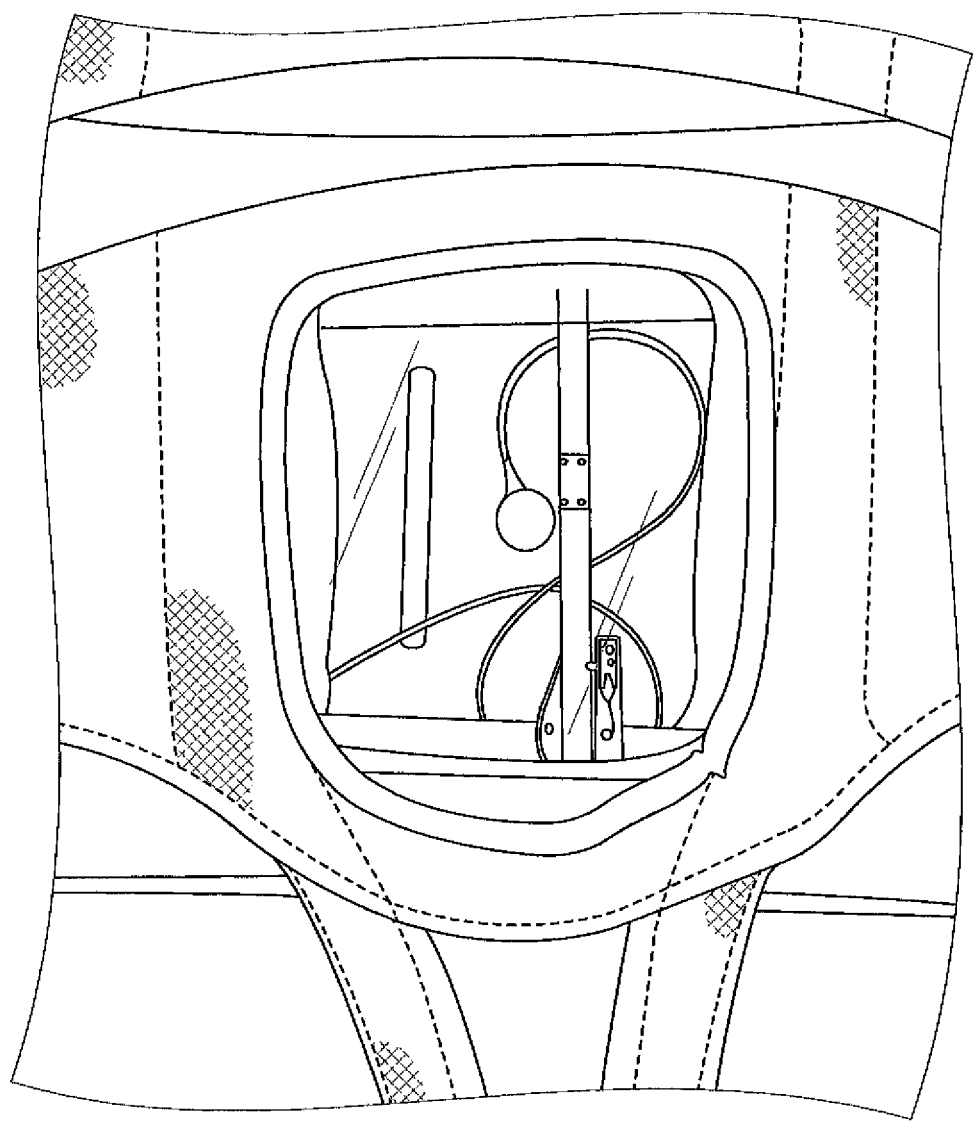
FIG. 32B is a top perspective view of the alternative arrangement for the lowers straps shown in FIG. 32A.

FIG. 32A and FIG. 32B illustrate perspective views of an alternative arrangement for the straps of the patient restraint system of the present invention. The patient restraint system may include an upper strap arrangement (see e.g., FIG. 14B), a lower strap arrangement, and the set of arm bolsters 102, for positioning and retaining the patient for accurate performance of the laser assisted spinal restoration (L.A.S.R.) technique. The upper strap may have a wide polyester band configured to fasten around the rib cage of the patient under the arms. The ends of the straps may be affixed to each other using hook and loop fastening materials sold under the trademarked name of Velcro®, to cradle the patient, and prevent him/her from sliding down the table when caudal traction forces are applied to the lumbar section opening the table sections. The bolsters are devised to be used in concert with the upper polyester strap for affixing the patient to the table to prevent the patient's upper torso from sliding, towards the caudal end of the table under traction.

The lower (lumbar) strap shown in FIGS. 32A-32B, is comprised of two separate sections. The function of the two sections is to promote proper positioning of the patient for L.A.S.R. treatments and also to allow flex between the straps for lateral pull techniques. The present invention is configured to apply decompressive traction to promote lateral flexion in the spine for indicated conditions so some translation between the strap sections is necessary for proper lateral flexion forces to be effective. The inferior section of the low strap has two separate bands; of polyester with Velcro sewn in, to both affix to itself in the front of the patient, and to the superior strap as described below. This inferior section of the lower strap attaches directly to the center table pad (i.e., the cushioned gland), to be above and surrounding the opening for the laser beam.

The superior strap includes a wider band of polyester with its center section cut out according to the size end shape of the opening in the table for the laser. The openings in each of the inferior strap portion and the superior strap portion follow the contours of the opening in the table, to alloy penetration of laser through the center of the strap sections to be unencumbered by the strap material. At the caudal end of this restraint is a Y shaped strap which may loop up and may fasten to the lap belt over top of the patient's pelvic area. The rope/cable of the traction unit may clip into carabiners around the bottom of the Y shaped strap, and may thus exert its pull force to separate the sections of the table and decompress the patient's spine.

A guide for use of the present invention may be provided. The patient should be instructed to lay on his/her back facing up, so that the umbilicus is lined up on the table (i.e., substantially parallel with an axis of the table), with the spinal portion to be treated being centered upon the opening in the padding (i.e., the cushioned gland). The two sets of lower straps are to be affixed in a V position across the patient's hips (see, FIG. 14B). The small belt is to be affixed by attaching the clip and adjusting it to fit securely around the patient's waist. The axial traction strap may be fastened with a carabiner to the strap across the patient's hips. The traction unit carabiner is next fastened to the axial traction strap, and, the cable slack is guided back into the traction nut using "rope release." The upper straps are then affixed in V-position around the patient's rib cage and under his/her arms (sec. FIG. 14B). The underarm bolsters are then positioned to be snug with the sides of the patient's rib cage, but nonetheless comfortable for the patient. The patient is then in a proper restrained, position.

With respect to the cervical section, the neck bolsters should be adjusted to be snug with the patient's neck, for the patient's neck to be nestled comfortably therebetween. The forehead strap 83 should be snugged over the patient's forehead. Next die two smaller temporal straps, 83L and 83R, which are respectively secured to the bolsters 82L and 82R, may be fastened to the over-forehead strap to prevent it from translating.

The manual for the particular traction unit being utilized should be read. Thereafter, the traction unit should be adjusted to the appropriate weight as per clinical judgement and patient tolerance, or the protocol being used. Unless otherwise specified, it is generally suitable to start with 65 pounds of max pull for a lumbar patient, and 25 pounds of max pull for a cervical patient. As per patient tolerance these weight amounts can be raised up to a suggested max of 120 pounds for lumbar, and 45 pounds for cervical. Smaller adult patients weighing under 100 pounds may be started at 50 pounds of maximum pull for lumbar, and the weight may be increased according to the patient's tolerance, per the patient's feedback. One patient may tolerate more pull than another, so patient feedback is paramount.

In general, the laser power may be set for 10 watts. In most cases this does not need to be changed once set. For patients with heat sensitivity, the practitioner may press the "waveform" symbol on the touchscreen under the timer settings to run the laser in "pulsed" mode. This will drop the total power to 5 watts, decreasing the heat perceived by the patient. The laser can then be run for a second cycle during the decompression session. Other options are to manually lower the power output on continuous wave according to patient comfort. (i.e., being decreased to 7.5 watts, with the practitioner asking the patient if it is comfortable for them.)

To begin treatment, the practitioner may turn on the tablet or laptop computer, etc.), and may follow the prompts to activate the spine specialist App, and reach the pattern selection screen. The laser motion pattern may be activated only after decompression has been initiated, as the last step of treatment initiation. Clinical indications and a detailed description of the laser motion patterns is provided for the practitioner to make the best selection for each patient based on diagnosis and clinical judgement. For example, for the majority of patients presenting with general central low back pain, the first "additional" protocol just described would be most applicable for its treatment of the entire low back L1-S1 with concentration of the second pattern dose on L4-S1. This treatment pattern may be considered the default pattern which can be applied to all cases, and may be the ideal application for the first three treatments regardless of presentation. The additional patterns which are more specific to the patient condition should be applied after the first three treatments to focus the therapy on the area of concern.

For example, a patient presents with right sided or central low back pain accompanied by right sided sciatic pain and/or radiculopathy travelling into the right leg. Diagnosis states by MRI or suggests through orthopedic testing that a right sided disc herniation is exerting pressure on the right L5 nerve root. Appropriate management would suggest three treatments of straight axial decompression in combination with the first "additional" laser treatment protocol just described. For the fourth and subsequent treatments, it would be suggested to exert greater decompressive force on the patient's right side by moving the traction unit one adjustment unit to the left, effectively pulling the patient into left lateral flexion, and selecting the fourth additional laser treatment protocol just described, to concentrate on the right sided disc herniation. Every third treatment after this point should intersperse one straight axial decompression treatment following a 2-1 application of the pathology focused treatment and straight axial decompression (i.e., two right lateral focused treatments, one straight axial treatment, two right lateral focused treatments, one axial treatment, and so on . . . ).

Prior to beginning each treatment, the practitioner is to hand the traction unit safety stop switch to the patient, and also direct them to the red stop button positioned on the left side of the table proximate to the laser unit. The practitioner may recite the following to the patient: "Here is the safety stop switch so you know you are in full control of the machine at all times. If you want to end the treatment at any time just press the button and the device will stop. Just rest and let the spine specialist do all the work, most patients just have a bit of a nap while they're on the table so enjoy the nap." Some patients may have anxiety about the first few treatments so this is of utmost importance to put the locus of control in the patient's hands, as it will enhance their comfort and set the pace for further sessions.

To properly enable the software that may be utilized by the present invention, which may run on a computer and/or server, or be accessed therefrom, a description of such a computer system is hereinafter disclosed. An exemplary computer system 200 is shown schematically in FIG. 5, and may comprise a computing, unit 201 interacting with external devices 202, such as a separate touch screen display 245 and the laser treatment table of the current invention 241, and interacting with network resources 203, including use of the internet 262, and other computers, which may be a laptop computer 261.

The computing unit 201 may include a data bus 224 or other communication mechanism for communicating information across and among various parts of computing unit 201, and a central processing unit ("CPU" or "processor") 222 coupled with bus 224 for processing information and performing other computational and control tasks. Computing unit 201 may also include a volatile storage 225, such as a random access memory (RAM) or other dynamic storage device, coupled to bus 224 for storing various information as well as instructions to be executed by processor 222. The RAM may be Dynamic Random Access Memory (DRAM), or Static RAM (SRAM), or any other similar type of RAM known in the art. The volatile storage 225 also may be used for storing temporary variables or other intermediate information during execution of instructions by processor 222. Computing unit 201 may further include a read only memory (ROM) or an erasable programmable memory (EPROM) 227 or other static storage device coupled to bus 224 for storing static information and instructions for processor 222, such as basic input-output system (BIOS), as well as various system configuration parameters. A persistent storage device or non-volatile memory 226, such as a magnetic disk, optical disk, or solid-state flash memory device may be provided and may be coupled to bus 224 for storing information and instructions.

Computing unit 201 may be coupled via bus 224 to an integral touch screen display screen 221, such as a liquid crystal display (LCD), for displaying information to a user of the computing unit 201. If desired, the computing unit 201 may also be coupled via bus 224 to an external display screen 245. An external input device 244, including alphanumeric and other keys, may also be coupled to bus 224 for communicating information and command selections to processor 222. A cursor control device 243, such as a mouse, a trackball, or cursor direction keys for communicating direction information and command selections to processor 222 and for controlling cursor movement on display 245 or 221, may be used, if desired, as well as an external storage device 242.

According to one embodiment of the invention, the techniques described herein may be performed by computing unit 201 in response to processor 222 executing one or more sequences of one or more instructions contained in the volatile memory 225. Such instructions may be read into volatile memory 275 from another computer-readable medium, such as persistent storage device or non-volatile memory device 226. Execution of the sequences of instructions contained in the volatile memory 225 causes processor 222 to perform the process steps described herein. In alternative embodiments, hard-wired circuitry may be used in place of or in combination with, software instructions to implement the invention.

The term "computer-readable medium" as used herein refers to any medium that participates in providing instructions to processor 222 for execution. Such a medium may take many forms, but common forms of computer-readable media include, but are not limited to: a floppy disk, a hard disk, magnetic tape, or any other magnetic medium, a CD-ROM, any other optical medium, punchcards, papertape, a RAM, a PROM, an EPROM, a FLASH-EPROM, a flash drive, and a memory card.

Various forms of computer readable media may be involved in carrying one or more sequences of one or more instructions to processor 222 for execution. For example, the instructions may initially be carried on a magnetic disk from a remote computer. Alternatively, a remote computer can load the instructions into its dynamic memory and send the instructions over a telephone line using a modem. A modem local to computer system 200 can receive the data on the telephone line. The bus 222 may carry the data to the volatile storage 225, from which processor 222 retrieves and executes the instructions. The instructions received by the volatile memory 225 may optionally be stored on persistent storage device 226 either before or after execution by processor 222. The instructions may also be downloaded into the computing unit 201 via the internet 261.

The computing unit 201 may also include a communication interface, such as network interface card 22 coupled to the data bus 222. Communication interface 223 may provide a two-way data communication coupling to a network link that may be connected to a local network. For example, communication interface 223 may be an integrated services digital network (ISDN) card or a modem to provide a data communication connection to a corresponding type of telephone line. As another example, communication interface 223 may be a local area network interface card (LAN NIC) to provide a data communication connection to a compatible LAN. In any such implementation, communication interface 223 sends and receives electrical, electromagnetic or optical signals that carry digital data streams representing various types of information. The network link may provide a connection over the internet 262 to the world-wide-web, to thereby access resources located any here. The computing unit 201 may also thereby be accessed by others with permission, such as laptop computers 261, which may be located anywhere with access to the internet 262.

Computing unit 201 may be able to send messages and receive data, including program code, through the variety of network(s) including the Internet 262, network link and communication interface 223. Similarly, it may receive code from other network resources. The received code may be executed by processor 222 as it is received, and/or stored in persistent or volatile storage devices and 225, respectively, or other non-volatile storage for later execution. In this matter, computer system 200 may obtain application code for remote sources.

The examples and descriptions provided merely illustrate preferred embodiments of the present invention. Those skilled in the art and having the benefit, of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

What is claimed is:

1. A computer-controlled treatment table configured for application of non-surgical spinal decompression and laser treatment protocols to a portion of a patient's spine, said computer-controlled treatment table comprising:
   a frame;
   a body support member secured to said frame and comprising an opening positioned at a distance from a periphery of said body support member;
   means for providing adjustable cervical support, being secured to said body support table;
   an enclosure; a first side of said enclosure comprising an opening into a cavity therein; said first side of said enclosure fixedly secured and sealed with respect to an underside of said body support member, with said opening in said enclosure positioned to interconnect with said opening in said body support member;
   a laser hand-piece comprising a class four medical laser, said class four medical laser comprising a lens configured to diverge a beam of light emitted from said laser and to maintain a uniform intensity across a width of said beam;
   a cushioned gland; said cushioned gland fixedly secured and sealed with respect to a top of said body support member; about an entire perimeter of said opening in said body support member; said cushioned gland comprising an opening, at least a portion of said opening in said cushioned gland configured to interconnect with said opening in said enclosure; an entire periphery of said cushioned gland configured to seal against the patient;
   means for releasably supporting and translating in two dimensions said laser hand-piece within said cavity, for selectively directing said beam of light through said interconnected openings of said enclosure and said cushioned gland, onto the portion of the patient's spine;
   a traction platform member configured to support a traction machine to apply a sustained tension force to the portion of the patient's spine; and
   a motion controller configured to control said means for releasably supporting and translating in two dimensions said laser hand-piece, for said selective directing of said beam of laser light to thereby track in a pattern with respect to the portion of the patients spine to be treated, according to a pre-programmed treatment protocol, in combination with the traction provided thereto.

2. The computer-controlled treatment table according to claim 1 further comprising means for adjusting a height of said traction platform member for providing the traction at a selective rope angle, with respect to said top of said body support member, in combination with said pattern of laser light of said pre-programmed treatment protocol.

3. The computer-controlled treatment table according to claim 2 further comprising means for adjusting a lateral position of said traction platform member with respect to an axis of said body support member.

4. The computer-controlled treatment table according to claim 1 further comprising a safety stop switch configured to be held by the patient, said safety stop switch configured to shut down said emitted laser light when toggled by the patient.

5. The computer-controlled treatment table according to claim 1 wherein said selective directing of said beam of laser light to track in a pattern comprises said laser being directed to track in a ladder pattern.

6. The computer-controlled treatment table according to claim 1 further comprising one or more temperature sensors configured to monitor tissue temperatures of the patient to achieve an optimal laser light dosage.

7. The computer-controlled treatment table according to claim 1 further comprising one or more proximity sensors positioned near said opening in said enclosure and configured to detect the patient thereon, said one or more proximity sensors coupled to a switch configured to shut down said emitted laser light when said one or more proximity switches fail to detect the patient.

8. The computer-controlled treatment table according to claim 1 wherein said class four medical laser is configured to emit light at one or more wavelengths, and is configured to provide a depth of penetration for said emitted light of approximately 10 cm on a full power setting.

9. The computer-controlled treatment table according to claim 8 wherein said laser is configured to deliver 620 joules per minute of energy, and is configured to emit said one or more wavelengths to be at 940 nm+/−15 nm.

10. A treatment table configured for application of non-surgical spinal decompression and laser light treatment to a patient's spine, said treatment table comprising:
   a body support member comprising an opening positioned at a distance from a periphery of said body support member;
   an enclosure; a first side of said enclosure comprising an opening into a cavity therein; said first side of said enclosure fixedly secured and sealed with respect to an underside of said body support member, with said opening in said enclosure positioned to interconnect with said opening in said body support member;
   a class four medical laser;
   a cushioned gland; said cushioned gland fixedly secured and sealed with respect to a top of said body support member, about an entire perimeter of said opening in said body support member; said cushioned gland comprising an opening, at least a portion of said opening in said cushioned gland configured to interconnect with said opening in said enclosure; an entire periphery of said cushioned gland configured to seal against the patient;
   means for releasably supporting and translating in two dimensions said laser within said cavity, for selectively directing a beam of light emitted by said laser through said interconnected openings of said enclosure and said cushioned gland, onto the portion of the patients spine;
   means for supporting a traction machine configured to apply a tension force the portion of the patient's spine; and
   a motion controller configured to control said means for releasably supporting and translating in two dimensions for said selective directing of said beam of laser light to track in a pattern with respect to the portion of the patients spine to be treated, according to a pre-programmed treatment protocol, in combination with the traction applied thereto.

11. The treatment table according to claim 10 further comprising a safety stop switch configured to be held by the patient, said safety stop switch configured to shut down said emitted laser light when toggled by the patient.

12. The treatment table according to claim 10 wherein said selective directing of said beam of laser light to track in a pattern comprises said laser being directed to track in a ladder pattern.

13. The treatment table according to claim 10 further comprising one or more temperature sensors configured to monitor tissue temperatures of the patient to achieve an optimal laser light dosage.

14. The treatment table according to claim 10 further comprising one or more proximity sensors positioned near said opening in said enclosure and configured to detect the patient, said one or more proximity sensors coupled to a switch configured to shut down said emitted laser light when said one or more proximity switches fail to detect the patient.

15. The treatment table according to claim 10 wherein said class four medical laser is configured to emit light at one or more wavelengths, and is configured to provide a depth of penetration for said emitted light of approximately 10 cm on a full power setting.

16. The treatment table according to claim 15 wherein said laser is configured to deliver 620 joules per minute of energy, and is configured to emit said one or more wavelengths to be at 940 nm+/−15 nm.

* * * * *